(12) United States Patent
Pardridge et al.

(10) Patent No.: US 11,512,145 B2
(45) Date of Patent: *Nov. 29, 2022

(54) METHODS AND COMPOSITIONS FOR INCREASING ALPHA-L-IDURONIDASE ACTIVITY IN THE CNS

(71) Applicant: Armagen, Inc., Agoura Hills, CA (US)

(72) Inventors: William M. Pardridge, Pacific Palisades, CA (US); Ruben J. Boado, Agoura Hills, CA (US)

(73) Assignee: ARMAGEN, INC., Calabasas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/264,343

(22) Filed: Jan. 31, 2019

(65) Prior Publication Data

US 2019/0389975 A1    Dec. 26, 2019

Related U.S. Application Data

(63) Continuation of application No. 15/397,649, filed on Jan. 3, 2017, now Pat. No. 10,202,467, which is a
(Continued)

(51) Int. Cl.
   *C07K 16/46*   (2006.01)
   *A61K 47/68*   (2017.01)
   (Continued)

(52) U.S. Cl.
   CPC ............ *C07K 19/00* (2013.01); *A61K 9/0019* (2013.01); *A61K 47/6849* (2017.08);
   (Continued)

(58) Field of Classification Search
   CPC ............... C07K 16/2869; C07K 16/46; C07K 2317/622; C07K 2317/92; C07K 2317/94;
   (Continued)

(56) References Cited

U.S. PATENT DOCUMENTS

| 4,801,575 A | 1/1989 | Pardridge |
| 4,902,505 A | 2/1990 | Pardridge et al. |

(Continued)

FOREIGN PATENT DOCUMENTS

| EP | 0613007 A2 | 8/1994 |
| EP | 0613007 A3 | 10/1995 |

(Continued)

OTHER PUBLICATIONS

De Graaf M et al. A fully human anti-EP-CAM scFv-beta-glucuronidase fusion protein for selective chemotherapy with a glucuronide prodrug. British J. Cancer, 86, 811-818. (Year: 2002).*
(Continued)

*Primary Examiner* — Kimberly Ballard
(74) *Attorney, Agent, or Firm* — Wilson Sonsini Goodrich & Rosati

(57) ABSTRACT

Provided herein are methods and compositions for treating a subject suffering from a deficiency in α-L-Iduronidase in the CNS. The methods include systemic administration of a bifunctional fusion antibody comprising an antibody to a human insulin receptor and an α-L-Iduronidase. A therapeutically effective systemic dose is based on the specific CNS uptake characteristics of human insulin receptor antibody-α-L-Iduronidase fusion antibodies as described herein.

11 Claims, 20 Drawing Sheets

Specification includes a Sequence Listing.

Related U.S. Application Data continuation of application No. 14/606,239, filed on Jan. 27, 2015, now Pat. No. 9,567,400, which is a continuation of application No. 12/179,806, filed on Jul. 25, 2008, now Pat. No. 8,974,791.

(60) Provisional application No. 60/952,547, filed on Jul. 27, 2007.

(51) Int. Cl.

| | | |
|---|---|---|
| *C07K 16/28* | (2006.01) | |
| *A61K 9/00* | (2006.01) | |
| *C07K 19/00* | (2006.01) | |
| *C07K 16/40* | (2006.01) | |
| *C12N 9/00* | (2006.01) | |
| *C12N 9/24* | (2006.01) | |
| *A61K 39/00* | (2006.01) | |
| *A61K 38/00* | (2006.01) | |

(52) U.S. Cl.
CPC .......... *C07K 16/2869* (2013.01); *C07K 16/40* (2013.01); *C07K 16/46* (2013.01); *C12N 9/0002* (2013.01); *C12N 9/2402* (2013.01); *C12Y 302/01076* (2013.01); *A61K 38/00* (2013.01); *A61K 47/6801* (2017.08); *A61K 47/6815* (2017.08); *A61K 47/6843* (2017.08); *A61K 2039/505* (2013.01); *C07K 2317/24* (2013.01); *C07K 2317/51* (2013.01); *C07K 2317/515* (2013.01); *C07K 2317/55* (2013.01); *C07K 2317/565* (2013.01); *C07K 2317/622* (2013.01); *C07K 2317/92* (2013.01); *C07K 2317/94* (2013.01); *C07K 2319/00* (2013.01)

(58) Field of Classification Search
CPC ............ C07K 2319/00; C07K 16/2881; A61K 9/0019; A61K 47/6843; A61K 47/6849; A61K 47/6801; A61K 47/6815; C12Y 302/01076

See application file for complete search history.

(56) References Cited

U.S. PATENT DOCUMENTS

| | | |
|---|---|---|
| 4,946,778 A | 8/1990 | Ladner et al. |
| 5,154,924 A | 10/1992 | Friden |
| 5,180,820 A | 1/1993 | Barde et al. |
| 5,182,107 A | 1/1993 | Friden |
| 5,229,500 A | 7/1993 | Barde et al. |
| 5,438,121 A | 8/1995 | Barde et al. |
| 5,453,361 A | 9/1995 | Yancopoulos et al. |
| 5,527,288 A | 6/1996 | Gross et al. |
| 5,527,527 A | 6/1996 | Friden |
| 5,562,903 A | 10/1996 | Co et al. |
| 5,610,279 A | 3/1997 | Brockhaus et al. |
| 5,618,920 A | 4/1997 | Robinson et al. |
| 5,656,284 A | 8/1997 | Balkin |
| 5,672,683 A | 9/1997 | Friden et al. |
| 5,693,762 A | 12/1997 | Queen et al. |
| 5,824,782 A | 10/1998 | Hoelzer et al. |
| 5,837,231 A | 11/1998 | Low et al. |
| 5,848,991 A | 12/1998 | Gross et al. |
| 5,977,307 A | 11/1999 | Friden et al. |
| 5,997,501 A | 12/1999 | Gross et al. |
| 6,015,662 A | 1/2000 | Hackett, Jr. et al. |
| 6,041,775 A | 3/2000 | Century |
| 6,060,069 A | 5/2000 | Hill et al. |
| 6,153,190 A | 11/2000 | Young et al. |
| 6,165,476 A | 12/2000 | Strom et al. |
| 6,165,783 A | 12/2000 | Weiss et al. |
| 6,201,105 B1 | 3/2001 | Smith et al. |
| 6,248,262 B1 | 6/2001 | Kubotera et al. |
| 6,284,262 B1 | 9/2001 | Place |
| 6,287,792 B1 | 9/2001 | Pardridge et al. |
| 6,322,808 B1 | 11/2001 | Trautman et al. |
| 6,329,508 B1 | 12/2001 | Friden |
| 6,348,210 B1 | 2/2002 | Gale |
| 6,361,760 B1 | 3/2002 | Murata et al. |
| 6,372,250 B1 | 4/2002 | Pardridge |
| 6,375,975 B1 | 4/2002 | Modi |
| 6,531,309 B1 | 3/2003 | Hu et al. |
| 6,541,610 B1 | 4/2003 | Smith |
| 6,582,945 B1 | 6/2003 | Raso |
| 6,583,272 B1 | 6/2003 | Bailon |
| 6,709,833 B2 | 3/2004 | Fukui et al. |
| 6,743,427 B1 | 6/2004 | Schenk |
| 6,858,206 B2 | 2/2005 | Kakkis |
| 7,053,202 B2 | 5/2006 | O'Keefe et al. |
| 7,078,376 B1 | 7/2006 | Thompson |
| 7,214,658 B2 | 5/2007 | Tobinick et al. |
| 7,226,758 B1 | 6/2007 | Lin et al. |
| 7,294,704 B2 | 11/2007 | Simon et al. |
| 7,309,687 B1 | 12/2007 | Brines et al. |
| 7,341,720 B2 | 3/2008 | Stefano |
| 7,388,079 B2 | 6/2008 | Pardridge et al. |
| 7,396,811 B2 | 7/2008 | LeBowitz et al. |
| 7,560,424 B2 | 7/2009 | LeBowitz et al. |
| 7,629,309 B2 | 12/2009 | LeBowitz et al. |
| 7,700,097 B2 | 4/2010 | Braslawsky et al. |
| 7,741,446 B2 | 6/2010 | Pardridge et al. |
| 7,744,879 B2 | 6/2010 | Shusta et al. |
| 7,807,409 B2 | 10/2010 | Kopetzki |
| 7,981,417 B2 | 7/2011 | Shusta et al. |
| 8,053,569 B2 | 11/2011 | Pardridge et al. |
| 8,084,026 B2 | 12/2011 | Glaser et al. |
| 8,124,073 B2 | 2/2012 | Stefano |
| 8,124,095 B2 | 2/2012 | Pardridge et al. |
| 8,142,781 B2 | 3/2012 | Pardridge et al. |
| 8,227,212 B2 | 7/2012 | Figura et al. |
| 8,486,399 B2 | 7/2013 | Pardridge et al. |
| 8,497,246 B2 | 7/2013 | Pardridge et al. |
| 8,603,473 B2 | 12/2013 | Glaser et al. |
| 8,715,661 B2 | 5/2014 | Pardridge et al. |
| 8,741,260 B2 | 6/2014 | Pardridge et al. |
| 8,753,610 B2 | 6/2014 | Pardridge et al. |
| 8,759,297 B2 | 6/2014 | Pardridge et al. |
| 8,834,874 B2 | 9/2014 | Pardridge et al. |
| 8,853,353 B2 | 10/2014 | Beliveau et al. |
| 8,906,379 B2 | 12/2014 | Stefano |
| 8,920,801 B2 | 12/2014 | Pardridge et al. |
| 8,974,791 B2 | 3/2015 | Pardridge et al. |
| 9,533,055 B2 | 1/2017 | Pardridge et al. |
| 9,611,323 B2 | 4/2017 | Dennis et al. |
| 10,011,651 B2 | 7/2018 | Pardridge et al. |
| 10,144,783 B2 | 12/2018 | Pardridge et al. |
| 10,202,467 B2 | 2/2019 | Pardridge |
| 10,538,589 B2 | 1/2020 | Pardridge et al. |
| 10,940,185 B2 | 3/2021 | Yasukawa et al. |
| 10,941,215 B2 | 3/2021 | Dennis et al. |
| 11,111,308 B2 | 9/2021 | Sonoda et al. |
| 2002/0052311 A1 | 5/2002 | Solomon et al. |
| 2002/0137684 A1 | 9/2002 | Tchistiakova et al. |
| 2002/0169109 A1 | 11/2002 | Plata-Salaman et al. |
| 2003/0072761 A1 | 4/2003 | LeBowitz |
| 2003/0082176 A1 | 5/2003 | LeBowitz et al. |
| 2003/0129186 A1 | 7/2003 | Beliveau et al. |
| 2003/0165853 A1 | 9/2003 | Partridge et al. |
| 2004/0005309 A1 | 1/2004 | LeBowitz et al. |
| 2004/0006008 A1 | 1/2004 | LeBowitz et al. |
| 2004/0043446 A1 | 3/2004 | Defrees et al. |
| 2004/0072291 A1 | 4/2004 | Carr et al. |
| 2004/0101904 A1* | 5/2004 | Pardridge ............... A61P 25/00 435/7.1 |
| 2004/0102369 A1 | 5/2004 | Wu et al. |
| 2004/0229250 A1 | 11/2004 | Figura et al. |
| 2004/0248197 A1 | 12/2004 | Holtzman et al. |
| 2005/0026823 A1 | 2/2005 | Zankel et al. |
| 2005/0142141 A1 | 6/2005 | Pardridge |
| 2005/0163782 A1 | 7/2005 | Glaser et al. |
| 2005/0163783 A1 | 7/2005 | Braslawsky et al. |
| 2005/0244400 A1 | 11/2005 | LeBowitz et al. |
| 2005/0281805 A1 | 12/2005 | LeBowitz et al. |

(56) References Cited

U.S. PATENT DOCUMENTS

| | | |
|---|---|---|
| 2006/0228348 A1 | 10/2006 | Stefano |
| 2007/0031402 A1 | 2/2007 | Zhang et al. |
| 2007/0081992 A1 | 4/2007 | Pardridge et al. |
| 2007/0082380 A1 | 4/2007 | Pardridge et al. |
| 2007/0275882 A1 | 11/2007 | Meijer et al. |
| 2007/0280940 A1 | 12/2007 | Winkles et al. |
| 2008/0003211 A1 | 1/2008 | Fogh et al. |
| 2008/0019984 A1 | 1/2008 | Shusta et al. |
| 2008/0051564 A1 | 2/2008 | Pardridge et al. |
| 2008/0152645 A1 | 6/2008 | Pardridge et al. |
| 2008/0170994 A1 | 7/2008 | Pardridge et al. |
| 2008/0171055 A1 | 7/2008 | Pardridge et al. |
| 2008/0226658 A1 | 9/2008 | Stefano |
| 2008/0292639 A1 | 11/2008 | Shen et al. |
| 2008/0292704 A1 | 11/2008 | Arnason et al. |
| 2009/0041758 A1 | 2/2009 | Glaser et al. |
| 2009/0047338 A1 | 2/2009 | Swamy et al. |
| 2009/0068206 A1 | 3/2009 | Pardridge et al. |
| 2009/0156498 A1 | 6/2009 | Pardridge et al. |
| 2009/0162380 A1 | 6/2009 | Glaser et al. |
| 2009/0238789 A1 | 9/2009 | Guyon et al. |
| 2009/0270267 A1 | 10/2009 | Akiyama et al. |
| 2009/0304696 A1 | 12/2009 | Lawson et al. |
| 2010/0077498 A1 | 3/2010 | Pardridge et al. |
| 2010/0098693 A1 | 4/2010 | Pardridge et al. |
| 2010/0172919 A1 | 7/2010 | Grimm et al. |
| 2010/0175141 A1 | 7/2010 | Collins et al. |
| 2010/0183577 A1 | 7/2010 | Stern et al. |
| 2010/0209425 A1 | 8/2010 | Shusta et al. |
| 2010/0261647 A1 | 10/2010 | Pardridge et al. |
| 2010/0290985 A1 | 11/2010 | Pardridge et al. |
| 2011/0110935 A1 | 5/2011 | Pardridge et al. |
| 2011/0262460 A1 | 10/2011 | Shusta et al. |
| 2011/0318327 A1 | 12/2011 | Concino et al. |
| 2012/0014936 A1 | 1/2012 | Natoli et al. |
| 2012/0094934 A1 | 4/2012 | Collard et al. |
| 2012/0141507 A1 | 6/2012 | Stefano |
| 2012/0232021 A1 | 9/2012 | Martini et al. |
| 2013/0039888 A1 | 2/2013 | McCarty et al. |
| 2013/0095092 A1 | 4/2013 | Quinn et al. |
| 2013/0130292 A1 | 5/2013 | Szalay et al. |
| 2013/0142794 A1 | 6/2013 | Pardridge et al. |
| 2013/0287773 A1 | 10/2013 | Pardridge et al. |
| 2013/0295077 A1 | 11/2013 | Concino et al. |
| 2013/0323221 A1 | 12/2013 | Radin |
| 2014/0037621 A1 | 2/2014 | Tsurushita et al. |
| 2014/0187502 A1 | 7/2014 | Martini et al. |
| 2014/0193409 A1 | 7/2014 | Pardridge et al. |
| 2014/0294822 A1 | 10/2014 | Pardridge et al. |
| 2015/0023956 A1 | 1/2015 | Pardridge et al. |
| 2015/0064184 A1 | 3/2015 | Pardridge |
| 2015/0203586 A1 | 7/2015 | Pardridge et al. |
| 2015/0258180 A1 | 9/2015 | Mahuran et al. |
| 2015/0320844 A1 | 11/2015 | Stefano et al. |
| 2016/0137994 A1 | 5/2016 | Ito et al. |
| 2016/0152719 A1 | 6/2016 | Pardridge |
| 2016/0208006 A1 | 7/2016 | Pardridge et al. |
| 2016/0208009 A1 | 7/2016 | Umana et al. |
| 2017/0042979 A1 | 2/2017 | Stefano |
| 2017/0066832 A1 | 3/2017 | Pardridge |
| 2021/0269543 A1 | 9/2021 | Sonoda et al. |

FOREIGN PATENT DOCUMENTS

| | | |
|---|---|---|
| EP | 2051734 A2 | 4/2009 |
| EP | 2182980 A2 | 5/2010 |
| EP | 2408474 A2 | 1/2012 |
| EP | 2485761 A1 | 8/2012 |
| EP | 2785378 A1 | 10/2014 |
| JP | H06228199 A | 8/1994 |
| JP | 2016529759 A | 9/2016 |
| WO | WO-9802421 A1 | 1/1998 |
| WO | WO-9900150 A2 | 1/1999 |
| WO | WO-9900951 A1 | 1/1999 |
| WO | WO-9900150 A3 | 4/1999 |
| WO | WO-9966951 A2 | 12/1999 |
| WO | WO-0015759 A1 | 3/2000 |
| WO | WO-0037502 A2 | 6/2000 |
| WO | WO-0051621 A1 | 9/2000 |
| WO | WO-0145730 A2 | 6/2001 |
| WO | WO-02087510 A2 | 11/2002 |
| WO | WO-03032727 A1 | 4/2003 |
| WO | WO-03032913 A2 | 4/2003 |
| WO | WO-03074081 A1 | 9/2003 |
| WO | WO-03102583 A1 | 12/2003 |
| WO | WO-2004003019 A2 | 1/2004 |
| WO | WO-2004050016 A2 | 6/2004 |
| WO | WO-2004108071 A2 | 12/2004 |
| WO | WO-2005078077 A2 | 8/2005 |
| WO | WO-2006081171 A1 | 8/2006 |
| WO | WO-2007022416 A2 | 2/2007 |
| WO | WO-2007044323 A2 | 4/2007 |
| WO | WO-2007022416 A3 | 5/2007 |
| WO | WO-2008022349 A2 | 2/2008 |
| WO | WO-2009018122 A2 | 2/2009 |
| WO | WO-2007044323 A3 | 5/2009 |
| WO | WO-2009070597 A2 | 6/2009 |
| WO | WO-2009137721 A2 | 11/2009 |
| WO | WO-2010003101 A2 | 1/2010 |
| WO | WO-2010108048 A2 | 9/2010 |
| WO | WO-2011044542 A1 | 4/2011 |
| WO | WO-2011163649 A2 | 12/2011 |
| WO | WO-2012075037 A1 | 6/2012 |
| WO | WO-2012177997 A1 | 12/2012 |
| WO | WO-2013081706 A1 | 6/2013 |
| WO | WO-2014005014 A2 | 1/2014 |
| WO | WO-2015009961 A | 1/2015 |
| WO | WO-2015012944 A1 | 1/2015 |

OTHER PUBLICATIONS

Recombinant Human alpha-L-lduronidase/IDUA, R&D Systems product sheet, Cat#4119-GH, revised Oct. 19, 2020, 2 pages. (Year: 2020).*

Accusation by Medical Board of California dated Nov. 24, 2014 against Edward Tobinick before the Medical Board of California. Case No. 04/2012-224707.

Advisory action dated Jun. 13, 2014 for U.S. Appl. No. 13/141,682.

Aharoni, et al. Directed evolution of mammalian paraoxonases PON1 and PON3 for bacterial expression and catalytic specialization. Proc Natl Acad Sci U S A. Jan. 13, 2004;101(2):482-7. Epub Dec. 26, 2003.

Ai, et al., 2003. Intraputamenal Infusion Of GDNF in Aged Rhesus Monkeys: Distribution and Dopaminergic Effects. The Journal of Comparative Neurology 461: 250-261.

Airavaara, et al. Effects of repeated morphine on locomotion, place preference and dopamine in heterozygous glial cell line-derived neurotrophic factor knockout mice. Genes Brain Behav. Apr. 2007;6(3):287-98.

Akiyama, et al. Enzyme augmentation therapy enhances the therapeutic efficacy of bone marrow transplantation in mucopolysaccharidosis type II mice. Mol Genet Metab. Feb. 2014;111(2):139-46. doi: 10.1016/j.ymgme.2013.09.013. Epub Sep. 21, 2013.

Al Sawaf, et al. Neurological findings in Hunter disease: pathology and possible therapeutic effects reviewed. J Inherit Metab Dis. Aug. 2008:31(4):473-80.

Albayrak, et al. Effect of transient focal ischemia on blood-brain barrier permeability in the rat: Correlation to Cell Injury. Acta Neuropathol 1997;94:158-63.

Albeck, et al. A non-invasive transport system for GDNF across the blood-brain barrier. NeuroReport. Jul. 7, 1997; 8(9-10):2293-2298.

Alberts, et al. Molecular Biology of the Cell. 3rd Edition. Garland Publishing Inc. New York. 1994; pp. 1206-1207.

Almagro, J. Identification of differences in the specificity-determining residues of antibodies that recognize antigens of different size: implications for the rational design of antibody repertoires. J Mol Recognit. Mar.-Apr. 2004;17(2):132-43.

Altschul, et al. Optimal sequence alignment using affine gap costs. Bulletin of Mathematical Biology. 1986; 48(5-6):603-16.

(56) References Cited

OTHER PUBLICATIONS

Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1977).
Amgen www.amgen.com Accessed Dec. 16, 2005.
Arndt, et al. Generation of a highly stable, internalizing anti-CD22 single-chain Fv fragment for targeting non-Hodgkin's lymphoma. Int J Cancer. Dec. 10, 2003;107(5):822-829.
Aronovich et al., "Molecular Genetic Defect Underlying α-L-Iduronidase pseudodeficiency," Am. Journ. Hum. Genet. 58: 75-85 (1996).
Auclair, et al. Repeated intrathecal injections of recombinant human 4-sulphatase remove dural storage in mature mucopolysaccharidosis VI cats primed with a short-course tolerisation regimen. Mol Genet Metab. Feb. 2010;99(2):132-41. doi: 10.1016/j.ymgme.2009.10.002. Epub Oct. 13, 2009.
Ausubel, et al. Current Protocols in Molecular Biology. John Wiley & Sons, New York, 1995 supplement.
Bachis, et al. 2003. Brain-Derived Neurotropic Factor Inhibits Human Immunodeficiency Virus-1/gp 120-Mediated Cerebellar Granule Cell Death by Preventing gp 120 Internalization. The Journal of Neuroscience 23 (13): 5712-22.
Baloh, et al. Functional mapping of receptor specificity domains of glial cell line-derived neurotrophic factor (GDNF) family ligands and production of GFRalphal RET-specific agonists. J Biol Chem. Feb. 4, 2000;275(5):3412-20.
Barth et al. Boron neutron capture therapy of brain tumors: an emerging therapeutic modality. Neurosurgery. Mar. 1999;44(3):433-50; discussion 450-1.
Batzer et al. Enhanced evolutionary PCR using oligonucleotides with inosine at the 3'-terminus. Nucleic Acid Res 19:5081 (1991).
Beck, et al. 1994. Brain-Derived Neurotropic Factor Protects Against Ischemic Cell Damage in Rat Hippocampus. Journal of Cerebral Blood Flow and Metabolism 14: 689-92.
Begley et al., "Lysosomal storage diseases and the blood-brain barrier," Current Pharmaceutical Design, vol. 14, No. 16, pp. 1566-1580 (2008).
Benito, et al. Beta-galactosidase enzymatic activity as a molecular probe to detect specific antibodies. J Biol Chem. Aug. 30, 1996;271(35):21251-6.
Bickel; et al., "In vivo demonstration of subcellular localization of anti-transferrin receptor monoclonal antibody-colloidal gold conjugate in brain capillary endothelium", J Histochem Cytochem, Nov. 1994, 42(11), 1493-7.
Bifare, et al. 2005. Brain-Derived Neurotropic Factor Protects against Multiple Forms of Brain Injury in Bacterial Meningitis. The Journal of Infectious Diseases 191: 40- 45.
Biffi, A. et al. Correction of metachromatic leukodystrophy in the mouse model by transplantation of genetically modified hematopoietic stem cells. J. Clin. Invest., 113(8); p. 1118-1129 (2004).
Biogen Idec www.idecpharma.com/site/home.html Accessed Dec. 16, 2005.
Boado, et al. AGT-181: expression in CHO cells and pharmacokinetics, safety, and plasma iduronidase enzyme activity in Rhesus monkeys. Oct. 2009; 144(2):135-41.
Boado, et al. Blood-brain barrier molecular trojan horse enables imaging of brain uptake of radioiodinated recombinant protein in the rhesus monkey. Bioconjug Chem. Oct. 16, 2013;24(10):1741-9. doi: 10.1021/bc400319d. Epub Oct. 3, 2013.
Boado, et al. CHO cell expression, long-term stability, and primate pharmacokinetics and brain uptake of an IgG-paroxonase-1 fusion protein. Biotechnol Bioeng. Jan. 2011;108(1):186-96.
Boado, et al. Drug delivery of antisense molecules to the brain for treatment of Alzheimer's disease and cerebral AIDS. J Pharm Sci. Nov. 1998;87(11):1308-15.
Boado et al., "Drug targeting of erythropoietin across the primate blood-brain barrier with an IgG molecular Trojan horse," Journal of Pharmacology and Experimental Therapeutics, vol. 333, No. 3, Jun. 1, 2010; 961-969.
Boado, et al. Engineering and expression of a chimeric transferrin receptor monoclonal antibody for blood-brain barrier delivery in the mouse. Biotechnol Bioeng. Mar. 1, 2009;102(4):1251-8.
Boado, et al. Fusion Antibody for Alzheimer's Disease with Bi-Directional Transport Across the Blood-Brain Barrier and Abeta Fibril Disaggregation. Bioconjug Chem. 2007;18(2):447-55.
Boado, et al. GDNF fusion protein for targeted-drug delivery across the human blood-brain barrier. Biotechnol Bioeng. Jun. 1, 2008;100(2):387-96.
Boado, et al. Genetic engineering, expression, and activity of a fusion protein of a human neurotrophin and a molecular Trojan horse for delivery across the human blood-brain barrier. Biotechnology and Bioengineering. 2007;97:1376-1386.
Boado et al., "Genetic engineering of a lysosomal enzyme fusion protein for targeted delivery across the human blood-brain barrier," Biotechnology and Bioengineering, vol. 99, No. 2, pp. 475-484 (2008).
Boado et al., "Genetic Engineering of IgG-glucuronidase fusion proteins," J. Drug Targeting 18(3):205-11 (2010).
Boado, et al. Glycemic control and chronic dosing of rhesus monkeys with a fusion protein of iduronidase and a monoclonal antibody against the human insulin receptor. Drug Metab Dispos. Oct. 2012;40(10):2021-5. doi: 10.1124/dmd.112.046375. Epub Jul. 20, 2012.
Boado, et al. Humanization of anti-human insulin receptor antibody for drug targeting across the human blood-brain barrier. Biotechnology and Bioengineering. 2007;96:381-391.
Boado et al. IgG-enzyme fusion protein: pharmacokinetics and anti-drug antibody response in rhesus monkeys. Bioconjug Chem. 24(1):97-104 (2013).
Boado et al., "IgG-single chain Fv fusion protein therapeutic for Alzheimer's disease: Expression in CHO cells and pharmacokinetics and brain delivery in the rhesus monkey," Biotechnology and Bioengineering, vol. 105, No. 3, pp. 627-635 (2010).
Boado et al., "Pharmacokinetics and brain uptake of a genetically engineered bifunctional fusion antibody targeting the mouse transferrin receptor," Molecular Pharmaceutics, vol. 7, No. 1, pp. 237-244 (2010).
Boado, et al. Reversal of lysosomal storage in brain of adult MPS-I mice with intravenous Trojan horse-iduronidase fusion protein. Mol Pharm. Aug. 1, 2011;8(4):1342-50. Epub Jun. 17, 2011.
Boado, et al. Selective targeting of a TNFR decoy receptor pharmaceutical to the primate brain as a receptor-specific IgG fusion protein. J Biotechnol. Mar. 2010;146(1-2):84-91.
Board of Patent Appeals and Interferences (BPAI) Decision dated Jul. 22, 2010 from U.S. Appl. No. 11/061,956.
Bosslet, et al. Molecular and functional characterisation of a fusion protein suited for tumour specific prodrug activation. Br J Cancer. Feb. 1992;65(2):234-8.
Bosslet, et al. Tumor-selective prodrug activation by fusion protein-mediated catalysis. Cancer Res. Apr. 15, 1994;54(8):2151-9.
Braun, et al. Metabolic correction and cross-correction of mucopolysaccharidosis type II (Hunter syndrome) by retroviral-mediated gene transfer and expression of human iduronate-2-sulfatase. Proc Natl Acad Sci 1993;90:11830-11834.
Brines, et al. Erythropoietin crosses the blood-brain barrier to protect against experimental brain injury, Proc Natl Acad Sci USA. 2000; 97:10526-10531.
Brummell, et al. Probing the combining site of an anti-carbohydrate antibody by saturation-mutagenesis: role of the heavy-chain CDR3 residues. Biochemistry. 1993; 32(4): 1180-7.
Buchli, et al. Inhibition of Nogo: a key strategy to increase regeneration, plasticity and functional recovery of the lesioned central nervous system. Ann Med. 2005;37(8):556-67.
Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

(56) References Cited

OTHER PUBLICATIONS

Byrn, et al. Biological properties of a CD4 immunoadhesin. Nature. Apr. 12, 1990;344(6267):667-70.
Carnicella, et al. GDNF is a fast-acting potent inhibitor of alcohol consumption and relapse. Proc Natl Acad Sci U S A. Jun. 10, 2008;105(23):8114-9.
Casset, et al. A peptide mimetic of an anti-CD4 monoclonal antibody by rational design. Biochem Biophys Res Commun. Jul. 18, 2003;307(1):198-205.
Cassol et al. Stability of dried blood spot specimens for detection of human immunodeficiency virus DNA by polymerase chain reaction. J Clin Microbiol. 30(12):3039-3042 (1992).
Chamow, et al. Immunoadhesins: principles and applications. Trends Biotechnol. Feb. 1996;14(2):52-60.
Chen, et al. Cotranslational folding and calnexin binding during glycoprotein synthesis. Proc Natl Acad Sci U S A. Jul. 3, 1995;92(14):6229-33.
Chen et al. Enhancement and destruction of antibody function U by somatic mutation: unequal occurrence is controlled by V gene combinatorial associations. The EMBO Journal 14(12):2784-2794 (1995).
Chen, et al. In vitro scanning saturation mutagenesis of all the specificity determining residues in an antibody binding site. Protein Engineering. 1999; vol. 12, No. 4, 349-56.
Cheng, et al. 1997. Marked Age-dependent Neuroprotection by Brain-derived Neurotropic Factor Against Neonatal Hypoxic-Ischemic Brain Injury. Annals of Neurology 41 (4): 521-29.
Cheng, et al. 2004. Neuroprotection for Ischemic Stroke: Two Decades of Success and Failure. The Journal of the American Society for Experimental Neuro Therapeutics 1: 36-45.
"Cheng, Sh et al. Gene therapy progress and prospects: gene therapy of lysosomal storage disorders, Gene Therapy 10:1275-1281 (2003)".
Chothia et al. Canonical structures for the hypervariable regions of immunoglobulins. J Mol Biol. 196(4):901-917 (1987).
Christian, et al. The distribution of D2/D3 receptor binding in the adolescent rhesus monkey using small animal PET imaging. Neuroimage. Feb. 15, 2009;44(4):1334-44. doi: 10.1016/j.neuroimage.2008.10.020. Epub Oct. 29, 2008.
Chudler, Eric H.Brain Facts and Figures, from Eric H. Chudler's Neuroscience for Kids: faculty.washington.edu/chudler/facts.html. Retreived from Internet on Jun. 6, 2016, 14 pages.
Chung et al. Antibodies against West Nile Virus nonstructural protein NS1 prevent lethal infection through Fc gamma receptor-dependent and-independent mechanisms. J Virol. Feb. 2006;80(3):1340-51.
Clements, et al. Human alpha-L-iduronidase. 1. Purification, monoclonal antibody production, native and subunit molecular mass. Eur J Biochem. Oct. 1, 1985;152(1):21-8.
Clements, et al. Immunopurification and characterization of human alpha-L-iduronidase with the use of monoclonal antibodies. Biochem J. Apr. 1, 1989;259(1):199-208.
Colman et al. Effects of amino acid sequence changes on antibody-antigen interactions. Research in Immunology 145(1):33-36 (1994).
Coloma, et al. 1997. Design and production of novel tetravalent bispecific antibodies. Nat Biotechnol Feb;15(2):159-63.
Coloma, et al. 1999. Transport Across the Primate Blood-Brain Barrier of a Genetically Engineered Chimeric Monoclonal Antibody to the Human Insulin Receptor. Pharmaceutical Research 17 (3): 266-274.
Coloma, et al. The hinge as a spacer contributes to covalent assembly and is required for function of IgG. J Immunol. Jan. 15, 1997;158(2):733-40.
Corchero, et al. The position of the heterologous domain can influence the solubility and proteolysis of beta-galactosidase fusion proteins in E. coli. J Biotechnol. Jul. 31, 1996;48(3):191-200.
Cosma, et al. The multiple sulfatase deficiency gene encodes an essential and limiting factor for the activity of sulfatases. Cell. May 16, 2003;113(4):445-56.
Cowen, et al. 2004. Neuropeptides: implications for alcoholism. Journal of Neurochemistry 89: 273-85.
Crow, et al. Biochemical and histopathological studies on patients with mucopolysaccharidoses, two of whom had been treated by fibroblast transplantation. J Clin Pathol. 1983:36(4):415-30.
Dawson, et al. A comparative assessment of the efficacy and side-effect liability of the neuroprotective compounds in experimental stroke. 2001. Brain Research 892: 344-50.
De Graaf, M. et al., "Expression of scFvs and scFv Fusion Proteins in Eukaryotic Cells." Mol. Biol. 2002; 178:379-387.
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Deakin, et al. Enzymatically active paraoxonase-1 is located at the external membrane of producing cells and released by a high affinity, saturable, desorption mechanism. J Biol Chem. Feb. 8, 2002;277(6):4301-8. Epub Nov. 28, 2001.
Deane, et al. IgG-assisted age-dependent clearance of Alzheimer's amyloid beta peptide by the blood-brain barrier neonatal Fc receptor. J Neurosci. 2005; 25(50):11495-503.
Deguchi, et al. Retention of biologic activity of human epidermal growth factor following conjugation to a blood-brain barrier drug delivery vector via an extended poly(ethylene glycol) linker. Bioconjug Chem. Jan.-Feb. 1999;10(1):32-7.
Dierks, et al. Conversion of cysteine to formylglycine in eukaryotic sulfatases occurs by a common mechanism in the endoplasmic reticulum. FEBS Lett. Feb. 13, 1998;423(1):61-5.
Dierks, et al. Sequence determinants directing conversion of cysteine to formylglycine in eukaryotic sulfatases. EMBO J. Apr. 15, 1999;18(8):2084-91.
Dreier, et al. Recombinant immunocytokines targeting the mouse transferrin receptor: construction and biological activities. Bioconjug Chem. Jul.-Aug. 1998;9(4):482-9.
Duchnowska, et al. Central nervous system metastases in breast cancer patients administered trastuzumab. Cancer Treat Rev. Jun. 2005;31(4):312-8.
Duffy, et al. 1987. Blood-brain barrier transcytosis of insulin in developing rabbits. Brain Research 420: 32-38.
Duffy et al., Human blood-brain barrier insulin-like growth factor receptor. Metabolism 37(2):136-40 (1988).
Durrington, et al. Paraoxonase and atherosclerosis. Arterioscler Thromb Vasc Biol. Apr. 2001;21(4):473-80.
Edwards et al. The remarkable flexibility of the human antibody repertoire; isolation of over one thousand different antibodies to a single protein. BLyS.J Mol Biol. 334(1):103-18 (2003).
Ehrenreich, et al. Erythropoetin therapy for acute stroke is both safe and beneficial. Mol Med. Aug. 2002;8(8):495-505.
Eketjall, et al. Distinct structural elements in GDNF mediate binding to GFRalpha1 and activation of the GFRalpha1-c-Ret receptor complex. EMBO J. Nov. 1, 1999;18(21):5901-10.
Elliott, et al. Control of rHuEPO biological activity: the role of carbohydrate. Exp Hematol. Dec. 2004;32(12):1146-55.
EP06825389.7 Search Report dated Feb. 23, 2010.
EP07841110.5 Search Report and opinion dated Dec. 2, 2010.
EP08796594.3 Search Report and opinion dated Mar. 16, 2012.
Eslamboli, et al. Continuous Low-Level Glial Cell Line-Derived Neurotrophic Factor Delivery Using Recombinant Adeno-Associated Viral Vectors Provides Neuroprotection and Induces Behavioral Recovery in a Primate Model of Parkinson's Disease. J. Neurosci. 2005:25:769-77.
European Application No. 16171496 Extended European Search Report dated Oct. 31, 2016.
European Application No. 16171496.9 Extended European Search Report dated Feb. 10, 2017.
European Patent Application No. 19150184 Extended European Search Report dated Dec. 13, 2019.
European search report and search opinion dated Sep. 21, 2015 for EP Application No. 12854380.8.
European search report and search opinion dated Dec. 20, 2012 for EP Application No. 10754139.
European search report dated Mar. 1, 2013 for EP Application No. 10822810.7.
European search report dated Jul. 15, 2013 for EP Application No. 11733492.

(56) References Cited

OTHER PUBLICATIONS

Ferber, D. Bridging the blood-brain barrier: new methods improve the odds of getting drugs to the brain cells that need them. PLoS Biol. Jun. 2007;5(6):e169: 1191-1194.
Fillebeen et al. Receptor-mediated transcytosis of lactoferrin through the blood-brain barrier. J Biol Chem. 274(11):7011-17 (1999).
Flomen, et al. Determination of the organisation of coding sequences within the iduronate sulphate sulphatase (IDS)gene. Hum. Mol. Genet. 1993;2(1):5-10.
Forough, et al. Differential transforming abilities of non-secreted and secreted forms of human fibroblast growth factor-1. J Biol Chem. Feb. 5, 1993;268(4):2960-8.
Fraldi, et al. Functional correction of CNS lesions in an MPS-IIIA mouse model by intracerebral AAV-mediated delivery of sulfamidase and SUMF1 genes. Hum Mol Genet. Nov. 15, 2007; 16(22):2693-702. Epub Aug. 27, 2007.
Franco, et al. A cluster of sulfatase genes on Xp22.3: mutations in chondrodysplasia punctata (CDPX) and implications for warfarin embryopathy. Cell. Apr. 7, 1995;81(1):15-25.
Frenkel, et al. Modulation of Alzheimer's beta-amyloid neurotoxicity by site-directed single-chain antibody. J Neuroimmunol. Jul. 1, 2000;106(1-2):23-31.
Friden, et al. Blood-brain barrier penetration and in vivo activity of an NGF conjugate. Science. Jan. 15, 1993;259(5093):373-77.
Fu, et al. Neuroprotection in stroke in the mouse with intravenous erythropoietin-Trojan horse fusion protein. Brain Res. Jan. 19, 2011;1369:203-7. Epub Oct. 31, 2010.
Fukuchi, et al. Amelioration of amyloid load by anti-Abeta single-chain antibody in Alzheimer mouse model. Biochem Biophys Res Commun. May 26, 2006;344(1):79-86.
Fukuda et al. In vitro evolution of single-chain antibodies using mRNA display. Nucleic Acids Research, 2006; 34(19):e127.
Gehrmann, et al. Biochemical properties of recombinant human beta-glucuronidase synthesized in baby hamster kidney cells. Biochem J. Aug. 1, 1994;301 (Pt3):821-8.
Genbank, anti-human CD40 12B4 chimeric kappa chain [synthetic construct]. ALO70203.1.
Gennaro, 2000. Remington: The Science and Practice of Pharmacy. 20 ed. (WAS: Remington's Pharmaceutical Sciences, Gennaro, AR, ed., 20th edition, 2000: Williams and Wilkins PA, USA).
Gillies, et al. Bi-functional cytokine fusion proteins for gene therapy and antibody-targeted tratment of cancer. 2002, Cancer Immunology and Immunotherapy, vol. 51, pp. 449-460.
Golden et al., Human blood-brain barrier leptin receptor. Binding and endocytosis in isolated human brain microvessels. J. Clin. Invest. 99(1):14-8 (1997).
Gonzales, et al. Minimizing immunogenicity of the SDR-grafted humanized antibody CC49 by genetic manipulation of the framework residues. Mol Immunol. Oct. 2003;40(6):337-49.
Gonzales, et al. SDR grafting of a murine antibody using multiple human germline templates to minimize its immunogenicity. Mol Immunol. Jul. 2004;41(9):863-72.
Grasso, et al. Neuroprotection by erythropoietin administration after experimental traumatic brain injury. Brain Res. Nov. 28, 2007:1182:99-105.
Green-Sadan, et al. Transplantation of glial cell line-derived neurotrophic factor-expressing cells into the striatum and nucleus accumbens attenuates acquisition of cocaine self-administration in rats. Eur J Neurosci. Oct. 2003:18(7):2093-8.
Habgood, et al. Changes in blood-brain barrier permeability to large and small molecules following traumatic brain injury in mice. Eur J Neurosci. Jan. 2007;25(1):231-8.
Haisma, et al. Construction and characterization of a fusion protein of single-chain anti-CD20 antibody and human beta-glucuronidase for antibody-directed enzyme prodrug therapy. Blood. Jul. 1, 1998;92(1):184-90.
Hansson et al. Prediction of Alzheimer's disease using the CSF Abeta42/Abeta40 ratio in patients with mild cognitive impairment. Dement Geriatr Cogn Disord. 2007;23(5):316-20.

He, et al. Autoregulation of glial cell line-derived neurotrophic factor expression: implications for the long-lasting actions of the anti-addiction drug, Ibogaine. FASEB J. Nov. 2006;20(13):E1820-E1827; 2420-22.
He, et al. Glial cell line-derived neurotrophic factor mediates the desirable actions of the anti-addiction drug ibogaine against alcohol consumption. J Neurosci. Jan. 19, 2005;25(3):619-28.
He, et al. Identification and characterization of the molecular lesion causing mucopolysaccharidosis type I in cats. Mol Genet Metab. 1999; 67(2):106-12.
Henikoff et al. Amino acid substitution matrices from protein blocks. PNAS USA 89(22):10915-10919 (1992).
Henikoff, et al. Predicting the effects of amino Acid substitutions on protein function. Annu Rev Genomics Hum Genet. 2006;7:61-80.
Hetman, et al. Neuroprotection by Brain-derived Neurotropic Factor Is Mediated by Extracellular Signal-regulated Kinase and Phoshatidylinositol 3-Kinase. The J of Bio Chem. 1999. 274 (32): 22569-80.
Holliger, et al. Engineered antibody fragments and the rise of single domains. Nat Biotechnol. Sep. 2005;23(9):1126-36.
Hoshaw, et al. Central administration of IGF-I and BDNF leads to long-lasting antidepressant-like effects. Brain Res. 2005. 1037: 204-8.
Hui et al., "Tumor Necrosis Factor Receptor-IgG Fusion Protein for Targeted Drug Delivery across the Human Blood-Brain Barrier," Mol. Pharm. vol. 6, No. 5, pp. 1536-1543 (2009).
Huston et al. Protein engineering of antibody binding sites: recovery of specific activity in an anti-digoxin single-chain Fv analogue produced in *Escherichia coli*. PNAS USA 85(16):5879-5883 (1988).
Ibanez et al. An extended surface of binding to Trk tyrosine kinase receptors in NGF and BDNF allows the engineering of a multi-functional pan-neurotrophin. EMBO J 12(6):2281-2293 (1993).
Ibanez, Structure-function relationships in the neurotrophin family. J Neurobiol. Nov. 1994;25(11):1349-61.
International Preliminary Report on Patentability and Written Opinion for International Application No. PCT/US2014/047082 dated Jan. 19, 2016.
International Preliminary Report on Patentability and Written Opinion dated Jan. 26, 2016 in PCT/US2014/038660.
International Preliminary Report on Patentability dated Jun. 1, 2010 for PCT/US2008/084718.
International search report and written opinion dated Feb. 22, 2011 for PCT/US2010/052113.
International search report and written opinion dated Feb. 22, 2013 for PCT/US2012/054520.
International search report and written opinion dated Feb. 27, 2009 for PCT/US2008/071121.
International search report and written opinion dated Apr. 8, 2011 for PCT/US2011/21418.
International search report and written opinion dated Jul. 1, 2008 for PCT/US2006/038587.
International search report and written opinion dated Sep. 7, 2010 for PCT/US2010/027882.
International search report and written opinion dated Sep. 16, 2008 for PCT/US2007/076316.
International search report and written opinion dated Oct. 29, 2014 for PCT/US2014/038660.
International search report and written opinion dated Dec. 15, 2014 for PCT Application No. PCT/US2014/047082.
Iwasaki, et al. Protective effect of interleukin-3 and erythropoietin on motor neuron death after neonatal axotomy. Neurol Res. Oct. 2002;24(7):643-6.
Jefferies, et al. Analysis of lymphopoietic stem cells with a monoclonal antibody to the rat transferrin receptor. Immunology. Feb. 1985;54(2):333-41.
Jeffrey, et al. 26-10 Fab-digoxin complex: Affinity and specificity due to surface complementarity. Proc Natl. Acad. Sci USA. 1993; 90(21):10310-10314.
Jethwa, et al. 2005. Neuromedin U has a physiological role in the regulation of food intake and partially mediates the effects of leptin. American Journal of Physiology- Endocrinology and Metabolism 289: E301-E305.

(56) References Cited

OTHER PUBLICATIONS

Jiang, et al. BDNF Variation and Mood Disorders: A Novel Functional Promoter Polymorphism and Val66Met are Associated with Anxiety but Have Opposing Effects. 2005. Neuropsychopharmacology 30:1353-61.

Jiang, et al. A genetic fusion construct between the tetanus toxin C fragment and the lysosomal acid hydrolase beta-glucuronidase expresses a bifunctional protein with enhanced secretion and neuronal uptake. J Neurochem. Jun. 2005;93(5):1334-44.

Jones, et al. Determination of Tumor Necrosis Factor Binding Protein Disulfide Structure: Deviation of the Fourth Domain Structure from the TNFR/NGFR Family Cysteine-Rich Region Signature Biochemistry. 1997; 36: 14914-23.

Josse, et al. Identification of residues essential for human paraoxonase (PON1) arylesterase/organophosphatase activities. Biochemistry. Mar. 2, 1999;38(9):2816-25.

Josse, et al. Oligomeric states of the detergent-solubilized human serum paraoxonase (PON1). J Biol Chem. Sep. 6, 2002;277(36):33386-97.

Josse, et al. The active site of human paraoxonase (PON1). J Appl Toxicol. Dec. 2001;21 Suppl 1:S7-11.

Juul, et al. Erythropoietin concentrations in cerebrospinal fluid of nonhuman primates and fetal sheep following high-dose recombinant erythropoietin, Biol. Neonate. 2004;85:138-144.

Kabat et al. Sequences of Proteins of Immunological Interest. NIH Pub. No. 91-3242. Public Health Service, National Institutes of Health. 1:647-669 (1991).

Kakkis, et al. Intrathecal enzyme replacement therapy reduces lysosomal storage in the brain and meninges of the canine model of MPS I. Mol Genet Metab. Sep.-Oct. 2004;83(1-2):163-74.

Kakkis, et al. Overexpression of the human lysosomal enzyme alpha-L-iduronidase in Chinese hamster ovary cells. Protein Expr Purif. 1994; 5(3):225-32.

Karlin, et al. Applications and statistics for multiple high-scoring segments in molecular sequences. PNAS USA 90:5873-5877 (1993).

Kashmiri, et al. SDR grafting—a new approach to antibody humanization. Methods. May 2005;36(1):25-34.

Kastin, et al. Glial cell line-derived neurotrophic factor does not enter normal mouse brain. Neuroscience Letters. 2003;340:239-41.

Kido, et al. 2000. Neuroprotective effects of brain-derived neurotropic factor in eyes with NMDA-induced neuronal death. Brain Research 884:59-67.

Kim, et al., Continuous Brain-derived Neurotropic Factor (BDNF) Infusion After Methylprednisolone Treatment in Severe Spinal Cord Injury. Journal of Korean Medical Science 2004;19: 113-22.

Kim, et al. Decreased paraoxonase-1 activity is a risk factor for ischemic stroke in Koreans. Biochem Biophys Res Commun. Dec. 7, 2007;364(1):157-62.

Kim, et al. N-terminal domains of native multidomain proteins have the potential to assist de novo folding of their downstream domains in vivo by acting as solubility enhancers. Protein Sci. Apr. 2007;16(4):635-43.

Kim et al. Protective effects of glial cell line-derived neurotrophic factor on hippocampal neurons after traumatic brain injury in rats. Journal of Neurosurgery 95:674-679 (2001).

Kitagawa, et al. Reduction of Ischemic Brain Injury by Topical Application of Glial Cell Line-Derived Neurotrophic Factor After Permanent Middle Cerebral Artery Occlusion in Rats. Stroke. 1998;29:1417-22.

Knaust, "Residues Critical for Formylglycine Formation and/or Catalytic Activity of Arylsulfatase A," Biochemistry, 37:13941-13946 (1998).

Kobayashi, et al. Intracerebral Infusion of Glial Cell Line-Derived Neurotrophic Factor Promotes Striatal Neurogenesis After Stroke in Adult Rats Stroke. 2006;37:2361-67.

Koehne, et al. Vascular endothelial growth factor and erythropoietin concentrations in cerebrospinal fluid of children with hydrocephalus. Childs Nerv Syst. Apr. 2002;18(3-4):137-41.

Krewson, et al. Distribution of nerve growth factor following direct delivery to brain interstitium. Brain Research 680: 196-206 (1995).

Kurbacher, et al. Continuous Low-Dose GM-CSF as Salvage Therapy in Refractory Recurrent Breast or Female Genital Tract Carcinoma. Oncology, 19(4) Supp 2: 23-26 (Apr. 2005).

Kurihara, et al. Imaging Brain Tumors by Targeting Peptide Radiopharmaceuticals through the Blood-Brain Barrier. Cancer Research 59: 6159-63 (1999).

Kussie, et al. A single engineered amino acid substitution changes antibody fine specificity. J Immunol. Jan. 1, 1994;152(1):146-52.

Lai, et al. Structural determinants of Trk receptor specificities using BDNF-based neurotrophin chimeras. J Neurosci Res. Dec. 1, 1996;46(5):618-29.

Lang, et al. Randomized controlled trial of intraputamenal glial cell line-derived neurotrophic factor infusion in Parkinson disease. Annals of Neurology. 2006;59:459-66.

Lapchak, et al. Glial cell line-derived neurotrophic factor attenuates behavioural deficits and regulates nigrostriatal dopaminergic and peptidergic markers in 6-hydroxydopamine-lesioned adult rats: comparison of intraventricular and intranigral delivery. Neuroscience. 1997;78:61-72.

Lappi, et al. Expression and activities of a recombinant basic fibroblast growth factor-saporin fusion protein. J Biol Chem. Apr. 29, 1994;269(17):12552-8.

Lazar, et al. Transforming growth factor alpha: mutation of aspartic acid 47 and leucine 48 results in different biological activities. Mol Cell Biol. Mar. 1988;8(3):1247-52.

Lee, et al. Drug targeting to the brain using avidin-biotin technology in the mouse; (blood-brain barrier, monoclonal antibody, transferrin receptor, Alzheimer's disease). J Drug Target. 2000;8(6):413-24.

Lee, et al., Imaging Brain Amyloid of Alzheimer Disease In Vivo in Transgenic Mice With an Aβ Peptide Radiopharmaceutical. Journal of Cerebral Blood Flow and Metabolism 2002;22: 223-31.

Lenz, et al. Stoichiometric and catalytic scavengers as protection against nerve agent toxicity: a mini review. Toxicology. Apr. 20, 2007;233(1-3):31-9.

Lewin, B. Genes IV. Oxford University Press. 1990. p. 810.

Li, et al. Genetically engineered brain drug delivery vectors: cloning, expression and in vivo application of an anti-transferrin receptor single chain antibody-streptavidin fusion gene and protein. Protein Eng. Sep. 1999;12(9):787-96.

Lin, et al. GDNF: a glial cell line-derived neurotrophic factor for midbrain dopaminergic neurons. Science. 1993;260:1130-32.

Lin, et al. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.

Liu, et al. Anti beta-amyloid (Abeta) SCFV inhibits Abeta aggregation and neurotoxicity (P4-354). Neurobiology of Aging, Tarrytown, NY. 2004;25:S575-S576.

Liu, et al. Single chain variable fragments against beta-amyloid (Abeta) can inhibit Abeta aggregation and prevent abeta-induced neurotoxicity. Biochemistry. Jun. 8, 2004;43(22):6959-67.

Lu, et al. Cationic Liposome-Mediated GDNF Gene Transfer after Spinal Cord Injury. Journal of Neurotrauma. 2002;19:1081-1090.

Lu et al., "Expression in CHO Cells and Pharmacokinetics and Brain Uptake in the Rhesus Monkey of an IgG-Iduronate-2-Sulfatase Fusion Protein," Biotechnology and Bioengineering, vol. 108, No. 8, pp. 1954-1964 (2011).

Lu et al., "Genetic Engineering of a Bifunctional IgG fusion protein with iduronate-2-sulfatase," Bioconjugate Chemistry, 21(1) pp. 151-156 (2010).

Lukatela, et al. Crystal structure of human arylsulfatase A: the aldehyde function and the metal ion at the active site suggest a novel mechanism for sulfate ester hydrolysis. Biochemistry. Mar. 17, 1998;37(11):3654-64.

Ma, et al. Erythropoietin protects PC12 cells from beta-amyloid(25-35)-induced apoptosis via PI3K/Akt signaling pathway. Neuropharmacology. May-Jun. 2009;56(6-7):1027-34.

MacCallum et al. Antibody-antigen interactions: contact analysis and binding site topography. J Mol Biol. 262(5):732-745 (1996).

Manoutcharian, et al. Amyloid-beta peptide-specific single chain Fv antibodies isolated from an immune phage display library. J Neuroimmunol. 2003; 145(1-2):12-7.

(56) References Cited

OTHER PUBLICATIONS

Martell, et al. Efficacy of transferrin receptor-targeted immunotoxins in brain tumor cell lines and pediatric brain tumors. Cancer Res. Mar. 15, 1993;53(6):1348-53.
Martin et al. Crystal structure at 2.8 A of an FcRn/heterodimeric Fc complex: mechanism of pH-dependent binding. Mol Cell. Apr. 2001;7(4):867-77.
Marvin, et al. Recombinant approaches to IgG-like bispecific antibodies. Acta Pharmacol Sin. Jun. 2005;26(6):649-58.
Matis, et al. Erythropoietin in spinal cord injury. Eur Spine J. Mar. 2009;18(3):314-23.
McGrath, et al. Bifunctional fusion between nerve growth factor and a transferrin receptor antibody. J Neurosci Res. Jan. 15, 1997;47(2):123-33.
McLendon et al. Radiotoxicity of systemically administered 211At-labeled human/mouse chimeric monoclonal antibody: a long-term survival study with histologic analysis. Int J Radiat Oncol Biol Phys. Sep. 1, 1999;45(2):491-9.
Menzies, et al. Contributions of ions and albumin to the formations and resolution of ischemic brain edema. Journal of Neurosurgery 78: 257-266. (1993).
Messer, et al. Role for GDNF in biochemical and behavioral adaptations to drugs of abuse. Neuron. Apr. 2000;26(1):247-57.
Moos, et al. Restricted transport of anti-transferrin receptor antibody (OX26) through the blood-brain barrier in the rat. J Neurochem. Oct. 2001;79(1):119-29.
Mori, et al. Differential expression patterns of TrkB ligands in the macaque monkey brain. Developmental Neuroscience 15: 2507-11 (2004).
Morita, et al. Association of tumor necrosis factor receptor type II polymorphism 196R with Systemic lupus erythematosus in the Japanese: molecular and functional analysis. Arthritis Rheum. Dec. 2001;44(12):2819-27.
Muenzer, et al. A phase II/III clinical study of enzyme replacement therapy with idursulfase in mucopolysaccharidosis II (Hunter syndrome). Genet Med Aug. 2006;8(8):465-73.
Muenzer, et al. Advances in the treatment of mucopolysaccharidosis type I. N Engl J Med. May 6, 2004;350(19):1932-4.
Nawashiro et al., "Neuroprotective effects of TNF binding protein in focal cerebral ischemia," Brain Research, vol. 778, No. 2, pp. 265-271 (1997).
NCBI GenBank Accession No. NM-000487 (Oct. 23, 2011).
NCBI Reference Sequence: NM-000202.5 Homo sapiens iduronate 2-sulfatase (IDS), transcript variant 1, mRNA. 1992. http://www.ncbi.nlm.nih.gov/nuccore/NM000202.5.
Needleman et al. A general method applicable to the search for similarities in the amino acid sequence of two proteins. J. Mol. Biol. 48:443-453 (1970).
Ng, et al. Paraoxonase-1 deficiency in mice predisposes to vascular inflammation, oxidative stress, and thrombogenicity in the absence of hyperlipidemia. Cardiovasc Pathol. Jul.-Aug. 2008;17(4):226-32.
Ng, et al. Predicting the effects of amino acid substitutions on protein function. Annual Review of Genomics and Human Genetics. 2006;7:61-80.
Notice of allowance dated Jan. 22, 2014 for U.S. Appl. No. 12/323,232.
Notice of allowance dated Jan. 28, 2010 for U.S. Appl. No. 11/841,623.
Notice of Allowance dated Mar. 20, 2013 for U.S. Appl. No. 13/609,099.
Notice of allowance dated Apr. 1, 2011 for U.S. Appl. No. 11/245,546.
Notice of Allowance dated Apr. 2, 2013 for U.S. Appl. No. 11/841,594.
Notice of allowance dated May 20, 2014 for U.S. Appl. No. 12/901,481.
Notice of allowance dated Aug. 9, 2011 for U.S. Appl. No. 11/245,710.
Notice of allowance dated Aug. 12, 2014 for U.S. Appl. No. 14/194,463.
Notice of allowance dated Sep. 23, 2013 for U.S. Appl. No. 12/756,093.
Notice of allowance dated Sep. 25, 2013 for U.S. Appl. No. 13/862,250.
Notice of allowance dated Oct. 7, 2013 for U.S. Appl. No. 12/323,232.
Notice of allowance dated Oct. 28, 2011 for U.S. Appl. No. 12/688,842.
Notice of allowance dated Oct. 31, 2011 for U.S. Appl. No. 11/245,546.
Notice of allowance dated Dec. 13, 2013 for U.S. Appl. No. 13/862,250.
Notice of allowance dated Dec. 16, 2013 for U.S. Appl. No. 12/756,093.
Notice of allowance dated Dec. 19, 2014 for U.S. Appl. No. 12/179,806.
Notice of allowance dated Dec. 23, 2013 for U.S. Appl. No. 11/841,541.
Nutt et al. Randomized, double-blind trial of glial cell line-derived neurotrophic factor (GDNF) in PD. Neurology 60:69-73 (2003).
Ober, et al. Differences in promiscuity for antibody-FcRn interactions across species: implications for therapeutic antibodies. Int Immunol. Dec. 2001;13(12):1551-9.
Office action dated Jan. 9, 2013 for U.S. Appl. No. 12/901,481.
Office action dated Jan. 10, 2019 for U.S. Appl. No. 14/144,460.
Office action dated Jan. 15, 2008 for U.S. Appl. No. 11/245,710.
Office action dated Jan. 15, 2009 for U.S. Appl. No. 11/841,623.
Office action dated Jan. 23, 2009 for U.S. Appl. No. 11/245,546.
Office action dated Feb. 2, 2010 for U.S. Appl. No. 11/245,710.
Office action dated Feb. 10, 2006 for U.S. Appl. No. 10/307,165.
Office action dated Feb. 16, 2011 for U.S. Appl. No. 11/893,281.
Office action dated Feb. 16, 2011 for U.S. Appl. No. 12/150,983.
Office action dated Feb. 22, 2006 for U.S. Appl. No. 10/307,276.
Office action dated Mar. 1, 2007 for U.S. Appl. No. 10/307,165.
Office action dated Mar. 7, 2011 for U.S. Appl. No. 12/558,348.
Office action dated Mar. 10, 2010 for U.S. Appl. No. 12/179,806.
Office action dated Mar. 18, 2011 for U.S. Appl. No. 12/574,571.
Office action dated Mar. 26, 2010 for U.S. Appl. No. 11/841,594.
Office action dated Mar. 26, 2010 for U.S. Appl. No. 12/323,232.
Office action dated Apr. 6, 2011 for U.S. Appl. No. 11/245,710.
Office action dated Apr. 8, 2014 for U.S. Appl. No. 13/141,682.
Office action dated Apr. 9, 2007 for U.S. Appl. No. 10/307,276.
Office action dated Apr. 13, 2007 for U.S. Appl. No. 11/245,710.
Office action dated Apr. 24, 2013 for U.S. Appl. No. 12/179,806.
Office action dated May 6, 2014 for U.S. Appl. No. 14/144,460.
Office action dated May 6, 2015 for U.S. Appl. No. 14/281,803.
Office action dated May 9, 2008 for U.S. Appl. No. 11/061,956.
Office action dated May 12, 2010 for U.S. Appl. No. 11/893,281.
Office action dated May 13, 2011 for U.S. Appl. No. 12/688,842.
"Office action dated May 19, 2015 for U.S. Appl. No. 13/141,682.".
Office action dated May 23, 2006 for U.S. Appl. No. 11/061,956.
Office action dated Jun. 3, 2008 for U.S. Appl. No. 11/245,710.
Office action dated Jun. 17, 2009 for U.S. Appl. No. 11/841,541.
Office action dated Jun. 27, 2011 for U.S. Appl. No. 11/245,546.
Office action dated Jun. 30, 2014 for U.S. Appl. No. 12/179,806.
Office action dated Jul. 1, 2010 for U.S. Appl. No. 11/245,546.
Office action dated Jul. 2, 2008 for U.S. Appl. No. 11/245,546.
Office action dated Jul. 2, 2009 for U.S. Appl. No. 11/245,710.
Office action dated Jul. 19, 2006 for U.S. Appl. No. 10/307,276.
Office action dated Jul. 20, 2012 for U.S. Appl. No. 12/756,093.
Office action dated Jul. 31, 2009 for U.S. Appl. No. 12/179,806.
Office action dated Aug. 15, 2013 for U.S. Appl. No. 13/141,682.
Office action dated Aug. 17, 2007 for U.S. Appl. No. 10/307,165.
Office action dated Aug. 18, 2006 for U.S. Appl. No. 10/307,165.
Office action dated Aug. 20, 2009 for U.S. Appl. No. 12/323,232.
Office action dated Sep. 15, 2010 for U.S. Appl. No. 12/150,983.
Office action dated Sep. 20, 2007 for U.S. Appl. No. 11/245,710.
Office action dated Sep. 24, 2009 for U.S. Appl. No. 11/841,623.
Office action dated Oct. 12, 2010 for U.S. Appl. No. 11/245,710.
Office action dated Oct. 13, 2009 for U.S. Appl. No. 11/893,281.
Office action dated Oct. 15, 2007 for U.S. Appl. No. 11/245,710.
Office action dated Oct. 18, 2011 for U.S. Appl. No. 11/245,546.
Office action dated Oct. 20, 2009 for U.S. Appl. No. 11/245,546.
Office action dated Oct. 20, 2014 for U.S. Appl. No. 13/141,682.
Office action dated Oct. 22, 2013 for U.S. Appl. No. 12/901,481.
Office action dated Oct. 29, 2007 for U.S. Appl. No. 10/307,276.

(56) References Cited

OTHER PUBLICATIONS

Office action dated Oct. 30, 2009 for U.S. Appl. No. 11/841,594.
Office action dated Nov. 1, 2012 for U.S. Appl. No. 11/841,594.
Office action dated Nov. 4, 2013 for U.S. Appl. No. 12/179,806.
Office action dated Nov. 8, 2007 for U.S. Appl. No. 11/245,546.
Office action dated Nov. 10, 2008 for U.S. Appl. No. 11/245,710.
Office action dated Nov. 13, 2006 for U.S. Appl. No. 11/245,710.
Office action dated Nov. 13, 2007 for U.S. Appl. No. 11/061,956.
Office action dated Nov. 26, 2012 for U.S. Appl. No. 13/609,099.
Office action dated Nov. 26, 2014 for U.S. Appl. No. 14/144,460.
Office action dated Dec. 14, 2011 for U.S. Appl. No. 12/574,571.
Office action dated Dec. 16, 2009 for U.S. Appl. No. 11/841,541.
Office action dated Dec. 21, 2006 for U.S. Appl. No. 11/061,956.
Office action dated Mar. 26, 2013 for U.S. Appl. No. 11/841,541.
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Orcutt, et al. A modular IgG-scFv bispecific antibody topology. Protein Eng Des Sel. Apr. 2010;23(4):221-8. doi: 10.1093/protein/gzp077. Epub Dec. 17, 2009.
Osbourn, et al. Directed selection of MIP-1 alpha neutralizing CCR5 antibodies from a phage display human antibody library. Nat Biotechnol. Aug. 1998;16(8):778-81.
Padlan, et al. Identification of specificity-determining residues in antibodies. FASEB J. 1995; 9(1):133-9.
Padlan, et al. Structure of an antibody-antigen complex: crystal structure of the HyHEL-10 Fab-lysozyme complex. Proc Natl Acad Sci U S A. Aug. 1989;86(15):5938-42.
Padridge, William M. Blood-brain drug targeting enables neuroprotection in brain ischemia following delayed intravenous administration of neurothrophins, Advances in Experimental Medicine and Biology, 543:397-430 (Jan. 1, 2002).
Pagel et al., Comparison of a tetravalent single-chain antibody-streptavidin fusion protein and an antibody-streptavidin chemical conjugate for pretargeted anti-CD20 radioimmunotherapy of B-cell lymphomas. Blood. 108(1): 328-336 (2006).
Paragh, et al. Ciprofibrate increases paraoxonase activity in patients with metabolic syndrome. Br J Clin Pharmacol. Jun. 2006;61(6):694-701.
Pardridge , Biopharmaceutical drug targeting to the brain. Journal of Drug Targeting, 18(3):157-167 (2010).
Pardridge, The Blood-Brain Barrier: Bottleneck in Brain Drug Development. NeuroRx: The Journal of the American Society for Experimental NeuroTherapeutics 2: 3-14 (2005).
Pardridge. "Blood-brain barrier delivery of protein and non-viral gene therapeutics with molecular Trojan horses," Journal of Controlled Release, vol. 122, No. 3, pp. 345-348 (2007).
Pardridge., Blood-Brain Barrier Drug Targeting: The Future of Brain Drug Development. Molecular Interventions, 3 (2003): 90-105.
Pardridge, Brain drug targeting: The future of brain drug development. Cambridge University Press (2001).
Pardridge, Drug Targeting to the Brain. Pharm Res 24:1733-44 (2007).
Pardridge, et al. Human insulin receptor monoclonal antibody undergoes high affinity binding to human brain capillaries in vitro and rapid transcytosis through the blood-brain barrier in vivo in the primate. Pharm Res. 12(6):807-16 (1995).
Pardridge et al., "Biologic TNF[alpha]-inhibitors that cross the human blood-brain barrier," Bioengineered Bugs. vol. 1, No. 4, pp. 231-234 (2010).
Pardridge, et al. Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. Pharmaceutical Research 15 (4): 576-582(1998).
Pardridge et al. Drug and gene targeting to the brain with molecular Trojan horses. Nat Rev Drug Discov., 1.2 (2002): 131-9.
Pardridge, et al. Drug Transport across the blood-brain barrier. Journal of Cerebral Blood Flow & Metabolism. 32; 1959-1972(2012).
Pardridge, et al. Human Blood-Brain Barrier Transferrin Receptor. Metabolism 36: 892-95 (1987).
Pardridge, et al. Transport of histone through the blood-brain barrier. J Pharmacol Exp Ther. Dec;251(3):821-6. (1989).
Pardridge, et al. Transport of Human Recombinant Brain-Derived Neurotrophic Factor (BDNF) Through the Rat Blood-Brain Barrier in Vivo Using Vector-Mediated Peptide Drug Delivery. Pharmaceutical Research 11 (5): 738-46 (1994).
Pardridge, Neuroprotection in stroke: is it time to consider large-molecule drugs? Drug Discovery Today 6: 751-53 (2001).
Pardridge, Neurotrophins, neuroprotection and the blood-brain barrier. Current Opinion in Investigational Drugs 3 (12): 1753-57 (2002).
Pardridge, "Re-engineering biopharmaceuticals for delivery to brain with molecular Trojan horses," Bioconjugate Chemistry, vol. 19, No. 7, pp. 1327-1338 (2008).
Pardridge, The Blood-Brain Barrier and Neurotherapeutics. NeuroRx: The Journal of the American Society for Experimental NeuroTherapeutics 2 (1): 1-2 (2005).
Pardridge, Tyrosine Hydroxylase Replacement in Experimental Parkinson's Disease with Transvascular Gene Therapy. NueuoRx: Journal of the American Society for Experimental NeuroTherapeutics. 2(1):129-138. (2005).
Park, et al. Production and characterization of fusion proteins containing transferrin and nerve growth factor. J Drug Target. 1998;6(1):53-64.
Patel, et al. Intraputamenal infusion of glial cell line-derived neurotrophic factor in PD: A two-year outcome study. Annals of Neurology. 2005;57:298-302.
Paul. Fundamental Immunology, 3rd Edition, Chapter 9, pp. 292-295 (1993).
PCT/US19/45547 International Search Report and Written Opinion dated Jan. 22, 2020.
PCT/US2019/045547 Invitation to Pay Additional Fees dated Oct. 29, 2019.
Pearson, et al. Improved Tools for Biological Sequence Comparison. Proc. Nat'l Acad. Sci. USA. 85 (1988): 2444-48.
Pearson, Rapid and sensitive sequence comparison with FASTP and FASTA. Meth. Enzymol. 1990;183:63-98.
Pencea, et al. Infusion of Brain-Derived Neurotrophic Factor into the Lateral Ventricle of the Adult Rat Leads to New Neurons in the Parenchyma of the Striatum, Septum, Thalamus, and Hypothalamus. The Journal of Neuroscience 2001 21 (17): 6706-17.
Penichet, et al. An antibody-avid in fusion protein specific for the transferrin receptor serves as a delivery vehicle for effective brain targeting: initial applications in anti-HIV antisense drug delivery to the brain. J Immunol. Oct. 15, 1999;163(8):4421-26.
Peppel; et al., "A tumor necrosis factor (TNF) receptor-IgG heavy chain chimeric protein as a bivalent antagonist of TNF activity.", J Exp Med, Dec. 1, 1991, 174(6), 1483-9.
Pluckthun. Chapter 11: Antibodies from *Escherichia coli*. In The Pharmacology of Monoclonal Antibodies. 113:269-315 (1994).
Polito et al., "IDS Crossing of the Blood-Brain Barrier Corrects CNS Defects in MPSII Mice," Amer. Journ. Human Genetics, vol. 85, No. 2, pp. 296-301 (2009).
Pregi, et al. TNF-alpha-induced apoptosis is prevented by erythropoietin treatment on SH-SY5Y cells. Exp Cell Res. Feb. 1, 2009;315(3):419-31. Epub Nov. 20, 2008.
Preston, et al. 1997. Evidence for pore-like opening of the blood-brain barrier following forebrain ischemia in rats. Brain Research 761: 4-10.
Prince, et al. Lipoprotein receptor binding, cellular uptake, and lysosomal delivery of fusions between the receptor-associated protein (RAP) and alpha-L-iduronidase or acid alpha-glucosidase. J Biol Chem. Aug. 13, 2004;279(33):35037-46. Epub May 31, 2004.
Qi, et al. Binding and cytotoxicity of conjugated and recombinant fusion proteins targeted to the gonadotropin-releasing hormone receptor. Cancer Res. Mar. 15, 2004;64(6):2090-5.
Raghavan, et al. Analysis of the pH dependence of the neonatal Fc receptor/immunoglobulin G interaction using antibody and receptor variants. Biochemistry. Nov. 14, 1995;34(45):14649-57.

(56) References Cited

OTHER PUBLICATIONS

Ratliff-Schaub, et al. 2005. Randomized controlled trial of transdermal secretion on behavior of children with autism. Autism 9 (3): 256-65.
Reiber, et al. Protein transfer at the blood cerebrospinal fluid barrier and the quantitation of the humoral immune response within the central nervous system. Clin Chim Acta. Mar. 30, 1987;163(3):319-28.
Rempel, et al. A homology model for human α-L-Iduronidase: Insights into human disease. Mol. Genetics and Met. 2005; 85:28-37.
Robinson, et al. The structures of the neurotrophin 4 homodimer and the brain-derived neurotrophic factor / neurotrophin 4 heterodimer reveal a common Trk-binding site. Protein Science 1999 8: 2589-97.
Rochu, et al. Human paraoxonase: a promising approach for pre-treatment and therapy of organophosphorus poisoning. Toxicology. Apr. 20, 2007;233(1-3):47-59.
Rohrback, et al. Therapeutic antibodies and antibody fusion proteins. Biotechnol Genet Eng Rev. 2003;20:137-63.
Rossolini et al. Use of deoxyinosine-containing primers vs degenerate primers for polymerase chain reaction based on ambiguous sequence information. Mol Cell Probes 8(2):91-98 (1994).
Rudikoff, et al. Single amino acid substitution altering antigen-binding specificity. Proc Natl Acad Sci U S A. Mar. 1982;79(6):1979-83.
Ruiz-Leon, et al. Induction of Tyrosine Kinase Receptor B by Retinoic Acid Allows Brain-Derived Neurotrophic Factor-Induced Amyloid Precursor Protein Gene Expression In Human SHSY5Y Neuroblastoma Cells. Neuroscience 120;2003:1019-26.
Ruth, et al. alpha-L-iduronidase forms semi-crystalline spherulites with amyloid-like properties. Acta Crystallogr D Biol Crystallogr. Apr. 2000;56(Pt 4):524-8.
Rybak, et al. Humanization of immunotoxins. Proc Natl Acad Sci U S A. Apr. 15, 1992;89(8):3165-9.
Sakanaka, et al. In vivo evidence that erythropoietin protects neurons from ischemic damage. Proc Natl Acad Sci U S A. Apr. 14, 1998;95(8):4635-40.
Sakane, et al. Carboxyl-directed Pegylation of Brain-derived Neurotrophic Factor Markedly Reduces Systemic Clearance with Minimal Loss of Biologic Activity. Pharmaceutical Research 1997 14(8):1085-1091.
Sampson et al. Unarmed, tumor-specific monoclonal antibody effectively treats brain tumors. Proc Natl Acad Sci U S A. Jun. 20, 2000;97(13):7503-8.
Sardiello, et al. Sulfatases and sulfatase modifying factors: an exclusive and promiscuous relationship. Hum Mol Genet. Nov. 1, 2005;14(21):3203-17. Epub Sep. 20, 2005.
Sariola, et al. Novel functions and signalling pathways for GDNF. J Cell Sci. Oct. 1, 2003;116(Pt 19):3855-62.
Scallon, et al. Functional comparisons of different tumour necrosis factor receptor/IgG fusion proteins. Cytokine. Nov. 1995;7(8):759-70.
Schabitz, et al. Intraventricular Brain-Derived Neurotrophic Factor Reduces Infarct Size After Focal Cerebral Ischemia in Rats. Journal of Cerebral Blood Flow and Metabolism 1997;17: 500-6.
Schlachetzki, et al. Expression of the neonatal Fc receptor (FcRn) at the blood-brain barrier. J Neurochem. Apr. 2002;81(1):203-6.
Schlachetzki, et al. Gene therapy of the brain: the trans-vascular approach. Neurology. Apr. 27, 2004;62(8):1275-81.
Schoonjans, R. et al., "Fab Chains As an Efficient Heterodimerization Scaffold for the Production of Recombinant Bispecific and Trispecific Antibody Derivatives." The Journal of Immunology, 2000, 165 (12): 7050-7057.
Schuchman, et al. Human alpha-L-iduronidase: Purification and properties of the high uptake (higher molecular weight) and the low uptake (processed) forms. J. Bioi. Chem. 1984; 259(5):3132-3140.
Schwartz, et al. A superactive insulin: [B10-aspartic acid]insulin(human). Proc Natl Acad Sci U S A. Sep. 1987;84(18):6408-11.
Scott, et al. Human alpha-L-iduronidase: cDNA isolation and expression. Proc Natl Acad Sci U S A. Nov. 1, 1991;88(21):9695-9.

Sellers, Peter H. On the theory and computation of evolutionary distances. SIAM Journal on Applied Mathematics. 1974;26:787.
Selmayr, et al. Induction of tumor immunity by autologous B lymphoma cells expressing a genetically engineered idiotype. Gene Ther. May 1999;6(5):778-84.
Sevin, C. et al. Intracerebral adeno-associated virus-mediated gene transfer in rapidly progressive forms of metachromatic leukodystrophy. Human Molecular Genetics 15(1); 53-64 (2006).
Shanafelt, et al. Identification of critical amino acid residues in human and mouse granulocyte-macrophage colony-stimulating factor and their involvement in species specificity. J Biol Chem. Jul. 25, 1991;266(21):13804-10.
Shin, et al. Transferrin-antibody fusion proteins are effective in brain targeting, Proceedings of the Natinal Academy of Sciences, 1995. vol. 92, pp. 2820-2824.
Shipley, et al. The role of glycosylation and phosphorylation in the expression of active human beta-glucuronidase. J Biol Chem. Jun. 5, 1993;268(16):12193-8.
Sidhu, Navdeep S. Structure of sulfamidase provides insight into the molecular pathology of mucopolysaccharidosis IIIA. Acta Cryst. (2014). D70, 1321-1335.
Sifuentes, et al. A follow-up study of MPS I patients treated with laronidase enzyme replacement therapy for 6 years. Mol Genet Metab. Feb. 2007;90(2):171-80. Epub Sep. 29, 2006.
Siren, et al., Erythropoetin prevents neuronal apoptosis after cerebral ischemia and metabolic stress. Proc Natl Acad Sci U S A. Mar. 27, 2001;98(7):4044-9.
Sivakumur et al., Bone marrow transplantation in mucopolysaccharidosis type IIIA: A comparison of an early treated patient with his untreated sibling. J. Inher. Metab. Dis., 22(849):849-850 (1999).
Skolnick, et al. From genes to protein structure and function: novel applications of computational approaches in the genomic era. Trends Biotechnol. Jan. 2000;18(1):34-9. Review.
Smith et al. Comparison of Biosequences. Advances in Applied Mathematics. 2:482-489 (1981).
Sonoda et al. A Blood-Brain-Barrier-Penetrating Anti-human Transferrin Receptor Antibody Fusion Protein for Neuronopathic Mucopolysaccharidosis II. Mol Ther 26(5):1366-1374 (2018).
Soukharev, et al. Afluorogenic substrate for detection of organophosphatase activity. Anal Biochem. Apr. 1, 2004;327(1):140-8.
Spina, et al., Brain-Derived Neurotrophic Factor Protects Dopamine Neurons Against 6-Hydroxydopamine and N-Methyl-4-Phenylpyridinium Ion Toxicity: Involvement of the Glutathione System. Journal of Neurochemistry1992;59 (1): 99-106.
Strauss, et al., Brain-derived neurotrophic factor variants are associated with childhood-onset mood disorder: confirmation in a Hungarian sample. Molecular Psychiartry 2005;10: 861-67.
Stroobants, S. et al. Intracerebroventricular enzyme infusion corrects central nervous system pathology and dysfunction in a mouse model of metachromatic leukodystrophy.Human Molecular Genetics 20(4); 2760-2769 (2011).
Sukegawa-Hayasaka, et al. Effect of Hunter disease (mucopolysaccharidosis type II) mutations on molecular phenotypes of iduronate-2-sulfatase; enzymatic activity, protein processing and structural analysis. J Inherit Metab Dis 2006;29:755-761.
SUMBRIA; et al., "Brain protection from stroke with intravenous TNFα decoy receptor-Trojan horse fusion protein", J Cereb Blood Flow Metab, Oct. 2012, 32(10), 1933-8.
Sun et al. Comparison of the capability of GDNF, BDNF, or both, to protect nigrostriatal neurons in a rat model of Parkinson's disease. Brain Research 1052(2); 119-29 (Aug. 9, 2005).
Takahashi, et al., Inhibition of cell growth and tumorigenesis of human glioblastoma cells by a neutralizing antibody against human basic fibroblast growth factor. Federation of European Biochemical Societies 1991;288 (1,2): 65-71.
The BDNF Study Group (Phase III). A controlled trial of recombinant methionyl human BDNF in ALS. Neurology 1999;52: 1427-33.
Thoenen, et al. Neurotrophins: from enthusiastic expectations through sobering experiences to rational therapeutic approaches. Nature Neuroscience Supplement 5;2002:1046-50.

(56) References Cited

OTHER PUBLICATIONS

Thompson, et al. Improved binding of a bivalent single-chain immunotoxin results in increased efficacy for in vivo T-cell depletion. Protein Eng. Dec. 2001;14(12):1035-41.
Tobinick et al., "Perispinal etanercept for neuroinflammatory disorders," Drug Discovery Today, vol. 14, No. 3-4, pp. 168-177 (2009).
Tomatsu, et al. Murine model (Galns(tm(C76S)slu)) of MPS IVA with missense mutation at the active site cystein conserved among sulfatase proteins. Mol Genet Metab. Jul. 2007;91(3):251-8.
Tougou, et al. Paraoxonase has a major role in the hydrolysis of prulifloxacin (NM441), a prodrug of a new antibacterial agent. Drug Metab Dispos. Apr. 1998;26(4):355-9.
Traunecker, et al. Highly efficient neutralization of HIV with recombinant CD4-immunoglobulin molecules. Nature, 339(6219);68-70 (May 4, 1989).
Triguero et al. Capillary depletion method for quantification of blood-brain barrier transport of circulating peptides and plasma proteins. J Neurochem. 1990; 54(6):1882-8.
Tsukahara, et al. The Role of Brain-derived Neurotrophic Factor in Transient Forebrain Ischemia in the Rat Brain. Neurosurgery 34 (2);1994:323-31.
Tuma, et al. Transcytosis: crossing cellular barriers. Physiol Rev. Jul. 2003;83(3):871-932.
Um, et al. A "classical" homodimeric erythropoietin receptor is essential for the antiapoptotic effects of erythropoietin on differentiated neuroblastoma SH-SY5Y and pheochromocytoma PC-12 cells. Cell Signal. Mar. 2007;19(3):634-45.
Unger, et al. Recombinant α-iduronidase: characterization of the purified enzyme and correction of mucopolysaccharidosis type I fibroblasts. Biochem J. 1994; 384:43-49.
UniProtKB/Swiss-Prot: P22304. Iduronate 2-sulfatase precursor (Alpha-L-iduronate sulfate sulfatase) (Idursulfase) [Contains: Iduronate 2-sulfatase 42 kDa chain; Iduronate 2-sulfatase 14 kDa chain] (2007)/.
U.S. Appl. No. 14/594,0417 Final Office Action dated Sep. 5, 2019.
U.S. Appl. No. 13/141,682 Final Office Action dated Nov. 10, 2015.
U.S. Appl. No. 13/141,682 Non-Final Office Action dated Mar. 30, 2016.
U.S. Appl. No. 13/141,682 Notice of Allowance dated Aug. 22, 2016.
U.S. Appl. No. 14/144,460 Final Office Action dated Nov. 9, 2016.
U.S. Appl. No. 14/144,460 Non-Final Office Action dated Apr. 21, 2016.
U.S. Appl. No. 14/192,792 Office Action dated Apr. 14, 2017.
U.S. Appl. No. 14/281,803 Office Action dated Jun. 30, 2016.
"U.S. Appl. No. 14/305,402 Office Action dated Jan. 3, 2017".
U.S. Appl. No. 14/538,721 Non-Final Office Action dated Apr. 13, 2017.
"U.S. Appl. No. 14/594,047 Final Office Action dated Jun. 2, 2016".
U.S. Appl. No. 14/594,047 Office Action dated Jan. 18, 2017.
U.S. Appl. No. 14/606,239 Office Action dated Jun. 10, 2016.
U.S. Appl. No. 14/906,259 Non-final Office Action dated Mar. 18, 2019.
U.S. Appl. No. 14/994,067 Non-Final Office Action dated Jan. 17, 2017.
U.S. Appl. No. 15/357,894 Final Office Action dated Mar. 29, 2019.
U.S. Appl. No. 15/397,649 Non-Final Office Action dated Mar. 1, 2018.
U.S. Appl. No. 15/397,649 Notice of Allowance dated Sep. 20, 2018.
U.S. Appl. No. 14/144,460 Final Office Action dated Sep. 30, 2019.
U.S. Appl. No. 14/144,460 Office Action dated Aug. 17, 2015.
U.S. Appl. No. 14/192,792 Final Office Action dated Oct. 30, 2015.
U.S. Appl. No. 14/192,792 Office Action dated Aug. 23, 2016.
U.S. Appl. No. 14/192,792.Office Action dated Jul. 17, 2015.
U.S. Appl. No. 14/281,803 Final Office Action dated Dec. 23, 2019.
U.S. Appl. No. 14/538,721 Office Action dated Dec. 3, 2015.
U.S. Appl. No. 14/538,721 Office Action dated Sep. 8, 2016.
U.S. Appl. No. 14/594,047 Advisory Office Action dated Oct. 17, 2016.
U.S. Appl. No. 14/594,047 Office Action dated Aug. 26, 2015.
U.S. Appl. No. 14/606,239 Notice of Allowability dated Oct. 21, 2016.
U.S. Appl. No. 14/606,239 Notice of Allowance dated Oct. 3, 2016.
U.S. Appl. No. 15/357,894 Non-Final Office Action dated Feb. 13, 2020.
U.S. Appl. No. 15/982,990 Restriction Requirement dated Sep. 20, 2019.
U.S. Appl. No. 14/281,803 Office Action dated May 22, 2019.
Voznyi, et al. A fluorimeteric enzyme assay for the diagnosis of MPS II (Hunter disease). J Inherit Metab Dis. 2001;24:675-80.
Walker, F. et al., Specific binding of radioiodinated granulocyte-macrophage colony-stimulating factor to hemopoietic cells. The EMBO Journal 4(4); pp. 933-939 (1985).
Wang, et al. Identification of the key amino acids of glial cell line-derived neurotrophic factor family receptor alpha1 involved in its biological function. J Biol Chem. Jan. 2, 2004;279(1):109-16.
Ward, E.S. Binding activities of a repertoire of single immunoglobulin variable domains secreted from *Escherichia coli*. Nature. Oct. 12, 1989;341(6242):544-546.
Warrington, et al. Human monoclonal antibodies reactive to oligodendrocytes promote remyelination in a model of multiple sclerosis. Proc Natl Acad Sci U S A. Jun. 6, 2000;97(12):6820-5.
Weich, et al. Interleukin-3/erythropoietin fusion proteins: in vitro effects on hematopoietic cells. Exp Hematol. May 1993;21(5):647-55.
Whetstone, et al. Blood-spinal cord barrier after spinal cord injury: relation to revascularization and wound healing. J Neurosci Res. Oct. 15, 2003;74(2):227-39.
Whittaker, et al. Characterization of the functional insulin binding epitopes of the full-length insulin receptor. J Biol Chem. 2005;280(22):20932-6.
Wiesenhofer, et al. Glial cell line-derived neurotrophic factor (GDNF) and its receptor (GFR-α1) are strongly expressed in human gliomas. Acta Neuropathol. (Berl). 2000;99:131-37.
Wraith, et al. Enzyme replacement therapy for mucopolysaccharidosis I: a randomized, double-blinded, placebo-controlled, multinational study of recombinant human alpha-L-iduronidase (Iaronidase). J Pediatr. May 2004;144(5):581-8.
Wraith, et al. Mucopolysaccharidosis type II (Hunter syndrome): a clinical review and recommendations for treatment in the era of enzyme replacement therapy. Eur J Pediatr. Mar. 2008;167(3):267-77.
Wraith, J. Enzyme replacement therapy in mucopolysaccharidosis type I: progress and emerging difficulties. J Inherit Metab Dis. Apr. 2001;24(2):245-50.
Wu, et al. Drug targeting of a peptide radiopharmaceutical through the primate blood-brain barrier in vivo with a monoclonal antibody to the human insulin receptor. J Clin Invest. Oct. 1, 1997;100(7):1804-12.
Wu, et al. Neuroprotection in Experimental Stroke with Targeted Neurotrophins. NeuroRX: The Journal of the American Society for Experimental NeuroTherapeutics. 2005;2(1):120-128.
Wu, et al. Neuroprotection with noninvasive neurotrophin delivery to the brain. Proc Natl Acad Sci U S A. Jan. 5, 1999;96(1):254-9.
Wu, et al. Simultaneous targeting of multiple disease mediators by a dual-variable-domain immunoglobulin. Nat Biotechnol. Nov. 2007;25(11):1290-7. Epub Oct. 14, 2007.
Xue, et al. Intrastriatal administration of erythropoietin protects dopaminergic neurons and improves neurobehavioral outcome in a rat model of Parkinson's disease. Neuroscience. May 25, 2007;146(3):1245-58.
Yamashita, et al. Post-Occlusion Treatment with BDNF Reduces Infarct Size in a Model of Permanent Occlusion of the Middle Cerebral Artery in Rat. Metabolic Brain Disease 12(4);1997:271-80.
Yan, et al. 1994. Distribution of Intracerebral Ventricularly Administered Neurotrophins in Rat Brain and Its Correlation with Trk Receptor Expression. Experimental Neurology 127: 23-36.
Yan, et al. 2007 Enduring vulnerability to reinstatement of methamphetamine-seeking behavior in glial-cell-line-derived neurotrophic factor mutant mice. FASEB J. Jul;21(9):1994-2004.

(56) References Cited

OTHER PUBLICATIONS

Yip, et al. Three-dimensional structural interactions of insulin and its receptor. J Biol Chem. Jul. 25, 2003;278(30):27329-32.
Zhang, et al. 2001. Conjugation of brain-derived neurotrophic factor to a blood-brain barrier drug targeting system enables neuroprotection in regional brain ischemia following intrvenous injection of the neurotrophin. Brain Research 889: 49-56.
Zhang, et al. 2001. Neuroprotection in Transient Focal Brain Ischemia After Delayed Intravenous Administration of Brain-Derived Neurotrophic Factor Conjugated to a Blood-Brain Barrier Drug Targeting System. Stroke 32: 1378-84.
Zhang, et al. 2001. Rapid transferrin efflux from brain to blood across the blood-brain barrier. J Neurochem. Mar;76(5):1597-600.
Zhang, et al. 2003. Global Non-Viral Gene Transfer to the Primate Brain Following Intravenous Administration. Molecular Therapy 7 (1): 11-18.
Zhang, et al. Mediated efflux of IgG molecules from brain to blood across the blood-brain barrier. J Neuroimmunol. Mar. 1, 2001;114(1-2):168-72.
Zhao, et al. Carbohydrate structures of recombinant human alpha-L-iduronidase secreted by Chinese hamster ovary cells. J Biol Chem. Sep. 5, 1997;272(36):22758-65.
Zhou; et al., "Neuroprotection with a brain-penetrating biologic tumor necrosis factor inhibitor.", J Pharmacol Exp Ther, Nov. 2011, 339(2), 618-23.
Zhou, et al. Brain penetrating IgG-erythropoietin fusion protein is neuroprotective following intravenous treatment in Parkinson's disease in the mouse. Brain Res. Mar. 25, 2011;1382:315-20. Epub Jan. 26, 2011.
Zhou, et all. Brain-penetrating IgG-iduronate 2-sulfatase fusion protein for the mouse. Drug Metab Dispos. Feb. 2012;40(2):329-35. doi: 10.1124/dmd.111.042903. Epub Nov. 7, 2011.
Zito, et al. Sulphatase activities are regulated by the interaction of sulphatase-modifying factor 1 with SUMF2, EMBO Rep 2005;6(7):655-660.
Antibody Structure, retrieved from www.bioatla.com/appendix/antibody-strucutre/ (2020).
Bhagavan et al., Chapter 4—Three Dimensional Structure of Proteins and Disorders of Protein Misfolding. Essentials of Biochemistry (Second Edition). Excerpt section: Covalent and Coordinate Covalent Bonds in Protein Structure: first paragraph. (2015).
Boado et al., Bi-functional IgG-lysosomal enzyme fusion proteins for brain drug delivery. Scientific Reports 9: 18632 (2019).
Boado et al., Comparison of Blood-Brain Barrier Transport of Glial-Derived Neurotrophic Factor (GDNF) and an IgG-GDNF Fusion Protein in the Rhesus Monkey. Drug Metab Dispos 37(12): 2299-2304 (2009).
Condori et al., Enzyme replacement for GM1-gangliosidosis: Uptake, lysosomal activation, and cellular disease correction using a novel β-galactosidase:RTB lectin fusion. Mol Genet Metab. 117(2):199-209 (2016).
Dinatale et al., Heparan N-sulfatase: in vitro mutagenesis of potential N-glycosylation sites. Biochem Biophys Res Commun 280(5):1251-1257 (2001).
Fraldi et al., SUMF1 enhances sulfatase activities in vivo in five sulfatase deficiencies. Biochem J. 403(Pt 2): 305-312 (2007).
Gliddon et al., Purification and characterization of recombinant murine sulfamidase. Mol Genet Metab 83(3):239-245 (2004).
Hemsley et al., Examination of intravenous and intra-CSF protein delivery for treatment of neurological disease. Eur J Neurosci 29(6):1197-1214 (2009).
Jolly et al., Intracisternal enzyme replacement therapy in lysosomal storage diseases: routes of absorption into brain. Neuropathol Appl Neurobiol. 37(4):414-422 (2011).
Karpova et al., A fluorimetric enzyme assay for the diagnosis of Sanfilippo disease type A (MPS IIIA). J Inherit Metab Dis 19(3):278-285 (1996).
Marsh et al., 4-Methylumbelliferyl alpha-N-acetylglucosaminidase activity for diagnosis of Sanfilippo B disease. Clin Genet 27(3): 258-262 (1985).
Montfort et al., Expression and functional characterization of human mutant sulfamidase in insect cells. Mol Genet Metab 83(3):246-251 (2004).
PCT/US2020/012549 International Search Report and Written Opinion dated Apr. 21, 2020.
Scott et al. Cloning of the sulphamidase gene and identification of mutations in Sanfilippo A syndrome. Nat. Genet. 11:465-467 (1995).
Urayama et al., Mannose 6-phosphate receptor-mediated transport of sulfamidase across the blood-brain barrier in the newborn mouse. Mol Ther 16(7):1261-1266 (2008).
U.S. Appl. No. 14/594,047 Non-Final Office Action dated Apr. 30, 2020.
U.S. Appl. No. 15/982,990 Non-Final Office Action dated Apr. 28, 2020.
Valstar et al., Mucopolysaccharidosis type IIIA: clinical spectrum and genotype-phenotype correlations. Ann Neurol 68(6):876-887 (2010).
Weber et al. Cloning and expression of the gene involved in Sanfilippo B syndrome (mucopolysaccharidosis III B). Hum Mol Genet. 5:771-777 (1996).
Xue et al., LINKER: a web server to generate peptide sequences with extended conformation. Nucleic Acids Res. 32: W562-W565 (2004).
Zhao et al., The molecular basis of Sanfilippo syndrome type B. Proc Natl Acad Sci U S A 93(12):6101-6105 (1996).
Alaoui-Ismaili et al., Design of second generation therapeutic recombinant bone morphogenetic proteins. Cytokine & Growth Factor Reviews 20: 501-507 (2009).
Bowie et al., Deciphering the Message in Protein Sequences: Tolerance to Amino Acids Substitutions. Science 247(4948): 1306-1310 (1990).
Guo et al., Protein tolerance to random amino acid change. PNAS 101.25 (2004): 9205-9210.
Pawson et al., Assembly of Cell Regulatory Systems Through Protein Interaction Domains. Science 300: 445-452 (2003).
PCT/US2019/045547 International Preliminary Report on Patentability dated Feb. 9, 2021.
U.S. Appl. No. 14/594,047 Final Office Action dated Feb. 12, 2021.
U.S. Appl. No. 15/357,894 Final Office Action dated Dec. 21, 2020.
U.S. Appl. No. 15/982,990 Final Office Action dated Dec. 14, 2020.
U.S. Appl. No. 16/746,847 Non-Final Office Action dated Mar. 18, 2021.
U.S. Appl. No. 16/828,557 Final Office Action dated Feb. 17, 2021.
U.S. Appl. No. 16/828,557 Non-Final Office Action dated Nov. 6, 2020.
Boado et al., Insulin receptor antibody-iduronate 2-sulfatase fusion protein: pharmacokinetics, anti-drug antibody, and safety pharmacology in Rhesus monkeys. Biotechnol Bioeng 111(11):2317-2325 (2014).
George et al., An analysis of protein domain linkers: their classification and role in protein folding. Protein Engineering, Design and Selection 15(11): 871-879 (2002).
Graham et al. Characteristics of a human cell line transformed by DNA from human adenovirus type 5. J. Gen Virol. 36:59-74 (1977).
Hubbes et al., Human placental beta-galactosidase. Characterization of the dimer and complex forms of the enzyme. Biochem J 285(Pt 3):827-831 (1992).
Mather et al. Culture of testicular cells in hormone-supplemented serum-free medium. Annals N.Y. Acad. Sci. 383:44-68 (1982).
Oshima et al., Cloning, sequencing, and expression of cDNA for human beta-galactosidase. Biochem Biophys Res Commun 157(1):238-244 (1988).
PCT/US2019/067868 International Search Report and Written Opinion dated Mar. 30, 2020.
Samoylova et al., Generation and characterization of recombinant feline beta-galactosidase for preclinical enzyme replacement therapy studies in GM1 gangliosidosis. Metab Brain Dis 23(2):161-173 (2008).
Sands et al., Enzyme replacement therapy for murine mucopolysaccharidosis type VII. J. Clin. Invest. 93:2324-31 (1994).
U.S. Appl. No. 16/746,847 Final Office Action dated Oct. 8, 2021.
U.S. Appl. No. 16/828,557 Non-Final Office Action dated Jul. 27, 2021.

(56) References Cited

OTHER PUBLICATIONS

U.S. Appl. No. 16/905,292 Non-Final Office Action dated Sep. 10, 2021.
Zhang et al., Delivery of beta-galactosidase to mouse brain via the blood-brain barrier transferrin receptor. J Pharmacol Exp Ther 313(3):1075-1081 (2005).
Zhang et al., Kinetic mechanism and characterization of human beta-galactosidase precursor secreted by permanently transfected Chinese hamster ovary cells. Biochem J 304(Pt 1):281-288 (1994).

* cited by examiner

Fig. 1

HIR Ab HC (SEQ ID NO:7)

<u>MDWTWRVFCLLAVAPGAHS</u>QVQLQQSGPELVKPGALVKISCKASG<u>YTFTNYDIHWVK</u>
QRPGQGLEWIG<u>WIYPGDGSTKYNEKFKG</u>KATLTADKSSSTAYMHLSSLTSEKSAVYF
CAR<u>EWAY</u>WGQGTLVTVSAASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSL
SLSPGK

Fig. 2

HIR Ab LC (SEQ ID NO:8)

METPAQLLFLLLLWLPDTTGDIQMTQSPSSLSASLGERVSLTCRASQDIGGNLYWLQ
QGPDGTIKRLIYATSSLDSGVPKRFSGSRSGSDYSLTISSLESEDFVDYYCLQYSSS
PWTFGGGTKMEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKS
FNRGEC

Fig. 3

| HIR Ab HC CDRs | | |
|---|---|---|
| CDR1 | GYTFTNYDIH | SEQ ID NO:1 |
| CDR2 | WIYPGDGSTKYNEKFKG | SEQ ID NO:2 |
| CDR3 | EWAY | SEQ ID NO:3 |
| HIR Ab LC CDRs | | |
| CDR1 | RASQDIGGNLY | SEQ ID NO:4 |
| CDR2 | ATSSLDS | SEQ ID NO:5 |
| CDR3 | LQYSSSPWT | SEQ ID NO:6 |

Fig. 4

Amino Acid Sequence of IDUA (minus signal peptide)
(SEQ ID NO:9)

EAPHLVQVDAARALWPLRRFWRSTGFCPPLPHSQADQYVLSWDQQLNLAYVGAVPHR

GIKQVRTHWLLELVTTRGSTGRGLSYNFTHLDGYLDLLRENQLLPGFELMGSASGHF

TDFEDKQQVFEWKDLVSSLARRYIGRYGLAHVSKWNFETWNEPDHHDFDNVSMTMQG

FLNYYDACSEGLRAASPALRLGGPGDSFHTPPRSPLSWGLLRHCHDGTNFFTGEAGV

RLDYISLHRKGARSSISILEQEKVVAQQIRQLFPKFADTPIYNDEADPLVGWSLPQP

WRADVTYAAMVVKVIAQHQNLLLANTTSAFPYALLSNDNAFLSYHPHPFAQRTLTAR

FQVNNTRPPHVQLLRKPVLTAMGLLALLDEEQLWAEVSQAGTVLDSNHTVGVLASAH

RPQGPADAWRAAVLIYASDDTRAHPNRSVAVTLRLRGVPPGPGLVYVTRYLDNGLCS

PDGEWRRLGRPVFPTAEQFRRMRAAEDPVAAAPRPLPAGGRLTLRPALRLPSLLLVH

VCARPEKPPGQVTRLRALPLTQGQLVLVWSDEHVGSKCLWTYEIQFSQDGKAYTPVS

RKPSTFNLFVFSPDTGAVSGSYRVRALDYWARPGPFSDPVPYLEVPVPRGPPSPGNP

Fig. 5

Amino Acid Sequence of IRMAb-HC-IDUA (SEQ ID NO:10)

MDWTWRVFCLLAVAPGAHSQVQLQQSGPELVKPGALVKISCKASGYTFTNYDIHWVK
QRPGQGLEWIGWIYPGDGSTKYNEKFKGKATLTADKSSSTAYMHLSSLTSEKSAVYF
CAREWAYWGQGTLVTVS*AASTKGPSVFPLAPSSKSTSGGTAALGCLVKDYFPEPVTV*
*SWNSGALTSGVHTFPAVLQSSGLYSLSSVVTVPSSSLGTQTYICNVNHKPSNTKVDK*
*KVEPKSCDKTHTCPPCPAPELLGGPSVFLFPPKPKDTLMISRTPEVTCVVVDVSHED*
*PEVKFNWYVDGVEVHNAKTKPREEQYNSTYRVVSVLTVLHQDWLNGKEYKCKVSNKA*
*LPAPIEKTISKAKGQPREPQVYTLPPSRDELTKNQVSLTCLVKGFYPSDIAVEWESN*
*GQPENNYKTTPPVLDSDGSFFLYSKLTVDKSRWQQGNVFSCSVMHEALHNHYTQKSL*
*SLSPGK*SSEAPHLVQVDAARALWPLRRFWRSTGFCPPLPHSQADQYVLSWDQQLNLA
YVGAVPHRGIKQVRTHWLLELVTTRGSTGRGLSYNFTHLDGYLDLLRENQLLPGFEL
MGSASGHFTDFEDKQQVFEWKDLVSSLARRYIGRYGLAHVSKWNFETWNEPDHHDFD
NVSMTMQGFLNYYDACSEGLRAASPALRLGGPGDSFHTPPRSPLSWGLLRHCHDGTN
FFTGEAGVRLDYISLHRKGARSSISILEQEKVVAQQIRQLFPKFADTPIYNDEADPL
VGWSLPQPWRADVTYAAMVVKVIAQHQNLLLANTTSAFPYALLSNDNAFLSYHPHPF
AQRTLTARFQVNNTRPPHVQLLRKPVLTAMGLLALLDEEQLWAEVSQAGTVLDSNHT
VGVLASAHRPQGPADAWRAAVLIYASDDTRAHPNRSVAVTLRLRGVPPGPGLVYVTR
YLDNGLCSPDGEWRRLGRPVFPTAEQFRRMRAAEDPVAAAPRPLPAGGRLTLRPALR
LPSLLLVHVCARPEKPPGQVTRLRALPLTQGQLVLVWSDEHVGSKCLWTYEIQFSQD
GKAYTPVSRKPSTFNLFVFSPDTGAVSGSYRVRALDYWARPGPFSDPVPYLEVPVPR
GPPSPGNP

Fig. 11
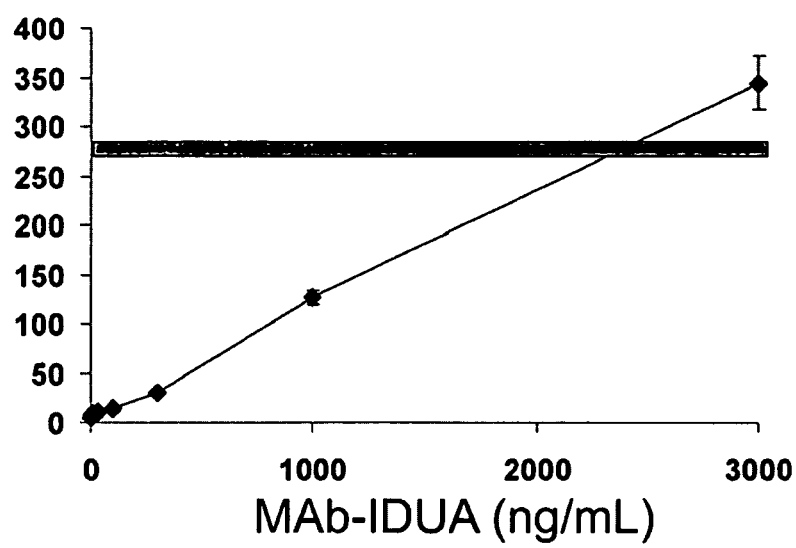
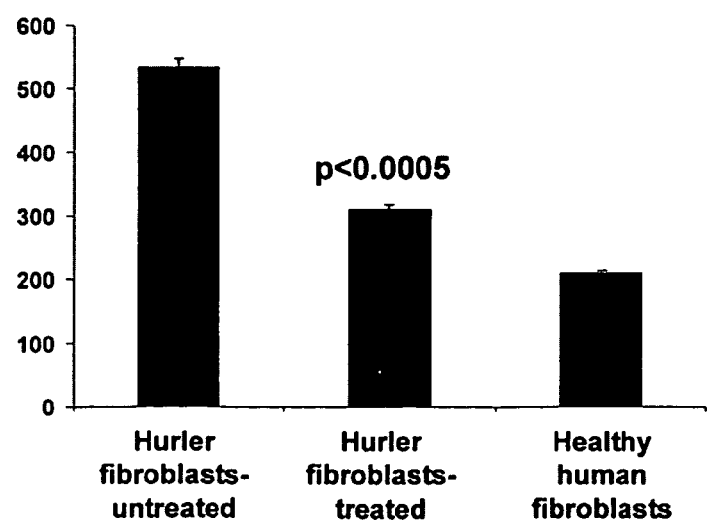

Fig. 13
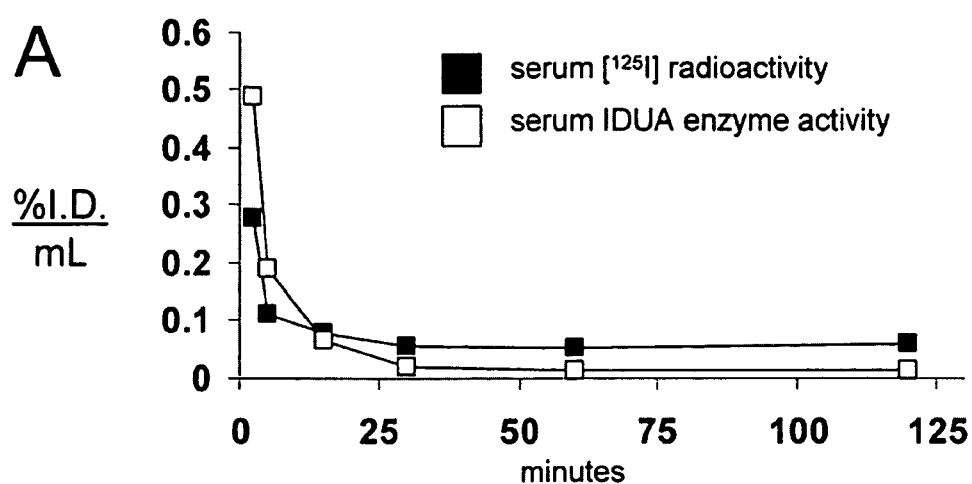
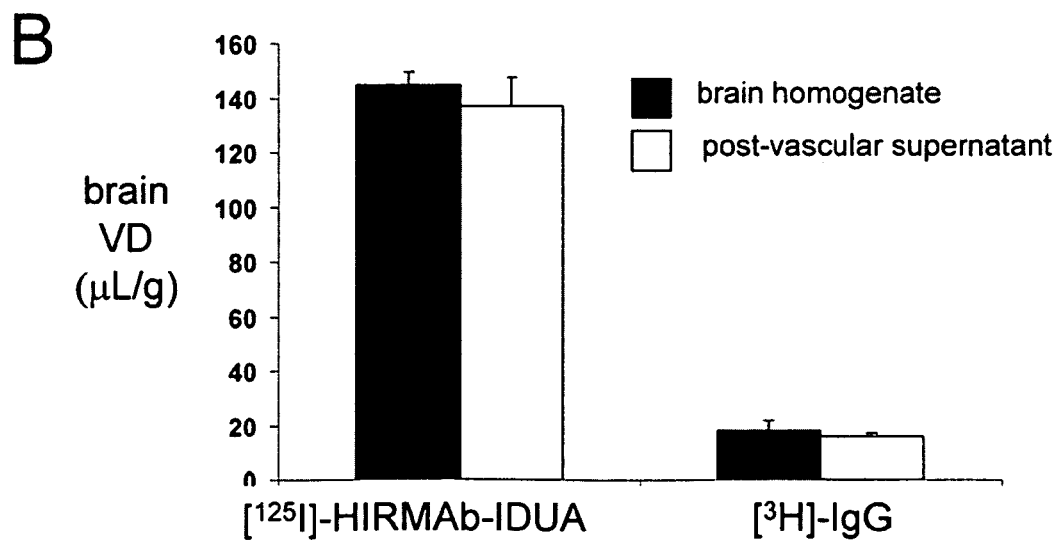

minutes

SEQUENCE LISTING

```
<160> NUMBER OF SEQ ID NOS: 13

<210> SEQ ID NO 1
<211> LENGTH: 10
<212> TYPE: PRT
<213> ORGANISM: Homo sapiens

<400> SEQUENCE: 1

Gly Tyr Thr Phe Thr Asn Tyr Asp Ile His
1               5                   10

<210> SEQ ID NO 2
<211> LENGTH: 17
<212> TYPE: PRT
<213> ORGANISM: Homo sapiens
```

```
<400> SEQUENCE: 2

Trp Ile Tyr Pro Gly Asp Gly Ser Thr Lys Tyr Asn Glu Lys Phe Lys
1               5                   10                  15

Gly

<210> SEQ ID NO 3
<211> LENGTH: 4
<212> TYPE: PRT
<213> ORGANISM: Homo sapiens

<400> SEQUENCE: 3

Glu Trp Ala Tyr
1

<210> SEQ ID NO 4
<211> LENGTH: 11
<212> TYPE: PRT
<213> ORGANISM: Homo sapiens

<400> SEQUENCE: 4

Arg Ala Ser Gln Asp Ile Gly Gly Asn Leu Tyr
1               5                   10

<210> SEQ ID NO 5
<211> LENGTH: 7
<212> TYPE: PRT
<213> ORGANISM: Homo sapiens

<400> SEQUENCE: 5

Ala Thr Ser Ser Leu Asp Ser
1               5

<210> SEQ ID NO 6
<211> LENGTH: 9
<212> TYPE: PRT
<213> ORGANISM: Homo sapiens

<400> SEQUENCE: 6

Leu Gln Tyr Ser Ser Ser Pro Trp Thr
1               5

<210> SEQ ID NO 7
<211> LENGTH: 462
<212> TYPE: PRT
<213> ORGANISM: Homo sapiens

<400> SEQUENCE: 7

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110
```

Tyr Phe Cys Ala Arg Glu Trp Ala Tyr Trp Gly Gln Gly Thr Leu Val
            115                 120                 125

Thr Val Ser Ala Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
450                 455                 460

<210> SEQ ID NO 8
<211> LENGTH: 234
<212> TYPE: PRT
<213> ORGANISM: Homo sapiens

<400> SEQUENCE: 8

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser

```
                  20                  25                  30
Ala Ser Leu Gly Glu Arg Val Ser Leu Thr Cys Arg Ala Ser Gln Asp
            35                  40                  45
Ile Gly Gly Asn Leu Tyr Trp Leu Gln Gln Gly Pro Asp Gly Thr Ile
        50                  55                  60
Lys Arg Leu Ile Tyr Ala Thr Ser Ser Leu Asp Ser Gly Val Pro Lys
 65                  70                  75                  80
Arg Phe Ser Gly Ser Arg Ser Gly Ser Asp Tyr Ser Leu Thr Ile Ser
                 85                  90                  95
Ser Leu Glu Ser Glu Asp Phe Val Asp Tyr Tyr Cys Leu Gln Tyr Ser
            100                 105                 110
Ser Ser Pro Trp Thr Phe Gly Gly Gly Thr Lys Met Glu Ile Lys Arg
        115                 120                 125
Thr Val Ala Ala Pro Ser Val Phe Ile Phe Pro Pro Ser Asp Glu Gln
130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 9
<211> LENGTH: 627
<212> TYPE: PRT
<213> ORGANISM: Homo sapiens

<400> SEQUENCE: 9

Glu Ala Pro His Leu Val Gln Val Asp Ala Ala Arg Ala Leu Trp Pro
  1               5                  10                  15
Leu Arg Arg Phe Trp Arg Ser Thr Gly Phe Cys Pro Pro Leu Pro His
            20                  25                  30
Ser Gln Ala Asp Gln Tyr Val Leu Ser Trp Asp Gln Gln Leu Asn Leu
        35                  40                  45
Ala Tyr Val Gly Ala Val Pro His Arg Gly Ile Lys Gln Val Arg Thr
    50                  55                  60
His Trp Leu Leu Glu Leu Val Thr Thr Arg Gly Ser Thr Gly Arg Gly
 65                  70                  75                  80
Leu Ser Tyr Asn Phe Thr His Leu Asp Gly Tyr Leu Asp Leu Leu Arg
                 85                  90                  95
Glu Asn Gln Leu Leu Pro Gly Phe Glu Leu Met Gly Ser Ala Ser Gly
            100                 105                 110
His Phe Thr Asp Phe Glu Asp Lys Gln Gln Val Phe Glu Trp Lys Asp
        115                 120                 125
Leu Val Ser Ser Leu Ala Arg Arg Tyr Ile Gly Arg Tyr Gly Leu Ala
    130                 135                 140
His Val Ser Lys Trp Asn Phe Glu Thr Trp Asn Glu Pro Asp His His
145                 150                 155                 160
```

```
Asp Phe Asp Asn Val Ser Met Thr Met Gln Gly Phe Leu Asn Tyr Tyr
                165                 170                 175

Asp Ala Cys Ser Glu Gly Leu Arg Ala Ala Ser Pro Ala Leu Arg Leu
            180                 185                 190

Gly Gly Pro Gly Asp Ser Phe His Thr Pro Arg Ser Pro Leu Ser
        195                 200                 205

Trp Gly Leu Leu Arg His Cys His Asp Gly Thr Asn Phe Phe Thr Gly
        210                 215                 220

Glu Ala Gly Val Arg Leu Asp Tyr Ile Ser Leu His Arg Lys Gly Ala
225                 230                 235                 240

Arg Ser Ser Ile Ser Ile Leu Glu Gln Glu Lys Val Val Ala Gln Gln
                245                 250                 255

Ile Arg Gln Leu Phe Pro Lys Phe Ala Asp Thr Pro Ile Tyr Asn Asp
            260                 265                 270

Glu Ala Asp Pro Leu Val Gly Trp Ser Leu Pro Gln Pro Trp Arg Ala
        275                 280                 285

Asp Val Thr Tyr Ala Ala Met Val Val Lys Val Ile Ala Gln His Gln
        290                 295                 300

Asn Leu Leu Leu Ala Asn Thr Thr Ser Ala Phe Pro Tyr Ala Leu Leu
305                 310                 315                 320

Ser Asn Asp Asn Ala Phe Leu Ser Tyr His Pro His Pro Phe Ala Gln
                325                 330                 335

Arg Thr Leu Thr Ala Arg Phe Gln Val Asn Asn Thr Arg Pro Pro His
            340                 345                 350

Val Gln Leu Leu Arg Lys Pro Val Leu Thr Ala Met Gly Leu Leu Ala
        355                 360                 365

Leu Leu Asp Glu Glu Gln Leu Trp Ala Glu Val Ser Gln Ala Gly Thr
370                 375                 380

Val Leu Asp Ser Asn His Thr Val Gly Val Leu Ala Ser Ala His Arg
385                 390                 395                 400

Pro Gln Gly Pro Ala Asp Ala Trp Arg Ala Ala Val Leu Ile Tyr Ala
                405                 410                 415

Ser Asp Asp Thr Arg Ala His Pro Asn Arg Ser Val Ala Val Thr Leu
            420                 425                 430

Arg Leu Arg Gly Val Pro Pro Gly Pro Gly Leu Val Tyr Val Thr Arg
        435                 440                 445

Tyr Leu Asp Asn Gly Leu Cys Ser Pro Asp Gly Glu Trp Arg Arg Leu
        450                 455                 460

Gly Arg Pro Val Phe Pro Thr Ala Glu Gln Phe Arg Arg Met Arg Ala
465                 470                 475                 480

Ala Glu Asp Pro Val Ala Ala Pro Arg Pro Leu Pro Ala Gly Gly
                485                 490                 495

Arg Leu Thr Leu Arg Pro Ala Leu Arg Leu Pro Ser Leu Leu Leu Val
            500                 505                 510

His Val Cys Ala Arg Pro Glu Lys Pro Pro Gly Gln Val Thr Arg Leu
        515                 520                 525

Arg Ala Leu Pro Leu Thr Gln Gly Gln Leu Val Leu Val Trp Ser Asp
530                 535                 540

Glu His Val Gly Ser Lys Cys Leu Trp Thr Tyr Glu Ile Gln Phe Ser
545                 550                 555                 560

Gln Asp Gly Lys Ala Tyr Thr Pro Val Ser Arg Lys Pro Ser Thr Phe
                565                 570                 575

Asn Leu Phe Val Phe Ser Pro Asp Thr Gly Ala Val Ser Gly Ser Tyr
```

```
                    580                 585                 590
        Arg Val Arg Ala Leu Asp Tyr Trp Ala Arg Pro Gly Pro Phe Ser Asp
                    595                 600                 605

Pro Val Pro Tyr Leu Glu Val Pro Val Pro Arg Gly Pro Pro Ser Pro
                    610                 615                 620

Gly Asn Pro
        625

<210> SEQ ID NO 10
<211> LENGTH: 1091
<212> TYPE: PRT
<213> ORGANISM: Homo sapiens

<400> SEQUENCE: 10

Met Asp Trp Thr Trp Arg Val Phe Cys Leu Leu Ala Val Ala Pro Gly
        1                   5                   10                  15

Ala His Ser Gln Val Gln Leu Gln Gln Ser Gly Pro Glu Leu Val Lys
                            20                  25                  30

Pro Gly Ala Leu Val Lys Ile Ser Cys Lys Ala Ser Gly Tyr Thr Phe
                        35                  40                  45

Thr Asn Tyr Asp Ile His Trp Val Lys Gln Arg Pro Gly Gln Gly Leu
        50                  55                  60

Glu Trp Ile Gly Trp Ile Tyr Pro Gly Asp Gly Ser Thr Lys Tyr Asn
        65                  70                  75                  80

Glu Lys Phe Lys Gly Lys Ala Thr Leu Thr Ala Asp Lys Ser Ser Ser
                            85                  90                  95

Thr Ala Tyr Met His Leu Ser Ser Leu Thr Ser Glu Lys Ser Ala Val
                        100                 105                 110

Tyr Phe Cys Ala Arg Glu Trp Ala Tyr Trp Gly Gln Gly Thr Leu Val
                    115                 120                 125

Thr Val Ser Ala Ala Ser Thr Lys Gly Pro Ser Val Phe Pro Leu Ala
        130                 135                 140

Pro Ser Ser Lys Ser Thr Ser Gly Gly Thr Ala Ala Leu Gly Cys Leu
        145                 150                 155                 160

Val Lys Asp Tyr Phe Pro Glu Pro Val Thr Val Ser Trp Asn Ser Gly
                            165                 170                 175

Ala Leu Thr Ser Gly Val His Thr Phe Pro Ala Val Leu Gln Ser Ser
                        180                 185                 190

Gly Leu Tyr Ser Leu Ser Ser Val Val Thr Val Pro Ser Ser Ser Leu
                    195                 200                 205

Gly Thr Gln Thr Tyr Ile Cys Asn Val Asn His Lys Pro Ser Asn Thr
        210                 215                 220

Lys Val Asp Lys Lys Val Glu Pro Lys Ser Cys Asp Lys Thr His Thr
        225                 230                 235                 240

Cys Pro Pro Cys Pro Ala Pro Glu Leu Leu Gly Gly Pro Ser Val Phe
                            245                 250                 255

Leu Phe Pro Pro Lys Pro Lys Asp Thr Leu Met Ile Ser Arg Thr Pro
                        260                 265                 270

Glu Val Thr Cys Val Val Val Asp Val Ser His Glu Asp Pro Glu Val
                    275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
        305                 310                 315                 320
```

```
Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Glu Ala Pro His Leu Val Gln Val Asp Ala Ala Arg Ala Leu Trp Pro
465                 470                 475                 480

Leu Arg Arg Phe Trp Arg Ser Thr Gly Phe Cys Pro Pro Leu Pro His
                485                 490                 495

Ser Gln Ala Asp Gln Tyr Val Leu Ser Trp Asp Gln Leu Asn Leu
            500                 505                 510

Ala Tyr Val Gly Ala Val Pro His Arg Gly Ile Lys Gln Val Arg Thr
        515                 520                 525

His Trp Leu Leu Glu Leu Val Thr Thr Arg Gly Ser Thr Gly Arg Gly
    530                 535                 540

Leu Ser Tyr Asn Phe Thr His Leu Asp Gly Tyr Leu Asp Leu Leu Arg
545                 550                 555                 560

Glu Asn Gln Leu Leu Pro Gly Phe Glu Leu Met Gly Ser Ala Ser Gly
                565                 570                 575

His Phe Thr Asp Phe Glu Asp Lys Gln Gln Val Phe Glu Trp Lys Asp
            580                 585                 590

Leu Val Ser Ser Leu Ala Arg Arg Tyr Ile Gly Arg Tyr Gly Leu Ala
        595                 600                 605

His Val Ser Lys Trp Asn Phe Glu Thr Trp Asn Glu Pro Asp His His
    610                 615                 620

Asp Phe Asp Asn Val Ser Met Thr Met Gln Gly Phe Leu Asn Tyr Tyr
625                 630                 635                 640

Asp Ala Cys Ser Glu Gly Leu Arg Ala Ala Ser Pro Ala Leu Arg Leu
                645                 650                 655

Gly Gly Pro Gly Asp Ser Phe His Thr Pro Arg Ser Pro Leu Ser
            660                 665                 670

Trp Gly Leu Leu Arg His Cys His Asp Gly Thr Asn Phe Phe Thr Gly
        675                 680                 685

Glu Ala Gly Val Arg Leu Asp Tyr Ile Ser Leu His Arg Lys Gly Ala
    690                 695                 700

Arg Ser Ser Ile Ser Ile Leu Glu Gln Glu Lys Val Val Ala Gln Gln
705                 710                 715                 720

Ile Arg Gln Leu Phe Pro Lys Phe Ala Asp Thr Pro Ile Tyr Asn Asp
                725                 730                 735

Glu Ala Asp Pro Leu Val Gly Trp Ser Leu Pro Gln Pro Trp Arg Ala
```

```
                740                 745                 750
Asp Val Thr Tyr Ala Ala Met Val Val Lys Val Ile Ala Gln His Gln
        755                 760                 765
Asn Leu Leu Leu Ala Asn Thr Thr Ser Ala Phe Pro Tyr Ala Leu Leu
        770                 775                 780
Ser Asn Asp Asn Ala Phe Leu Ser Tyr His Pro His Pro Phe Ala Gln
785                 790                 795                 800
Arg Thr Leu Thr Ala Arg Phe Gln Val Asn Asn Thr Arg Pro Pro His
                805                 810                 815
Val Gln Leu Leu Arg Lys Pro Val Leu Thr Ala Met Gly Leu Leu Ala
                820                 825                 830
Leu Leu Asp Glu Glu Gln Leu Trp Ala Glu Val Ser Gln Ala Gly Thr
            835                 840                 845
Val Leu Asp Ser Asn His Thr Val Gly Val Leu Ala Ser Ala His Arg
        850                 855                 860
Pro Gln Gly Pro Ala Asp Ala Trp Arg Ala Ala Val Leu Ile Tyr Ala
865                 870                 875                 880
Ser Asp Asp Thr Arg Ala His Pro Asn Arg Ser Val Ala Val Thr Leu
                885                 890                 895
Arg Leu Arg Gly Val Pro Pro Gly Pro Gly Leu Val Tyr Val Thr Arg
                900                 905                 910
Tyr Leu Asp Asn Gly Leu Cys Ser Pro Asp Gly Glu Trp Arg Arg Leu
                915                 920                 925
Gly Arg Pro Val Phe Pro Thr Ala Glu Gln Phe Arg Arg Met Arg Ala
            930                 935                 940
Ala Glu Asp Pro Val Ala Ala Pro Arg Pro Leu Pro Ala Gly Gly
945                 950                 955                 960
Arg Leu Thr Leu Arg Pro Ala Leu Arg Leu Pro Ser Leu Leu Leu Val
                965                 970                 975
His Val Cys Ala Arg Pro Glu Lys Pro Pro Gly Gln Val Thr Arg Leu
            980                 985                 990
Arg Ala Leu Pro Leu Thr Gln Gly Gln Leu Val Leu Val Trp Ser Asp
        995                 1000                1005
Glu His Val Gly Ser Lys Cys Leu Trp Thr Tyr Glu Ile Gln Phe
    1010                1015                1020
Ser Gln Asp Gly Lys Ala Tyr Thr Pro Val Ser Arg Lys Pro Ser
    1025                1030                1035
Thr Phe Asn Leu Phe Val Phe Ser Pro Asp Thr Gly Ala Val Ser
    1040                1045                1050
Gly Ser Tyr Arg Val Arg Ala Leu Asp Tyr Trp Ala Arg Pro Gly
    1055                1060                1065
Pro Phe Ser Asp Pro Val Pro Tyr Leu Glu Val Pro Val Pro Arg
    1070                1075                1080
Gly Pro Pro Ser Pro Gly Asn Pro
    1085                1090

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```

```
gcgtggccat gcgtccccctg cgcccccgcg ccgcgctgct ggcgctcctg        50

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagaggcccc gcacctggtg caggtggacg cggcccgcgc gctgtg             46

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcatggattg cccggggatg ggggccctct tggcacaggg acc                43
```

METHODS AND COMPOSITIONS FOR INCREASING ALPHA-L-IDURONIDASE ACTIVITY IN THE CNS

CROSS-REFERENCE

This application is a continuation of U.S. patent application Ser. No. 15/397,649, filed Jan. 3, 2017, and issued as U.S. Pat. No. 10,202,467 on Feb. 12, 2019, which is a continuation of U.S. patent application Ser. No. 14/606,239, filed Jan. 27, 2015, and issued as U.S. Pat. No. 9,567,400 on Feb. 14, 2017, which is a continuation of U.S. application Ser. No. 12/179,806, filed Jul. 25, 2008 and issued as U.S. Pat. No. 8,974,791 on Mar. 10, 2015, which claims the benefit of U.S. Provisional Application Ser. No. 60/952,547, filed Jul. 27, 2007, the contents of which are incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Jul. 9, 2015, is named 28570-704-303-sequence-listing.txt and is 22,760 bytes in size.

BACKGROUND OF THE INVENTION

Type I mucopolysaccharidosis (MPS), also known as Hurler's syndrome, is an inherited metabolic disease caused by a defect in the enzyme α-L-iduronidase (IDUA), which functions to degrade mucopolysaccharides. An insufficient level of IDUA causes a pathological buildup of heparan sulfate and dermatan sulfate in, e.g., the heart, liver, and central nervous system. Symptoms including neurodegeneration and mental retardation appear during childhood and early death can occur due to organ damage. Typically, treatment includes intravenous enzyme replacement therapy with recombinant IDUA. However, systemically administered recombinant IDUA does not cross the blood brain barrier (BBB), and therefore has little impact on the effects of the disease in the central nervous system (CNS).

SUMMARY OF THE INVENTION

Described herein are methods and compositions for treating a subject suffering from an IDUA deficiency. In particular, the methods allow delivery of IDUA to the CNS by systemically administering a therapeutically effective amount of a bifunctional human insulin receptor antibody-IDUA (HIR Ab-IDUA) fusion antibody. The HIR Ab-IDUA fusion antibody binds to the extracellular domain of the insulin receptor and is transported across the blood brain barrier into the CNS, while retaining IDUA activity. A therapeutically effective systemic dose of a HIR Ab-IDUA fusion antibody for systemic administration will be based, in part, on the specific CNS uptake characteristics of the fusion antibody from peripheral blood as described herein.

Accordingly, in one aspect provided herein is a method for treating an α-L-iduronidase deficiency in the central nervous system of a subject in need thereof, comprising systemically administering to the subject a therapeutically effective dose of a fusion antibody having α-L-iduronidase activity. The method is characterized by the following: (i) at least about 0.5% of the therapeutically effective dose is delivered to the brain; (ii) the fusion antibody: comprises: (a) a fusion protein containing the amino acid sequence of an immunoglobulin heavy chain and an α-L-iduronidase, and (b) an immunoglobulin light chain; (iii) the fusion antibody binds to an extracellular domain of the human insulin receptor; and catalyzes hydrolysis of unsulfated alpha-L-iduronosidic linkages in dermatan sulfate; and (iv) the amino acid sequence of the α L iduronidase is covalently linked to the carboxy terminus of the amino acid sequence of the immunoglobulin heavy chain.

In some embodiments at least about 50,000 units of α-L-iduronidase activity are delivered to the brain. In some embodiments, the therapeutically effective dose of the fusion antibody comprises at least about $1 \times 10^6$ units of α-L-iduronidase activity or at least about 140,000 units/Kg of body weight. In some embodiments the IDUA specific activity of the fusion antibody is at least 200,000 units/mg. In some embodiments, systemic administration is parenteral, intravenous, subcutaneous, intra-muscular, trans-nasal, intra-arterial, transdermal, or respiratory. In some embodiments, delivery of at least 0.5% of the therapeutically effective dose to the brain occurs within two hours or less after the systemic administration.

In some embodiments, the fusion antibody is a chimeric antibody.

In some embodiments, the immunoglobulin heavy chain of the fusion antibody comprises a CDR1 corresponding to the amino acid sequence of SEQ ID NO:1 with up to 4 single amino acid mutations, a CDR2 corresponding to the amino acid sequence of SEQ ID NO:2 with up to 6 single amino acid mutations, or a CDR3 corresponding to the amino acid sequence of SEQ ID NO:3 with up to 3 single amino acid mutations, wherein the single amino acid mutations are substitutions, deletions, or insertions.

In other embodiments, the immunoglobulin heavy chain of the fusion antibody comprises a CDR1 corresponding to the amino acid sequence of SEQ ID NO:1 with up to 3 single amino acid mutations, a CDR2 corresponding to the amino acid sequence of SEQ ID NO:2 with up to 6 single amino acid mutations, and a CDR3 corresponding to the amino acid sequence of SEQ ID NO:3 with up to 3 single amino acid mutations.

In other embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, or a CDR3 corresponding to the amino acid sequence of SEQ ID NO:3.

In further embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3.

In some embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, or a CDR3 corresponding to the amino acid sequence of SEQ ID NO:6 with up to 5 single amino acid mutations, wherein the single amino acid mutations are substitutions, deletions, or insertions.

In other embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, and a CDR3 corresponding to the amino acid sequence of SEQ ID NO:6 with up to 5 single amino acid mutations.

In other embodiments, the immunoglobulin light chain of the fusion antibody comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6.

In further embodiments, the immunoglobulin light chain of the fusion antibody comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3; and the immunoglobulin light chain comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody is at least 90% identical to SEQ ID NO:7 and the amino acid sequence of the light chain immunoglobulin is at least 90% identical to SEQ ID NO:8.

In some embodiments, the immunoglobulin heavy chain of the fusion antibody comprises SEQ ID NO:7 and the amino acid sequence of the light chain immunoglobulin comprises SEQ ID NO:8

In yet further embodiments, the α-L-iduronidase comprises an amino acid sequence at least 90% (e.g., 95%, or 100%) identical to SEQ ID NO:9.

In other embodiments, the amino acid sequence of the immunoglobulin heavy chain of the fusion antibody at least 90% identical to SEQ ID NO:7; the amino acid sequence of the light chain immunoglobulin is at least 90% identical to SEQ ID NO:8; and the amino acid sequence of the α-L-iduronidase is at least 95% identical to SEQ ID NO:9 or comprises SEQ ID NO:9.

In still other embodiments, the amino acid sequence of the immunoglobulin heavy chain of the fusion antibody comprises SEQ ID NO:8, the amino acid sequence of the immunoglobulin light chain comprises SEQ ID NO:8, and the amino acid sequence of the IDUA comprises SEQ ID NO:9

In a further aspect provided herein is a method for treating an α-L-iduronidase deficiency in the central nervous system of a subject in need thereof, comprising systemically administering to the subject a therapeutically effective dose of a fusion antibody having α-L-iduronidase activity, where the method is characterized in that (i) at least about 0.5% of the systemically administered therapeutically effective dose is delivered to the brain; (ii) the fusion antibody: comprises: (a) a fusion protein at least 95% identical to SEQ ID NO:10, and (b) an immunoglobulin light chain; and (iii) the fusion antibody binds to an extracellular domain of the human insulin receptor; and catalyzes hydrolysis of unsulfated alpha-L-iduronosidic linkages in dermatan sulfate.

In yet another aspect provided herein is a method for treating an α-L-iduronidase deficiency in the central nervous system of a subject in need thereof, comprising systemically administering to the subject a therapeutically effective dose of a fusion antibody having α-L-iduronidase activity, where the method is characterized in that: (i) at least about 0.5% of the therapeutically effective dose is delivered to the brain; (ii) the fusion antibody: comprises a fusion protein containing the amino acid sequence of an immunoglobulin heavy chain and an α-L-iduronidase; or comprises a fusion protein containing the amino acid sequence of an immunoglobulin light chain and an α-L-iduronidase; binds to the extracellular domain of the human insulin receptor; and catalyzes hydrolysis of unsulfated alpha-L-iduronosidic linkages in dermatan sulfate; and (iii) the amino acid sequence of the α-L-iduronidase is covalently linked to the carboxy terminus of the amino acid sequence of the immunoglobulin heavy chain or the immunoglobulin light chain.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims A better understanding of the features and advantages of the present invention will be obtained by reference to the following detailed description that sets forth illustrative embodiments, in which the principles of the invention are utilized, and the accompanying drawings, as follow:

FIG. 1. Amino acid sequence of an immunoglobulin heavy chain variable region from an exemplary human insulin receptor antibody directed against the extracellular domain of the human insulin receptor. The underlined sequences are a signal peptide, CDR1, CDR2, and CDR3, respectively. The heavy chain constant region, taken from human IgG1, is shown in italics.

FIG. 2. Amino acid sequence of an immunoglobulin light chain variable region from an exemplary human insulin receptor antibody directed against the extracellular domain of the human insulin receptor. The underlined sequences are a signal peptide, CDR1, CDR2, and CDR3, respectively. The constant region, derived from human kappa light chain, is shown in italics.

FIG. 3. A table showing the CDR1, CDR2, and CDR3 amino acid sequences from a heavy and light chain of an exemplary human insulin receptor antibody directed against the extracellular domain of the human insulin receptor.

FIG. 4. Amino acid sequence of human α-L-iduronidase (IDUA) (GenBank NP_000194), not including the initial 26 amino acid signal peptide (mature IDUA).

FIG. 5. Amino acid sequence of a fusion of an exemplary human insulin receptor antibody heavy chain to mature human IDUA. The underlined sequences are, in order, an IgG signal peptide, CDR1, CDR2, CDR3, and a peptide linker linking the carboxy terminus of the heavy chain to the amino terminus of the IDUA. Sequence in italic corresponds to the heavy chain constant region, taken from human IgG1. The sequence in bold corresponds to human IDUA.

FIG. 11. (A) Intracellular IDUA enzyme activity is increased in Hurler fibroblasts in proportion to the concentration of medium HIR Ab-IDUA fusion protein. Data are mean±SE (n=3 dishes/point). The horizontal bar is the IDUA enzyme activity in healthy human fibroblasts (284±5 units/mg protein). (B) Reversal of glycosaminoglycan (GAG) accumulation in Hurler fibroblasts with a single treatment of 0.3 µg/mL of HIR Ab-IDUA fusion protein in the medium. There is a 70% reduction in GAG accumulation, as compared to the $^{35}S$ incorporation in healthy human fibroblasts (p<0.0005). Data are mean±SE (n=5 dishes/point).

FIG. 13. Pharmacokinetics and brain uptake of fusion protein in the adult Rhesus monkey. (A) The serum concentration, expressed as a percent of injected dose (ID)/mL, of the [$^{125}I$]-HIR Ab-IDUA fusion protein is plotted vs. time after a single intravenous injection of the protein in the anesthetized adult Rhesus monkey; the serum concentration is expressed as either $^{125}I$ radioactivity (closed symbol) or IDUA enzyme activity (open symbol). (B) The volume of distribution (VD) at 120 min after injection of the [$^{125}I$]-HIR Ab-IDUA fusion protein is shown for the total brain homogenate and the post-vascular supernatant. The equivalence of the VD in both compartments is evidence for transport of the fusion protein through the BBB in vivo (Methods). The data for the [$^{3}H$]-mouse IgG2a is from Pardridge et al (1995).

DETAILED DESCRIPTION OF THE INVENTION

Introduction

Figure 6:
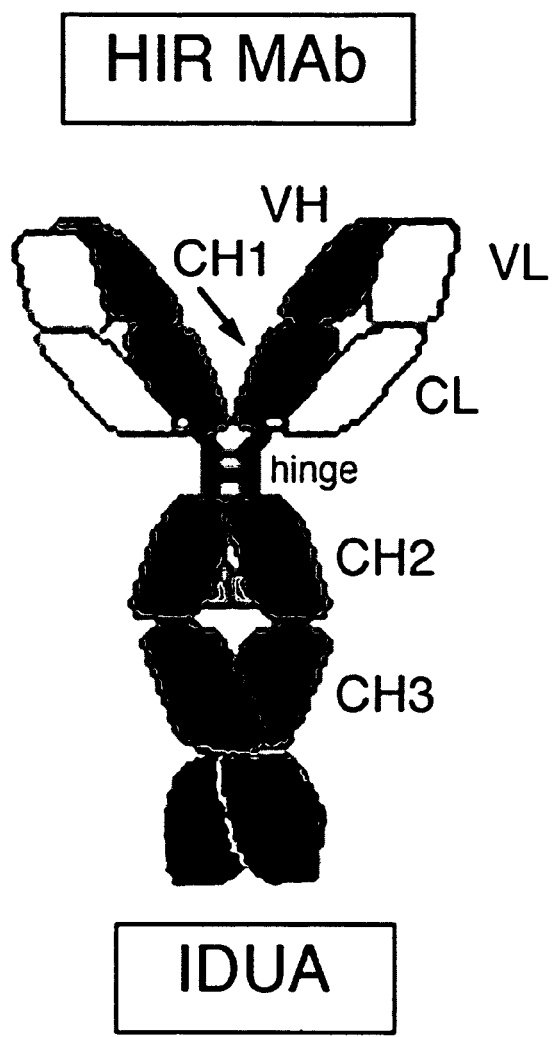
FIG. 6. An exemplary HIR Ab-IDUA fusion antibody is formed by fusion of the amino terminus of the mature IDUA to the carboxyl terminus of the CH3 region of the heavy chain of the HIR Ab. The fusion protein is a bi-functional molecule: the fusion protein binds the HIR, at the BBB, to mediate transport into the brain, and expresses IDUA enzyme activity, which is deficient in MPS Type I (Hurler's syndrome).

The blood brain barrier is a severe impediment to the delivery of systemically administered IDUA (e.g., recombinant IDUA) to the central nervous system. The methods and compositions described herein address three factors that are important in delivering a therapeutically significant level of IDUA activity across the BBB to the CNS: 1) Modification of an IDUA to allow it to cross the BBB; 2) the amount and rate of uptake of systemically administered modified IDUA into the CNS, and 3) Retention of IDUA activity once across the BBB. Various aspects of the methods and compositions described herein address these factors, by (1) providing human insulin receptor (HIR) antibody (Ab)-IDUA fusion antibodies comprising an IDUA (i.e., a protein having IDUA activity) fused, with or without intervening sequence, to an immunoglobulin (heavy chain or light chain) directed against the extracellular domain of a human insulin receptor; and (2) establishing therapeutically effective systemic doses of the fusion antibodies based on a characterization of their uptake in the CNS and their specific activity.

Accordingly, the invention provides compositions and methods for treating a α-L-iduronidase deficiency in the central nervous system by systemically administering to a subject in need thereof a therapeutically effective dose of a bifunctional HIR Ab-IDUA fusion antibody having α-L-iduronidase activity and selectively binding to the extracellular domain of a human insulin receptor.

Some Definitions

"Treatment" or "treating" as used herein includes achieving a therapeutic benefit and/or a prophylactic benefit. By therapeutic benefit is meant eradication or amelioration of the underlying disorder or condition being treated. For example, in an individual with Hurler's syndrome, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a lysosomal storage disorder), or decreasing the likelihood of occurrence of a condition. As used herein, "treating" or "treatment" includes prophylaxis.

As used herein, the term "effective amount" can be an amount, which when administered systemically, is sufficient to effect beneficial or desired results in the CNS, such as beneficial or desired clinical results, or enhanced cognition, memory, mood, or other desired CNS results. An effective amount is also an amount that produces a prophylactic effect, e.g., an amount that delays, reduces, or eliminates the appearance of a pathological or undesired condition. Such conditions include, but are not limited to, mental retardation, hearing loss, and neurodegeneration. An effective amount can be administered in one or more administrations. In terms of treatment, an "effective amount" of a composition of the invention is an amount that is sufficient to palliate, ameliorate, stabilize, reverse or slow the progression of a disorder, e.g., a neurological disorder. An "effective amount" may be of any of the compositions of the invention used alone or in conjunction with one or more agents used to treat a disease or disorder. An "effective amount" of a therapeutic agent within the meaning of the present invention will be determined by a patient's attending physician or veterinarian. Such amounts are readily ascertained by one of ordinary skill in the art and will a therapeutic effect when administered in accordance with the present invention. Factors which influence what a therapeutically effective amount will be include, the IDUA specific activity of the HIR Ab-IDUA fusion antibody administered, its absorption profile (e.g., its rate of uptake into the brain), time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is an animal, for example, a mammal. In some embodiments a "subject" or an "individual" is a human In some embodiments, the subject suffers from Mucopolysaccharidosis Type I H ("Hurler's Syndrome"), Mucopolysaccharidosis Type I S ("Scheie Syndrome"), or Mucopolysaccharidosis Type I H-S ("Hurler-Scheie Syndrome).

In some embodiments, a pharmacological composition comprising an HIR-IDUA fusion antibody is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, intra-arterial, subcutaneous, intramuscular, intraperitoneal, transdermal, by inhalation, transbuccal, intranasal, rectal, oral, parenteral, sublingual, or trans-nasal.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in Remington's Pharmaceutical Sciences, Gennaro, A R, ed., 20th edition, 2000: Williams and Wilkins Pa., USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysothate-80 at 0.01-1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al. *J. Biol. Chem.* 260:2605-2608 (1985); and Cassol et al. (1992); Rossolini et al., *Mol. Cell. Probes* 8:91-98 (1994)).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc. . . . ) in a sample. In another example, a polypeptide is purified if it is substantially removed from or concentrated in its natural environment. Methods for purification and isolation of nucleic acids and proteins are well known in the art.

The Blood Brain Barrier

In one aspect, the invention provides compositions and methods that utilize an IDUA fused to an HIR Ab capable of crossing the blood brain barrier (BBB). The compositions and methods are useful in transporting IDUA from the peripheral blood and across the blood brain barrier into the CNS. As used herein, the "blood-brain barrier" refers to the barrier between the peripheral circulation and the brain and spinal cord which is formed by tight junctions within the brain capillary endothelial plasma membranes, creates an extremely tight barrier that restricts the transport of molecules into the brain, even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to as the blood-brain barrier or BBB.

The BBB limits the development of new neurotherapeutics, diagnostics, and research tools for the brain and CNS. Essentially 100% of large molecule therapeutics such as recombinant proteins, antisense drugs, gene medicines, purified antibodies, or RNA interference (RNAi)-based drugs, do not cross the BBB in pharmacologically significant amounts. While it is generally assumed that small molecule drugs can cross the BBB, in fact, <2% of all small molecule drugs are active in the brain owing to the lack transport across the BBB. A molecule must be lipid soluble and have a molecular weight less than 400 Daltons (Da) in order to cross the BBB in pharmacologically significant amounts, and the vast majority of small molecules do not have these dual molecular characteristics. Therefore, most potentially therapeutic, diagnostic, or research molecules do not cross the BBB in pharmacologically active amounts. So as to bypass the BBB, invasive transcranial drug delivery strategies are used, such as intracerebro-ventricular (ICV) infusion, intracerebral (IC) administration, and convection enhanced diffusion (CED). Transcranial drug delivery to the brain is expensive, invasive, and largely ineffective. The ICV route delivers IDUA only to the ependymal surface of the brain, not into brain parenchyma, which is typical for drugs given by the ICV route. The IC administration of an enzyme such as IDUA, only provides local delivery, owing to the very low efficiency of protein diffusion within the brain. The CED results in preferential fluid flow through the white matter tracts of brain, which causes demyelination, and astrogliosis.

The methods described herein offer an alternative to these highly invasive and generally unsatisfactory methods for bypassing the BBB, allowing a functional IDUA to cross the BBB from the peripheral blood into the CNS following systemic administration of an HIR-IDUA fusion antibody composition described herein. The methods described herein exploit the expression of insulin receptors (e g, human insulin receptors) on the BBB to shuttle desired a bifunctional HIR-IDUA fusion antibody from peripheral blood into the CNS.

Insulin Receptors

The BBB has been shown to have specific receptors, including insulin receptors, that allow the transport from the blood to the brain of several macromolecules. In particular, insulin receptors are suitable as transporters for the HIR Ab-IDUA fusion antibodies described herein. The HIR-IDUA fusion antibodies described herein bind to the extracellular domain (ECD) of the human insulin receptor.

Insulin receptors and their extracellular, insulin binding domain (ECD) have been extensively characterized in the art both structurally and functionally. See, e.g., Yip et al (2003), "*J Biol. Chem,* 278(30):27329-27332; and Whittaker et al. (2005), *J Biol Chem,* 280(22):20932-20936. The amino acid and nucleotide sequences of the human insulin receptor can be found under GenBank accession No. NM_000208.

Figure 7:
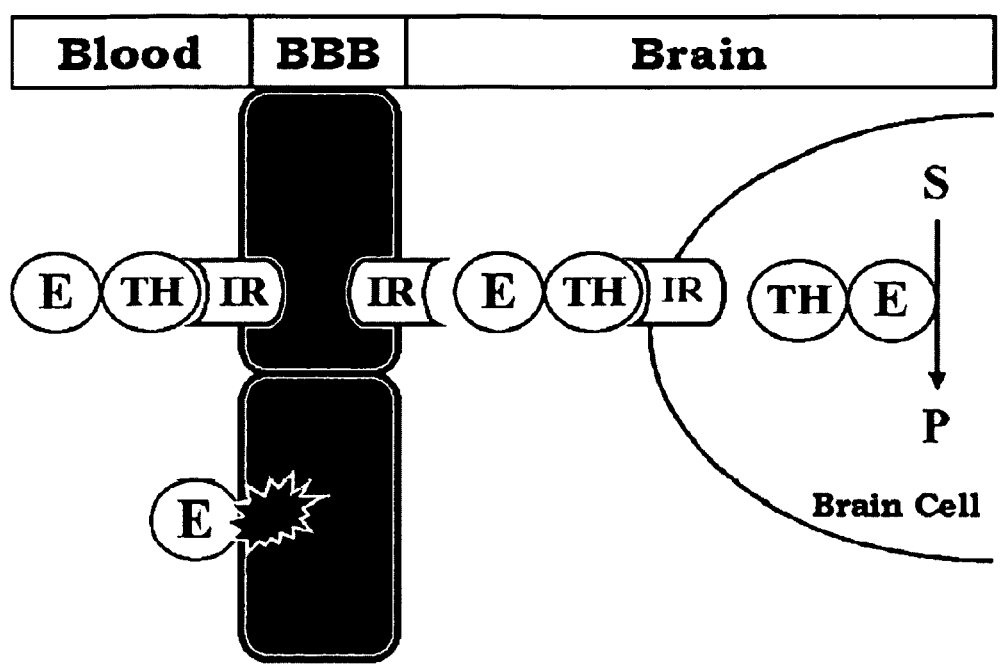
FIG. 7. Schematic depiction of a "molecular trojan horse" strategy in which the fusion antibody comprises an antibody to the extracellular domain of the human insulin receptor, which acts as a molecular Trojan horse (TH), and IDUA, a lysosomal enzyme (E). By itself, the IDUA normally does not cross the blood-brain barrier (BBB). However, following fusion of the IDUA to the TH, the enzyme is able to cross the BBB, and the brain cell membrane, by trafficking on the IR, which is expressed at both membranes in the brain.

Antibodies that Bind to an Insulin Receptor Mediated Transport System and Other Receptor Mediated Transport Systems of the BBB One noninvasive approach for the delivery of IDUA to the CNS is to fuse the IDUA to an antibody that selectively binds to the ECD of the insulin receptor. Insulin receptors expressed on the BBB can thereby serve as a vector for transport of the IDUA across the BBB. Certain ECD-specific antibodies may mimic the endogenous ligand and thereby traverse a plasma membrane barrier via transport on the specific receptor system. Such insulin receptor antibodies act as molecular "Trojan horses," as depicted schematically in FIG. 7. Thus, despite the fact that antibodies and other macromolecules are normally excluded from the brain, they can be an effective vehicle for the delivery of molecules into the brain parenchyma if they have specificity for the extracellular domain of a receptor expressed on the BBB, e.g., the insulin receptor. In certain embodiments, an HIR Ab-IDUA fusion antibody binds an exofacial epitope on the human BBB HIR and this binding enables the fusion antibody to traverse the BBB via a transport reaction that is mediated by the human BBB insulin receptor. In addition, other known BBB targeting agents (also referred to herein as "Trojan horses"), such as endogenous peptides or modified proteins, including endogenous peptides, such as transferrin, insulin, leptin, insulin-like growth factors (IGFs), or cationic peptides, or peptidomimetic monoclonal antibodies to the BBB transferrin receptor, insulin receptor, IGF receptor, or leptin receptor may be used to deliver enzymes of the type and size-range mentioned above across the BBB.

The term "antibody" describes an immunoglobulin whether natural or partly or wholly synthetically produced. The term also covers any polypeptide or protein having a binding domain which is, or is homologous to, an antigen-binding domain CDR grafted antibodies are also contemplated by this term.

"Native antibodies" and "native immunoglobulins" are usually heterotetrameric glycoproteins of about 150,000 daltons, composed of two identical light (L) chains and two identical heavy (H) chains Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("VH") followed by a number of constant domains ("CH"). Each light chain has a variable domain at one end ("VL") and a constant domain ("CL") at its other end; the constant domain of the light chain is aligned with the first constant domain of the heavy chain, and the light-chain variable domain is aligned with the variable domain of the heavy chain Particular amino acid residues are believed to form an interface between the light- and heavy-chain variable domains.

The term "variable domain" refers to protein domains that differ extensively in sequence among family members (i.e. among different isoforms, or in different species). With respect to antibodies, the term "variable domain" refers to the variable domains of antibodies that are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the "framework region" or "FR". The variable domains of unmodified heavy and light chains each comprise four FRs (FR1, FR2, FR3 and FR4, respectively), largely adopting a γ-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from three "complementarity determining regions" or "CDRs", which directly bind, in a complementary manner, to an antigen and are known as CDR1, CDR2, and CDR3 respectively.

In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3); Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901 917 (1987)).

As used herein, "variable framework region" or "VFR" refers to framework residues that form a part of the antigen binding pocket or groove and/or that may contact antigen. In some embodiments, the framework residues form a loop that is a part of the antigen binding pocket or groove. The amino acids residues in the loop may or may not contact the antigen. In an embodiment, the loop amino acids of a VFR are determined by inspection of the three-dimensional structure of an antibody, antibody heavy chain, or antibody light chain. The three-dimensional structure can be analyzed for solvent accessible amino acid positions as such positions are likely to form a loop and/or provide antigen contact in an antibody variable domain Some of the solvent accessible positions can tolerate amino acid sequence diversity and others (e.g. structural positions) can be less diversified. The three dimensional structure of the antibody variable domain can be derived from a crystal structure or protein modeling. In some embodiments, the VFR comprises, consist essentially of, or consists of amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3. The VFR can form a loop that is well positioned to make contact with a target antigen or form a part of the antigen binding pocket.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ") and lambda or ("λ"), based on the amino acid sequences of their constant domains.

In referring to an antibody or fusion antibody described herein, the terms "selectively bind," "selectively binding,"

"specifically binds," or "specifically binding" refer to binding to the antibody or fusion antibody to its target antigen for which the dissociation constant (Kd) is about $10^{-6}$ M or lower, i.e., $10^{-7}$, $10^{-8}$, $10^{-9}$, $10^{-10}$, $10^{-11}$, or $10^{-12}$M.

The term antibody as used herein will also be understood to mean one or more fragments of an antibody that retain the ability to specifically bind to an antigen, (see generally, Holliger et al., Nature Biotech. 23 (9) 1126-1129 (2005)). Non-limiting examples of such antibodies include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423 426; and Huston et al. (1988) Proc. Natl. Acad. Sci. USA 85:5879 5883; and Osbourn et al. (1998) Nat. Biotechnol. 16:778). Such single chain antibodies are also intended to be encompassed within the term antibody. Any VH and VL sequences of specific scFv can be linked to human immunoglobulin constant region cDNA or genomic sequences, in order to generate expression vectors encoding complete IgG molecules or other isotypes. VH and VL can also be used in the generation of Fab, Fv or other fragments of immunoglobulins using either protein chemistry or recombinant DNA technology. Other forms of single chain antibodies, such as diabodies are also encompassed.

"F(ab')2" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CHγ1 (γ1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')2.

The Fab fragment also contains the constant domain of the light chain and the first constant domain (CH1) of the heavy chain Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise a VH, a VL, or both a VH and VL domain of an antibody, wherein both domains are present in a single polypeptide chain. In some embodiments, the Fv polypeptide further comprises a polypeptide linker between the VH and VL domains which enables the sFv to form the desired structure for antigen binding. For a review of sFv see, e.g., Pluckthun in The Pharmacology of Monoclonal Antibodies, Vol. 113, Rosenburg and Moore eds. Springer-Verlag, New York, pp. 269 315 (1994).

A "chimeric" antibody includes an antibody derived from a combination of different mammals The mammal may be, for example, a rabbit, a mouse, a rat, a goat, or a human. The combination of different mammals includes combinations of fragments from human and mouse sources.

In some embodiments, an antibody of the present invention is a monoclonal antibody (MAb), typically a chimeric human-mouse antibody derived by humanization of a mouse monoclonal antibody. Such antibodies are obtained from, e.g., transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesis human antibodies specific for human antigens, and the mice can be used to produce human antibody-secreting hybridomas.

For use in humans, a chimeric HIR Ab is preferred that contains enough human sequence that it is not significantly immunogenic when administered to humans, e.g., about 80% human and about 20% mouse, or about 85% human and about 15% mouse, or about 90% human and about 10% mouse, or about 95% human and 5% mouse, or greater than about 95% human and less than about 5% mouse. Chimeric antibodies to the human BBB insulin receptor with sufficient human sequences for use in the invention are described in, e.g., Boado et al. (2007), *Biotechnol Bioeng,* 96(2):381-391. A more highly humanized form of the HIR MAb can also be engineered, and the humanized HIR Ab has activity comparable to the murine HIR Ab and can be used in embodiments of the invention. See, e.g., U.S. Patent Application Publication Nos. 20040101904, filed Nov. 27, 2002 and 20050142141, filed Feb. 17, 2005.

In exemplary embodiments, the HIR antibodies or HIR-IDUA fusion antibodies derived therefrom contain an immunoglobulin heavy chain comprising CDRs corresponding to the sequence of at least one of the HC CDRs listed in FIG. 3 (SEQ ID NOs 1-3) or a variant thereof. For example, a HC CDR1 corresponding to the amino acid sequence of SEQ ID NO:1 with up to 1, 2, 3, 4, 5, or 6 single amino acid mutations, a HC CDR2 corresponding to the amino acid sequence of SEQ ID NO:2 with up to 1, 2, 3, 4, 5, 6, 7, 8, 9, or 10 single amino acid mutations, or a HC CDR3 corresponding to the amino acid sequence of SEQ ID NO:3 with up to 1, or 2 single amino acid mutations, where the single amino acid mutations are substitutions, deletions, or insertions.

In other embodiments, the HIR Abs or HIR Ab-IDUA fusion Abs contain an immunoglobulin HC the amino acid sequence of which is at least 50% identical (i.e., at least, 55, 60, 65, 70, 75, 80, 85, 90, 95, or any other percent up to 100% identical) to SEQ ID NO:7 (shown in FIG. 1).

In some embodiments, the HIR Abs or HIR AB-IDUA fusion Abs include an immunoglobulin light chain comprising CDRs corresponding to the sequence of at least one of the LC CDRs listed in FIG. 3 (SEQ ID NOs: 4-6) or a variant thereof. For example, a LC CDR1 corresponding to the amino acid sequence of SEQ ID NO:4 with up to 1, 2, 3, 4, or 5 single amino acid mutations, a LC CDR2 corresponding to the amino acid sequence of SEQ ID NO:5 with up to 1, 2, 3, or 4 single amino acid mutations, or a LC CDR3 corresponding to the amino acid sequence of SEQ ID NO:6 with up to 1, 2, 3, 4, or 5 single amino acid mutations.

In other embodiments, the HIR Abs or HIR AB-IDUA fusion Abs contain an immunoglobulin LC the amino acid sequence of which is at least 50% identical (i.e., at least, 55, 60, 65, 70, 75, 80, 85, 90, 95, or any other percent up to 100% identical) to SEQ ID NO:8 (shown in FIG. 2).

In yet other embodiments, the HIR Abs or HIR Ab-IDUA fusion Abs contain both a heavy chain and a light chain corresponding to any of the above-mentioned HIR heavy chains and HIR light chains.

HIR antibodies used in the invention may be glycosylated or non-glycosylated. If the antibody is glycosylated, any pattern of glycosylation that does not significantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody is glycosylated in the pattern produced by a transfected Chinese hamster ovary (CHO) cell.

One of ordinary skill in the art will appreciate that current technologies permit a vast number of sequence variants of candidate HIR Abs or known HIR Abs to be readily generated be (e.g., in vitro) and screened for binding to a target antigen such as the ECD of the human insulin receptor or an isolated epitope thereof. See, e.g., Fukuda et al. (2006) "In vitro evolution of single-chain antibodies using mRNA display," *Nuc. Acid Res.*, 34(19) (published online) for an example of ultra high throughput screening of antibody sequence variants. See also, Chen et al. (1999), "In vitro scanning saturation mutagenesis of all the specificity determining residues in an antibody binding site," *Prot Eng,* 12(4): 349-356. An insulin receptor ECD can be purified as described in, e.g., Coloma et al. (2000) *Pharm Res,* 17:266-274, and used to screen for HIR Abs and HIR Ab sequence variants of known HIR Abs.

Accordingly, in some embodiments, a genetically engineered HIR Ab, with the desired level of human sequences, is fused to an IDUA, to produce a recombinant fusion antibody that is a bi-functional molecule. The HIR Ab-IDUA fusion antibody: (i) binds to an extracellular domain of the human insulin receptor; (ii) catalyzes hydrolysis of unsulfated alpha-L-iduronosidic linkages in dermatan sulfate; and (iii) is able to cross the BBB, via transport on the BBB HIR, and retain IDUA activity once inside the brain, following peripheral administration.

α-L-Iduronidase (IDUA)

Systemic administration (e.g., by intravenous injection) of recombinant IDUA (e.g., Aldurazyme®) fails to rescue a deficiency of IDUA in the CNS of patients suffering from Hurler's syndrome. IDUA does not cross the BBB, and the lack of transport of the enzyme across the BBB prevents it from having a significant therapeutic effect in the CNS following peripheral administration. However, when the IDUA is fused to an HIR Ab (e.g., by a linker), this enzyme is now able to enter the CNS from blood following a non-invasive peripheral route of administration such as intravenous, intra-arterial, intramuscular, subcutaneous, intraperitoneal, or even oral administration Administration of a HIR Ab-IDUA fusion antibody enables delivery of IDUA activity into the brain from peripheral blood. Described herein is the determination of a systemic dose of the HIR Ab-IDUA fusion antibody that is therapeutically effective for treating an IDUA deficiency in the CNS. As described herein, appropriate systemic doses of an HIR Ab-IDUA fusion antibody are established based on a quantitative determination of CNS uptake characteristics and enzymatic activity of an HIR Ab-IDUA fusion antibody.

As used herein, IDUA refers to any naturally occurring or artificial enzyme that can catalyze the hydrolysis of unsulfated alpha-L-iduronosidic linkages in dermatan sulfate, e.g., the human IDUA sequence listed under GenBank Accession No. NP 000194.

In some embodiments, IDUA has an amino acid sequence that is a at least 50% identical (i.e., at least, 55, 60, 65, 70, 75, 80, 85, 90, 95, or any other percent up to 100% identical) to the amino acid sequence of human IDUA, a 653 amino acid protein listed under GenBank Accession No. NP_000194, or a 627 amino acid subsequence thereof, which lacks a 26 amino acid signal peptide, and corresponds to SEQ ID NO:9 (FIG. 4). The structure-function relationship of human IDUA is well established, as described in, e.g., Rempel et al. (2005), "A homology model for human α-L-Iduronidase: Insights into human disease," *Mol. Genetics and Met.,* 85:28-37. In particular, residues that are critical to the function of IDUA include, e.g., Gly 51, Ala 75, Ala 160, Glu 182, Gly 208, Leu 218, Asp 315, Ala 327, Asp 349, Thr 366, Thr 388, Arg 489, Arg 628, Ala 79, His 82, Glu 178, Ser 260, Leu 346, Asn 350, Thr 364, Leu 490, Pro 496, Pro 533, Arg 619, Arg 89, Cys 205, His 240, Ala 319, Gln 380, Arg 383, and Arg 492.

In some embodiments, IDUA has an amino acid sequence at least 50% identical (i.e., at least, 55, 60, 65, 70, 75, 80, 85, 90, 95, or any other percent up to 100% identical) to SEQ ID NO:9 (shown in FIG. 4). Sequence variants of a canonical IDUA sequence such as SEQ ID NO:9 can be generated, e.g., by random mutagenesis of the entire sequence or specific subsequences corresponding to particular domains. Alternatively, site directed mutagenesis can be performed reiteratively while avoiding mutations to residues known to be critical to IDUA function such as those given above. Further, in generating multiple variants of an IDUA sequence, mutation tolerance prediction programs can be used to greatly reduce the number of non-functional sequence variants that would be generated by strictly random mutagenesis. Various programs) for predicting the effects of amino acid substitutions in a protein sequence on protein function (e.g., SIFT, PolyPhen, PANTHER PSEC, PMUT, and TopoSNP) are described in, e.g., Henikoff et al. (2006), "Predicting the Effects of Amino Acid Substitutions on Protein Function," *Annu. Rev. Genomics Hum. Genet.,*

7:61-80. IDUA sequence variants can be screened for of IDUA activity/retention of IDUA activity by, e.g., 4-methylumbelliferyl α-L-iduronide (MUBI) flurometric IDUA assays known in the art. See, e.g., Kakkis et al. (1994), *Prot Expr Purif* 5:225-232. One unit of IDUA activity is defined as the hydrolysis of 1 nmole substrate/hour. Accordingly, one of ordinary skill in the art will appreciate that a very large number of operable IDUA sequence variants can be obtained by generating and screening extremely diverse "libraries" of IDUA sequence variants by methods that are routine in the art, as described above.

Percent sequence identity is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO:24 or SEQ ID NO: 39) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

The present invention also includes proteins having a conservative amino acid change, compared with an amino acid sequence disclosed herein. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the invention.

Compositions

Strikingly, it has been found that the bifunctional HIR Ab-IDUA fusion antibodies described herein, retain a high proportion of the activity of their separate constituent proteins, i.e., binding of the HIR Ab to the IR ECD and transport across the BBB, and the enzymatic activity of IDUA. Construction of cDNAs and expression vectors encoding any of the proteins described herein, as well as their expression and purification are well within those of ordinary skill in the art, and are described in detail herein in, e.g., Examples 1-3, and, in Boado et al (2007), *Biotechnol Bioeng* 96:381-391, U.S. patent application Ser. No. 11/061,956, and U.S. patent application Ser. No. 11/245,710.

Described herein are bifunctional HIR Ab-IDUA fusion antibodies containing a HIR Ab, as described herein, capable of crossing the BBB fused to IDUA, where the HIR Ab is capable of crossing the blood brain barrier and the IDUA each retain an average of at least about 10, 20, 30, 40, 50, 60, 70, 80, 90, 95, 99, or 100% of their activities, compared to their activities as separate entities. In some embodiments, the invention provides a HIR Ab-IDUA fusion antibody where the HIR Ab and IDUA each retain an average of at least about 50% of their activities, compared to their activities as separate entities. In some embodiments, the invention provides a HIR Ab-IDUA fusion antibody where the HIR Ab and IDUA each retain an average of at least about 60% of their activities, compared to their activities as separate entities. In some embodiments, the invention provides a HIR Ab-IDUA fusion antibody where the HIR Ab and IDUA each retain an average of at least about 70% of their activities, compared to their activities as separate entities. In some embodiments, the invention provides a HIR Ab-IDUA fusion antibody where the HIR Ab and IDUA each retain an average of at least about 80% of their activities, compared to their activities as separate entities. In some embodiments, the invention provides a fusion HIR Ab-IDUA fusion antibody where the HIR Ab and IDUA each retain an average of at least about 90% of their activities, compared to their activities as separate entities. In some embodiments, the HIR Ab retains at least about 10, 20, 30, 40, 50, 60, 70, 80, 90, 95, 99, or 100% of its activity, compared to its activity as a separate entity, and the IDUA retains at least about 10, 20, 30, 40, 50, 60, 70, 80, 90, 95, 99, or 100% of its activity, compared to its activity as a separate entity. Accordingly, described herein are compositions containing a bifunctional HIR Ab-IDUA fusion antibody capable of crossing the BBB, where the constituent HIR Ab and IDUA each retain, as part of the fusion antibody, an average of at least about 10, 20, 30, 40, 50, 60, 70, 80, 90, 95, 99, or 100% of their activities, i.e., HIR binding and IDUA activity, respectively, compared to their activities as separate proteins. An HIR Ab IDUA fusion antibody refers to a fusion protein comprising any of the HIR antibodies and IDUAs described herein.

In the HIR Ab-IDUA fusion antibodies described herein, the covalent linkage between the antibody and the IDUA may be to the carboxy or amino terminal of the HIR antibody and the amino or carboxy terminal of the IDUA as long as the linkage allows the HIR Ab-IDUA fusion antibody to bind to the ECD of the IR and cross the blood brain barrier, and allows the IDUA to retain a therapeutically useful portion of its activity. In certain embodiments, the covalent link is between an HC of the antibody and the IDUA or a LC of the antibody and the IDUA. Any suitable linkage may be used, e.g., carboxy terminus of light chain to amino terminus of IDUA, carboxy terminus of heavy chain to amino terminus of IDUA, amino terminus of light chain to amino terminus of IDUA, amino terminus of heavy chain to amino terminus of IDUA, carboxy terminus of light chain to carboxy terminus of IDUA, carboxy terminus of heavy chain to carboxy terminus of IDUA, amino terminus of light chain to carboxy terminus of IDUA, or amino terminus of heavy chain to carboxy terminus of IDUA. In some embodiments, the linkage is from the carboxy terminus of the HC to the amino terminus of the IDUA.

It will be appreciated that a linkage between terminal amino acids can be accomplished by an intervening peptide linker sequence that forms part of the fused amino acid sequence. The peptide sequence linker may be 1, 2, 3, 4, 5, 6, 7, 8, 9, 10, or more than 10 amino acids in length. In some embodiments, a two amino acid linker is used. In some embodiments, the linker has the sequence ser-ser. The peptide linker sequence may include a protease cleavage site, however this is not a requirement for activity of the IDUA; indeed, an advantage of these embodiments of the present invention is that the bifunctional HIR Ab-IDUA fusion antibody, without cleavage, is partially or fully active both for transport and for activity once across the BBB. FIG. 5 shows an exemplary embodiment of the amino acid sequence of a HIR Ab-IDUA fusion antibody (SEQ ID NO:10) in which the HC is fused through its carboxy terminus via a two amino acid "ser-ser" linker to the amino terminus of the IDUA. In some embodiments, the fused IDUA sequence is devoid of its 26 amino acid signal peptide, as shown in FIG. 4.

In some embodiments, a HIR Ab-IDUA fusion antibody comprises both a HC and a LC. In some embodiments, the HIR Ab-IDUA fusion antibody is a monovalent antibody. In other embodiments, the HIR Ab-IDUA fusion antibody is a divalent antibody, as described herein in the Example section.

The HIR Ab used as part of the HIR Ab-IDUA fusion antibody can be glycosylated or nonglycosylated; in some embodiments, the antibody is glycosylated, e.g., in a glycosylation pattern produced by its synthesis in a CHO cell.

As used herein, "activity" includes physiological activity (e.g., ability to cross the BBB and/or therapeutic activity), binding affinity of the HIR Ab for the IR ECD, or the enzymatic activity of IDUA.

Transport of a HIR Ab-IDUA fusion antibody across the BBB may be compared to transport across the BBB of the HIR Ab alone by standard methods. For example, pharmacokinetics and brain uptake of the HIR Ab-IDUA fusion antibody by a model animal, e.g., a mammal such as a primate, may be used. Such techniques are illustrated in Example 5, which demonstrates pharmacokinetics and brain uptake of a fusion protein of the invention by the adult Rhesus monkey. Similarly, standard models for determining IDUA activity may also be used to compare the function of the IDUA alone and as part of a HIR Ab-IDUA fusion antibody. See, e.g., Example 3, which demonstrates the enzymatic activity of IDUA versus HIR Ab-IDUA fusion antibody. Binding affinity for the IR ECD can be compared for the HIR Ab-IDUA fusion antibody versus the HIR Ab alone. See, e.g., Example 4 herein.

Also included herein are pharmaceutical compositions that contain one or more HIR Ab-IDUA fusion antibodies described herein and a pharmaceutically acceptable excipient. A thorough discussion of pharmaceutically acceptable carriers/excipients can be found in Remington's Pharmaceutical Sciences, Gennaro, A R, ed., 20th edition, 2000: Williams and Wilkins Pa., USA. Pharmaceutical compositions of the invention include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration.

The compositions of the invention are particular suited for injection, e.g., as a pharmaceutical composition for intravenous, subcutaneous, intramuscular, or intraperitoneal administration. Aqueous compositions of the present invention comprise an effective amount of a composition of the present invention, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, e g, a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sothic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be systemically administered in a manner compatible with the dosage formulation and in such amount as is therapeutically effective based on the criteria described herein. The formulations are easily administered in a variety of dosage forms, such as the type of injectable solutions described above, but drug release capsules and the like can also be employed The appropriate quantity of a pharmaceutical composition to be administered, the number of treatments, and unit dose will vary according to the CNS uptake characteristics of a HIR Ab-IDUA fusion antibody as described herein, and according to the subject to be treated, the state of the subject and the effect desired. The person responsible for administration will, in any event, determine the appropriate dose for the individual subject.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284, 262), transdermal administration (See U.S. Pat. Nos. 6,348, 210; and 6,322,808) and transmucosal administration (See U.S. Pat. No. 5,656,284). Such methods of administration are well known in the art. One may also use intranasal administration of the present invention, such as with nasal solutions or sprays, aerosols or inhalants Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

Methods

Described herein are methods for delivering an effective dose of IDUA to the CNS across the BBB by systemically administering a therapeutically effective amount of a HIR Ab-IDUA fusion antibody, as described herein. Suitable systemic doses for delivery of a HIR Ab-IDUA fusion antibody is based on its CNS uptake characteristics and IDUA specific activity as described herein. Systemic administration of a HIR Ab-IDUA fusion antibody to a subject suffering from an IDUA deficiency is an effective approach to the non-invasive delivery of IDUA to the CNS.

The amount of a HIR-IDUA fusion antibody that is a therapeutically effective systemic dose of a HIR Ab-IDUA fusion antibody depends, in part, on the CNS uptake characteristics of the HIR-IDUA fusion antibody to be administered, as described herein, e.g., the percentage of the systemically administered dose to be taken up in the CNS.

In some embodiments, 0.3% (i.e., about 0.32%, 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered HIR Ab-IDUA fusion antibody is delivered to the brain as a result of its uptake from peripheral blood across the BBB. In some embodiments, at least 0.5%, (i.e., about 0.32%, 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered dose of the HIR Ab-IDUA fusion antibody is delivered to the brain within two hours or less, i.e., 1.8, 1.7, 1.5, 1.4, 1.3, 1.2, 1.1, 0.9, 0.8, 0.6, 0.5 or any other period from about 0.5 to about two hours after systemic administration.

Accordingly, in some embodiments the invention provides methods of administering a therapeutically effective amount of a HIR Ab-IDUA fusion antibody systemically, such that the amount of the HIR Ab-IDUA fusion antibody to cross the BBB provides at least 0.2 units of IDUA activity/mg protein in the subject's brain, i.e., 0.21, 0.22, 0.25, 0.4, 0.5, 0.6, 0.7, 0.9, 1, 1.1, 1.2, 1.3, 1.4, 1.5, 1.6, 1.7, 2, 2.2, 2.4, 2.5, 2.7, 2.8, 3, 4, or any other value from 0.2 to 4 of units of IDUA activity/mg protein in the subject's brain.

In some embodiments, the total number of units of IDUA activity delivered to a subject's brain is at least, 25,000 units, i.e., at least 25,000, 30,000, 35,000, 40,000, 45,000, 50,000, 60,000, 70,000, 80,000, 90,000, 110,000, 120,000, 130,000, 140,000, 200,000, 210,000, 220,000, 230,000, 240,000, 250,000, 260,000, 270,000, 280,000, 300,000 or any other total number of IDUA units from about 25,000 to 300,000 units of IDUA activity.

In some embodiments, a therapeutically effective systemic dose comprises at least $5 \times 10^5$, $1 \times 10^6$, $2 \times 10^6$, $3 \times 10^6$, 4, $10^6$, $5 \times 10^6$, $6 \times 10^6$, $7 \times 10^6$, $8 \times 10^6$, $9 \times 10^6$, $1 \times 10^7$, $1.1 \times 10^7$, $1.2 \times 10^7$, $1.5 \times 10^7$, $1.6 \times 10^7$, $1.7 \times 10^7$, $1.8 \times 10^7$, $1.9 \times 10^7$, $2 \times 10^7$, $2.1 \times 10^7$, $3 \times 10^7$, or any other systemic dose from about $5 \times 10^5$ to $3 \times 10^7$ units of IDUA activity.

In other embodiments, a therapeutically effective systemic dose is at least about 100,000 units of IDUA activity/kg body weight, i.e., at least about 110,000, 120,000, 130,000, 140,000, 200,000, 210,000, 220,000, 230,000, 240,000, 250,000, 260,000, 270,000, 280,000, 300,000 or any other number of IDUA units from about 110,000 to 300,000 units of IDUA activity/kg of body weight.

One of ordinary skill in the art will appreciate that the mass amount of a therapeutically effective systemic dose of a HIR Ab-IDUA fusion antibody will depend, in part, on its IDUA specific activity. In some embodiments, the IDUA specific activity of a HIR Ab-IDUA fusion antibody is at least 100,000 U/mg of protein, i.e., at least about 110,000, 120,000, 130,000, 140,000, 200,000, 210,000, 220,000, 230,000, 240,000, 250,000, 260,000, 270,000, 280,000, 300,000, 320,000, 340,000, 350,000, 360,000, 370,000, 373,000, 400,000, 500,000, or any other specific activity value from about 100,000 units/mg to about 500,000 units/mg.

Thus, with due consideration of the specific activity of a HIR Ab-IDUA fusion antibody and the body weight of a subject to be treated, a systemic dose of the HIR Ab-IDUA fusion antibody can be at least 2 mg, i.e., 5, 10, 15, 20, 25, 30, 35, 40, 45, 50, 55, 60, 65, 70, 75, 100, or any other value from about 2 mg to about 100 mg of HIR Ab-IDUA fusion antibody.

The term "systemic administration" or "peripheral administration," as used herein, includes any method of administration that is not direct administration into the CNS, i.e., that does not involve physical penetration or disruption of the BBB. "Systemic administration" includes, but is not limited to, intravenous, intra-arterial intramuscular, subcutaneous, intraperitoneal, intranasal, transbuccal, transdermal, rectal, transalveolar (inhalation), or oral administration. Any suitable HIR Ab-IDUA fusion antibody, as described herein, may be used.

An IDUA deficiency as referred to herein includes, one or more conditions known as Hurler's syndrome, Hurler's disease, mucopolysaccharidosis type I, Scheie syndrome (MPS I S), and Hurler-Scheie (MPS I H-S). The IDUA deficiency is characterized by the buildup of heparan sulfate and dermatan sulfate occurs in the body (the heart, liver, brain etc.).

The compositions of the invention, i.e., an HIR Ab-IDUA fusion antibody may be administered as part of a combination therapy. The combination therapy involves the administration of a composition of the invention in combination with another therapy for treatment or relief of symptoms typically found in a patient suffering from an IDUA deficiency. If the composition of the invention is used in combination with another CNS disorder method or composition, any combination of the composition of the invention and the additional method or composition may be used. Thus, for example, if use of a composition of the invention is in combination with another CNS disorder treatment agent, the two may be administered simultaneously, consecutively, in overlapping durations, in similar, the same, or different frequencies, etc. In some cases a composition will be used that contains a composition of the invention in combination with one or more other CNS disorder treatment agents.

In some embodiments, the composition, e.g., an HIR Ab-IDUA fusion antibody is co-administered to the patient with another medication, either within the same formulation or as a separate composition. For example, the HIR Ab-IDUA fusion antibody could be formulated with another fusion protein that is also designed to deliver across the human blood-brain barrier a recombinant protein other than IDUA. Further, the fusion HIR Ab-IDUA fusion antibody may be formulated in combination with other large or small molecules.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Figure 8:
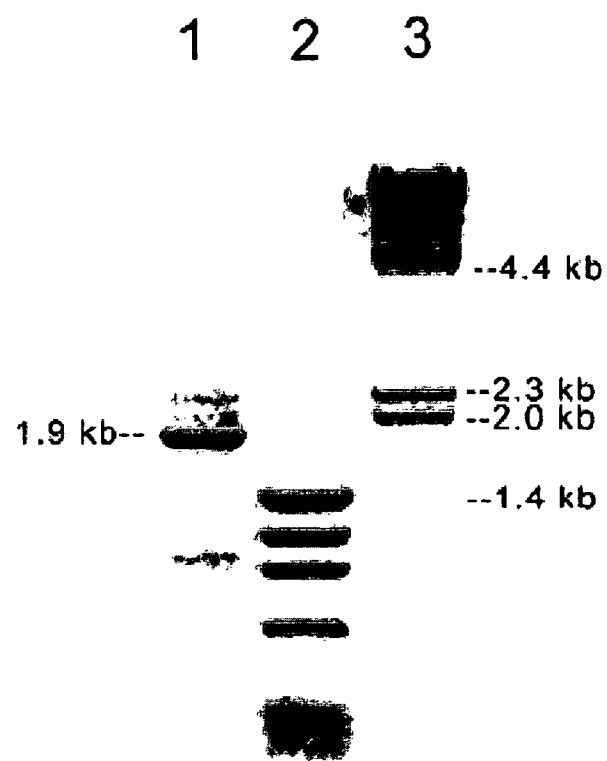
FIG. 8. Ethidium bromide stain of agarose gel of human IDUA cDNA (lane 1), which was produced by PCR from human liver cDNA, and IDUA-specific ODN primers (Table I). Lanes 2 and 3: PhiX174 HaeIII digested DNA standard, and Lambda HindIII digested DNA standard.

Example 1 Construction of Human HIR Ab Heavy Chain-IDUA Fusion Protein Expression Vector Human IDUA cDNA corresponding to amino acids Met1-Pro653 of the mature human IDUA protein, including the 26 amino acid signal peptide (NP_00194), was cloned by reverse transcription (RT) polymerase chain reaction (PCR) using the oligodeoxynucleotides (ODNs) listed in Table 1, designated 'IDUA forward primer' and 'IDUA reverse primer', and human liver polyA+ RNA (Clontech). Human liver cDNA was prepared using the Super Script first-strand synthesis kit (Invitrogen, San Diego, Calif.) and oligodeoxythymidine priming as per the manufacturer's instructions. The IDUAcDNA was cloned by PCR using 2 µl liver cDNA reverse transcription reaction, 0.2 µM IDUA forward and reverse ODN primers (Table 1), 0.2 mM dNTPs and 2.5 U PfuUltraDNA polymerase (Stratagene, San Diego, Calif.) in a 50 µl Pfu buffer (Stratagene). The amplification was performed in a Master cycler temperature cycler (Eppendorf, Hamburg, Germany) with an initial denaturing step of 95° C. for 2 min followed by 30 cycles of denaturing at 95° C. for 30 sec, annealing at 55° C. for 30 sec and amplification at 72° C. for 1 min. PCR products were resolved in 1% agarose gel electrophoresis, and the expected major single band of ~1.9 kb corresponding to the human IDUA cDNA was isolated (FIG. 8). The cloned human IDUA was inserted into the pcDNA eukaryotic expression plasmid at the EcoRV site, and this IDUA expression plasmid was designated pCD-IDUA. The entire expression cassette of the plasmid was confirmed by sequencing both strands.

TABLE 1

Nucleotide Oligodeoxynucleotide primers used in the RT-PCR cloning of human IDUA IDUA FORWARD PRIMER:
5'-phosphate-GCGTGGCCATGCGTCCCCTGCGCCCCGCGCCGCGCT
GCTGGCGCTCCTG (SEQ ID NO: 11)

IDUA-signal peptide FORWARD PRIMER:
5'-phosphate-CAGAGGCCCCGCACCTGGTGCAGGTGGACGCGGCCCG
CGCGCTGTG (SEQ ID NO: 12)

IDUA REVERSE PRIMER:
5'-phosphate-TCATGGATTGCCCGGGGATGGGGGCCCTCTTGGCACA
GGGACC (SEQ ID NO: 13)

DNA sequencing of the expression cassette of the pCD-IDUA encompassed 3,085 nucleotides (nt), including a 715 nt CMV promoter, a 1,962 nt IDUA open reading frame, and a 401 nt BGH sequence, which predicted a 653 amino acid human IDUA protein, including a 26 amino acid signal peptide with 100% identity with the known sequence for human IDUA (GenBank Accession No.: NP_000194).

The pHIR Ab-HC plasmid encodes the heavy chain of a human-mouse chimeric HIR Ab, and pHIR Ab-LC encodes the LC of the chimeric HIR Ab. The HC and LC expression vectors are comprised of intronless cDNA open reading frames (orf), and these cDNAs were obtained by RT-PCR of NSO/1 myeloma cell lines transfected with chromosomal derived HIR Ab HC and LC intron-bearing vectors as described in detail in Boado et al (2007), *Biotechnol Bioeng* 96:381-391. See also U.S. patent application Ser. No. 11/061,956. The sequence of the HIR Ab HC (SEQ ID NO:7) HIR Ab LC (SEQ ID NO:8) are shown in FIGS. 1 and 2, respectively. The sequences of the CDRs of the HIR Ab HC (SEQ ID NOs:1-3) and HIR Ab LC (SEQ ID NOs:4-6) are shown in FIG. 3.

The HIR Ab HC and LC intronless cDNA expression vectors are driven by the cytomegalovirus (CMV) promoter and contain the bovine growth hormone (BGH) polyadenylation (pA) sequence. The engineering of a universal pHIR Ab-HC vector was performed by insertion of a single HpaI site at the end of the HIR Ab HC CH3 open reading frame (ORF) by site directed mutagenesis (SDM), as described previously in Boado et al. supra. All constructs were validated by bi-directional DNA sequencing.

For the engineering of the expression plasmid encoding the fusion protein of the heavy chain (HC) of the HIR Ab and IDUA, designated pCD-HC-IDUA, the human IDUA, minus the 26 amino acid signal peptide, was cloned again by PCR, using the ODNs designated 'IDUA-signal peptide forward primer' and 'IDUA reverse primer.' in Table 1. The ODNs used for PCR are 5'-phosphorylated for direct insertion of the PCR product into the HpaI site of the pHIR Ab-HC expression plasmid. The IDUA-signal peptide forward PCR primer (Table 1) introduces "CA" nucleotides to maintain the open reading frame and to introduce a Ser-Ser linker between the carboxyl terminus of the CH3 region of the HIR Ab HC and the amino terminus of the IDUA minus the 26 amino acid signal peptide of the enzyme. The IDUA reverse PCR primer introduces a stop codon, "TGA," immediately after the terminal Pro of the mature human IDUA protein. The fused IDUA amino acid sequence (SEQ ID NO:9) and the sequence of HIR Ab HC-IDUA fusion protein (SEQ ID NO:10) are shown in FIGS. 4 and 5, respectively. A schematic depiction of the bivalent HIR Ab-IDUA fusion antibody is shown in FIG. 6.

DNA sequencing of the expression cassette of the pCD-HC-IDUA encompassed 4,369 nt, including a 714 nt CMV promoter, a 9 nt full Kozak site (GCCGCCACC), a 3,276 nt HIR Ab HC-IDUA fusion protein open reading frame, and a 370 nt BGH sequence. The plasmid encoded for a 1,091 amino acid protein, comprised of a 19 amino acid IgG signal peptide, the 443 amino acid HIR Ab HC, a 2 amino acid linker (Ser-Ser), and the 627 amino acid human IDUA minus the enzyme signal peptide. The predicted molecular weight of the heavy chain fusion protein, minus glycosylation, is 118,836 Da, with a predicted isoelectric point (pI) of 8.89.

Example 2 Expression Analysis of IDUA and HIR Ab-IDUA Fusion Protein in COS Cells COS cells were plated in 6-well cluster dishes, and were either transfected with the pCD-IDUA, or dual transfected with pHIR Ab-LC and pCD-HC-IDUA using Lipofectamine 2000, with a ratio of 1:2.5, µg DNA:uL Lipofectamine, and conditioned serum free medium was collected at 3 and 7 days. IDUA enzyme activity was measured in both the medium and in the intracellular compartment. The washed monolayer was lysed in 0.4 M sodium formate, pH=3.5, 0.2% Triton X-100; the lysate was sonicated 7 sec 3 times on ice, centrifuged, and the supernatant was taken for IDUA enzyme assay (He et al, (1999), *Mol Genet Metab,* 67:106-112). Transfection of COS cells with pCD-IDUA resulted in high levels of IDUA enzyme activity in both the intracellular compartment and in the medium at 3 and 7 days following transfection, as shown in Table 2.

TABLE 2

IDUA enzyme activity in COS cells following transfection with pCD-IDUA or cotransfection with pCD-HC-IDUA and pHIR Ab-LC

| | Treatment | Intracellular activity (nmol/h/mg$_p$) | Medium activity (nmol/h/ml) |
|---|---|---|---|
| 3 days | Lipofectamine 2000 | 75 ± 7 | 5.2 ± 1.4 |
| | pCD-IDUA | 4070 ± 108 | 1574 ± 156 |
| | pCD-HC-IDUA, plus pCD-LC-1 | 530 ± 34 | 240 ± 25 |
| 7 days | Lipofectamine 2000 | 203 ± 80 | 27 ± 8 |
| | pCD-IDUA | 7969 ± 858 | 2286 ± 25 |
| | pCD-HC-IDUA, plus pCD-LC-1 | 1460 ± 136 | 1194 ± 83 |

Mean ± SE (n = 3 dishes per point).

Dual transfection of COS cells with the pCD-HC-IDUA and the pHIR Ab-LC resulted in medium levels of IDUA enzyme activity of 240±25 and 1,194±83 nmol/hr/mL at 3 and 7 days after transfection, respectively (Table 2). The COS intracellular IDUA enzyme activity at 3 and 7 days is 530±34 and 1,460±136 nmol/hr/mg protein, respectively (Table 2). For production of larger amounts of fusion protein, COS cells were transfected in 10×T500 flasks. The 3 day and 7 day medium was pooled, and the 2 L of serum free conditioned medium was concentrated to 400 mL with tangential flow filtration (Millipore) followed by purification with protein A affinity chromatography.

The purity of protein A purified fusion protein produced by COS cells was evaluated with 12% sodium dodecyl sulfate polyacrylamide gel electrophoresis (SDSPAGE) with 5% β-mercaptoethanol. Immunoreactivity was tested with a primary rabbit antibody to human IDUA, provided by Prof. E. Neufeld, UCLA, or a primary goat antiserum against human IgG heavy and light chains (Vector Labs, Burlingame, Calif.).

Figure 9:
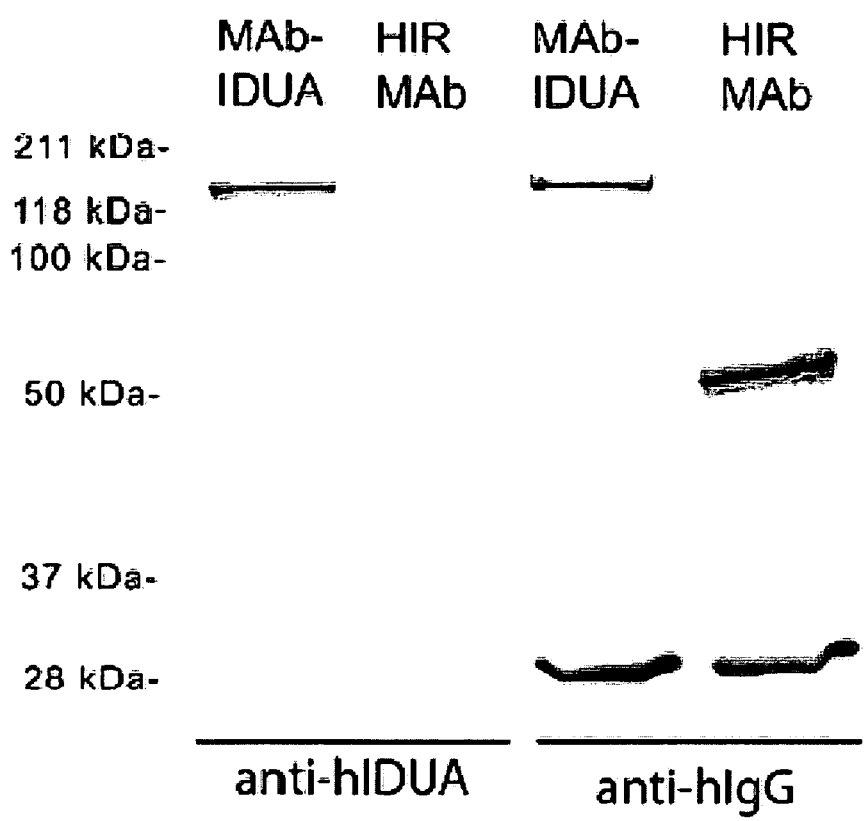
FIG. 9. Western blot with either anti-human (h) IgG primary antibody (right panel) or rabbit anti-human IDUA primary antiserum (left panel). The immunoreactivity of the HIR Ab-IDUA fusion antibody is compared to the HIR Ab alone. Both the HIR Ab-IDUA fusion antibody and the HIR Ab have identical light chains on the anti-hIgG Western. The HIR Ab-IDUA fusion heavy chain reacts with both the anti-hIgG and the anti-human IDUA antibody, whereas the HIR Ab heavy chain only reacts with the anti-hIgG antibody. The size of the HIR Ab-IDUA fusion heavy chain, 130 kDa, is about 80 kDa larger than the size of the heavy chain of the HIR Ab, owing to the fusion of the 80 kDa IDUA to the 50 kDa HIR Ab heavy chain.

On Western blotting of the purified HIR Ab-IDUA fusion protein, the anti-human IgG antibody reacts with a 130 kDa HC for the fusion protein, and a 50 kDa HC for the chimeric HIR Ab, and the difference in size, 80 kDa, is due to the fusion of IDUA (FIG. 9, right panel). The anti-human IgG antibody reacts equally with the light chain of either the HIR Ab-IDUA fusion protein or the HIR Ab, since both proteins are comprised of the same light chain. The anti-IDUA antibody reacts with the 130 kDa HC of the fusion protein, but not with the HC of the chimeric HIR Ab (FIG. 9, left panel).

Example 3 Analysis of HIR Binding and IDUA Activity

The affinity of the fusion protein for the HIR extracellular domain (ECD) was determined with an ELISA. CHO cells permanently transfected with the HIR ECD were grown in serum free media (SFM), and the HIR ECD was purified with a wheat germ agglutinin affinity column, as previously described in Coloma et al. (2000) *Pharm Res*, 17:266-274. The HIR ECD was plated on Nunc-Maxisoth 96 well dishes and the binding of the HIR Ab, or the HIR Ab-IDUA fusion protein, to the HIR ECD was detected with a biotinylated goat anti-human IgG (H+L) secondary antibody, followed by avidin and biotinylated peroxidase (Vector Labs, Burlingame, Calif.). The concentration of either HIR Ab or HIR Ab-IDUA fusion protein that gave 50% maximal binding was determined with a non-linear regression analysis.

Figure 10:
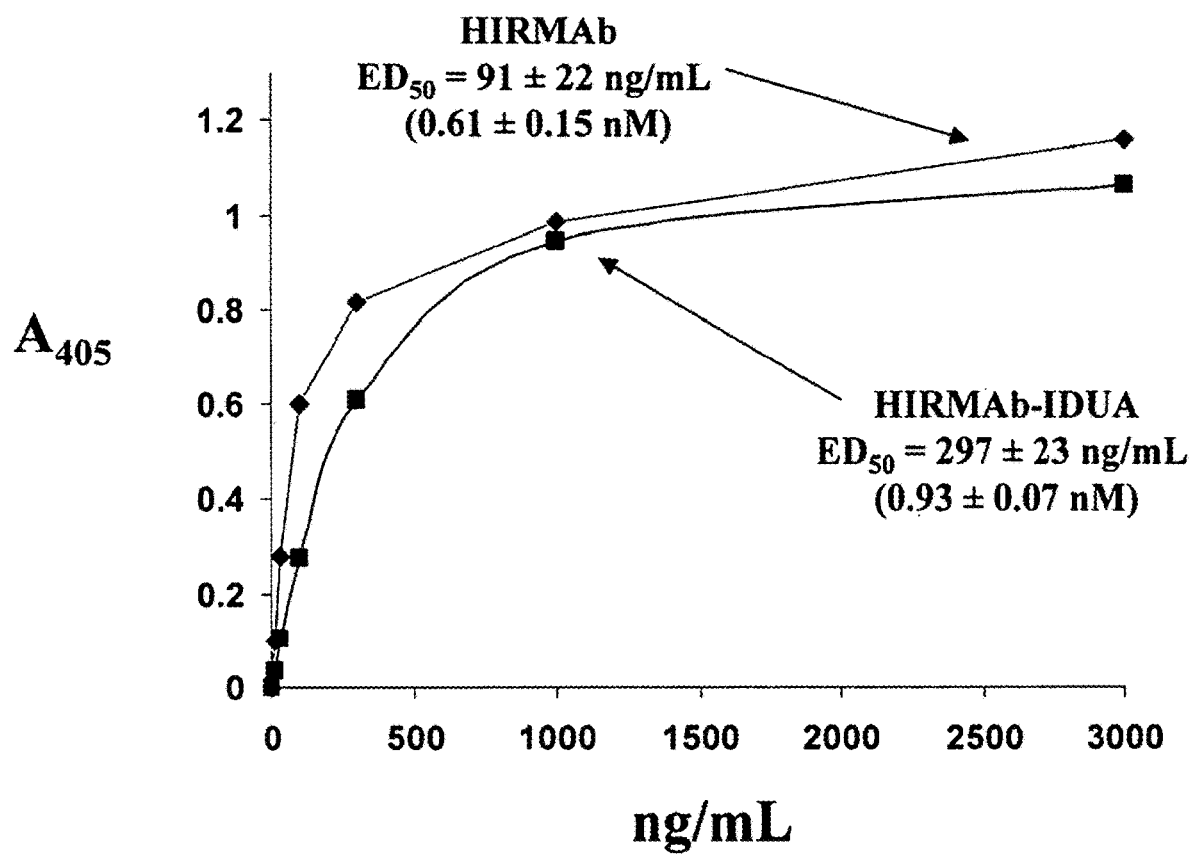
FIG. 10. Binding of either the chimeric HIR Ab or the HIR Ab-IDUA fusion protein to the HIR extracellular domain (ECD) is saturable. The $ED_{50}$ of HIR Ab-IDUA binding to the HIR ECD is comparable to the $ED_{50}$ of the binding of the chimeric HIR Ab.

As shown in FIG. 10 there was comparable binding of either the chimeric HIR Ab or the HIR Ab-IDUA fusion protein for the HIR ECD with ED50 of 0.61±0.15 nM and 0.93±0.07 nM, respectively.

The IDUA enzyme activity was determined with a fluorometric assay using 4-methylumbelliferyl α-L-iduronide (MUBI), which was purchased from Glycosynth, Ltd. (Cheshire, England). This substrate is hydolyzed to 4-methylumbelliferone (4-MU) by IDUA, and the 4-MU is detected fluorometrically with a Farrand filter fluorometer using an emission wavelength of 450 nm and an excitation wavelength of 365 nm. A standard curve was constructed with known amounts of 4-MU (Sigma-Aldrich, St. Louis, Mo.). The assay was performed at 37 C at pH=3.5, and was terminated by the addition of 1 mL of 0.5 M glycine (pH=10.3). One unit=1 nmole substrate/hr (see Kakkis et al., (1994), *Prot Expr Purif*, 5:225-232). The IDUA enzyme activity of the purified HIR Ab-IDUA fusion protein was 363±37 nmol/hr/ug protein; the assay was linear with respect to both time and mass of fusion protein. Based on these results, we concluded that the HIR Ab-HC-IDUA fusion/HIR Ab-LC antibody is a bifunctional antibody that binds selectively to the IR ECD and retains a high level of IDUA activity.

Example 4 HIR Ab-IDUA Fusion Protein Uptake and Biological Activity in MPS Type I Fibroblasts Type I MPS Hurler fibroblasts and healthy human fibroblasts were grown in 6-well cluster dishes to confluency. The medium was aspirated, wells washed with phosphate buffered saline (PBS), and incubated with 1 mL of Dulbecco's modified Eagle medium (DMEM) without serum, along with a range of concentrations of the HIR Ab-IDUA fusion protein, for 60 min at 37 C. The medium was aspirated, and the wells were washed extensively (1 mL/well, 5 washes) with PBS, and the monolayer was taken up in 0.4 mL/well of lysis buffer (0.4 M sodium formate, 0.2% Triton X-100, pH=3.5), sonicated on ice 7 seconds 3 times, and microfuged 10 min 4 C. The supernatant was removed for IDUA enzyme activity and bicinchoninic acid (BCA) protein assay. The uptake of the fusion protein was expressed as nmol/hr of IDUA enzyme activity per mg protein.

The HIR Ab-IDUA fusion protein was taken up by MPS Type I fibroblasts (FIG. 11A). The basal IDUA activity in these cells without treatment is very low (less than 5 nmol/hr/mg of protein). The intracellular IDUA enzyme activity increased in proportion to the concentration of medium HIR Ab-IDUA. The uptake of the HIR Ab-IDUA by the cells was inhibited 55% by the addition of 10 μg/ml murine HIR Ab (p<0.001), but was not inhibited by the addition of 4 mM mannose-6-phosphate (p>0.05). The IDUA enzyme activity in the Hurler fibroblasts approximates 250 nmol/hr/mgp at a medium HIR Ab-IDUA concentration of 2000 ng/mL (FIG. 11A). The horizontal line in FIG. 11A denotes the IDUA activity level in healthy human fibroblasts.

The effect of the HIR Ab-IDUA fusion protein on cell glycosoaminoglycan (GAG) accumulation was assessed with a 35S incorporation assay (Unger et al, 1994). Type I MPS or healthy human fibroblasts were plated to 6-well cluster dishes at 250,000 cells/well and grown for 4 days in DMEM with 10% fetal bovine serum (FBS). The medium was discarded, the wells were washed with PBS, and 1 mL/well of low sulfate F12 medium with 10% dialyzed FBS was added, along with 5 mM CaCl2, the HIR Ab-IDUA fusion protein (0.3 μg/mL), and 10 μCi/mL of 35S-sodium sulfate (Amersham, Chicago, Ill.). Following a 48 hr incubation at 37 C, the medium was aspirated, the wells were washed with cold PBS (1 mL, 5 washes), and the cells were lysed with 0.4 mL/well of 1 N NaOH. The lysate was heated 60 C 60 min to solubilize protein, an aliquot was removed for BCA protein assay, and the sample was counted for radioactivity with a Perkin Elmer Tri-Carb 2100 liquid scintillation counter. The data were expressed as 35S CPM per μg protein.

The Hurler fibroblasts, with or without treatment by the HIR Ab-IDUA fusion protein, and the healthy human fibroblasts, were incubated for 48 hours in the presence of 35S-sodium sulfate, which is incorporated into intracellular GAGs. Treatment with the HIR Ab-IDUA fusion protein reduced GAG accumulation in Hurler fibroblasts by 70% as compared to healthy fibroblasts (p<0.0005) (FIG. 11B).

The prevention of GAG accumulation in Hurler fibroblasts (FIG. 11B) indicated that the HIR Ab-IDUA fusion antibody was directed to the lysosomal compartment of the cell, where GAG accumulates.

To confirm targeting of the HIR Ab-IDUA fusion antibody to the lysosome, confocal microscopy was performed. Type I MPS Hurler fibroblasts were grown overnight in DMEM with 10% FBS to 50% confluency. The medium was aspirated, the wells washed well with PBS, and the cells were treated with fresh DMEM with no serum and containing 20 μg/mL of the HIR Ab-IDUA fusion protein. Following a 24 hr incubation at 37 C, the medium was aspirated, the wells washed extensively with cold PBS, and the cells were fixed with either 100% cold acetone for 20 min at −20 C, or 4% paraformaldehyde at 4 C for 20 min. Following a PBS wash, the plates were blocked with 10% donkey serum, and then co-labeled with a 1:2000 dilution of the rabbit anti-IDUA antiserum, and 10 μg/ml of a mouse MAb to human lysosomal associated membrane protein (LAMP)-1 (BD Pharmingen). Negative control antibodies were the same dilutions of either rabbit serum or mouse IgG. The secondary antibodies (Molecular Probes/Invitrogen) were 5 μg/mL each of 488 conjugated donkey anti-mouse IgG (green channel) and 594 conjugated donkey anti-rabbit IgG (red channel). The slides were imaged with a Zeiss LSM 5 PASCAL confocal microscope with dual argon and helium/neon lasers equipped with Zeiss LSM software, as described previously (Zhang et al, (2004), *Hum Gene Ther*, 15:339-350).

Figure 12:
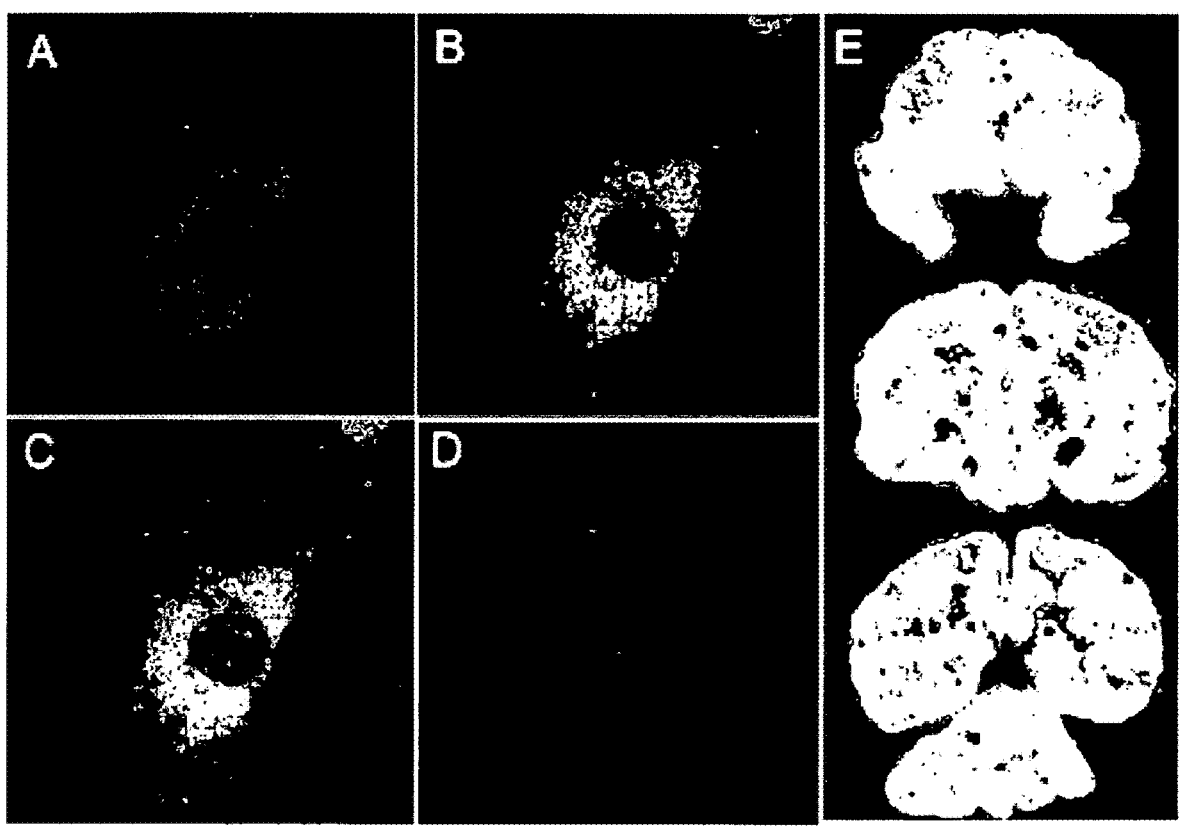
FIG. 12. (A, B, C, D) Hurler fibroblasts were incubated with HIR Ab-IDUA fusion protein for 24 hours and then fixed and immune stained for confocal microscopy. The fixed cells were stained with a rabbit polyclonal antibody to human IDUA (panel A: red channel signal, shown here in black and white), and a mouse monoclonal antibody to human lysosomal associated membrane protein (LAMP)-1 (panel B: green channel signal, shown here in black and white). The overlap image in panel C shows sequestration of the HIR Ab-IDUA fusion protein within lysosomes. Panel D is an overlap image of negative control primary antibodies: rabbit serum and mouse IgG. (E) Film autoradiography of Rhesus monkey brain removed 2 hours after an intravenous administration of [$^{125}I$]-HIR Ab-IDUA fusion protein. Coronal sections through the forebrain (top panel), midbrain (middle panel), and hindbrain/cerebellum (bottom panel) are shown.

The cell IDUA and LAMP-1 immunoreactivity is shown in FIGS. 12A and 12B, respectively. The overlap image in FIG. 12C shows that the fusion protein was immunoreactive with an anti-IDUA antiserum, and the lysosomal marker, LAMP-1. No immune staining was detected with the control antibodies (FIG. 12D). Based on these results, we concluded that the HIR Ab-IDUA fusion antibody was targeted to lysosomes, as would be expected for IDUA.

Example 5 Analysis of Brain Delivery and Pharmacokinetics of HIR Ab-IDUA Fusion Protein in the Rhesus Monkey The HIR Ab-IDUA fusion protein was iodinated with [125I]-iodine to a specific activity of 24 μCi/μg, and a trichloroacetic acid (TCA) precipitability of 99%. The fusion protein was iodinated on the same day as injection into the primate. A 7-year old female Rhesus monkey, weighing 7.2 kg, was obtained from Covance, Inc. (Alice, Tex.), and anesthetized with intramuscular ketamine, and isoflurane by inhalation. The anesthetized primate was administered by a single intravenous injection a dose of 957 μCi of [125I]-HIR Ab-IDUA fusion protein mixed with 400 μg (0.06 mg/kg) of unlabeled HIR Ab-IDUA fusion protein in a final volume of 3 mL. Serum was collected at multiple time points over a 120 min period and analyzed for (a) serum 125I radioactivity, and (b) serum IDUA enzyme activity. The serum glucose of the anesthetized, overnight-fasted primate was constant throughout the 120 min study period, and averaged 88±1 mg %, which indicates that the administration of the HIR Ab fusion protein caused no interference of the endogenous insulin receptor, and had no effect on glycemic control. At 120 minutes after drug injection, the animal was euthanized, and brain and organ radioactivity was analyzed with a gamma counter; brain was also analyzed with the capillary depletion method, as described previously (Triguero et al., (1990), *J Neurochem*, 54:1882-1888), similar to prior work on the brain delivery of [125I]-labeled murine HIR Ab in the Rhesus monkey (Pardridge et al, (1995), *Pharm Res*, 12:807-816). The capillary depletion technique demonstrates the transcytosis of the fusion protein through the BBB in vivo, and into brain.

The delivery of the fusion protein by brain, and other organs, at 120 minutes after intravenous injection is expressed as a % of injected dose (ID)/gram organ, and these data are given in Table 3. The fusion protein is delivered to all parts of brain, as shown by the film autoradiogram of the primate brain at 2 hours after intravenous injection of the [125I]-HIR Ab-IDUA fusion protein (FIG. 12E).

TABLE 3

Brain and organ delivery of an HIR Ab-IDUA Fusion Antibody

| Tissue | % ID/100 g | VD (ul/g) |
|---|---|---|
| Cerebrum gray matter | 1.05 ± 0.07 | 134 ± 8 |
| Cerebrum white matter | 0.32 ± 0.02 | 41 ± 2 |
| Cerebellum gray/white | 0.74 ± 0.17 | 95 ± 22 |
| Liver | 11.7 ± 0.15 | 1485 ± 18 |
| Spleen | 12.1 ± 0.16 | 1541 ± 20 |
| Lung | 5.2 ± 0.4 | 655 ± 48 |
| Kidney | 4.0 ± 0.1 | 505 ± 14 |
| Heart | 1.4 ± 0.08 | 183 ± 9 |
| Skeletal muscle (triceps) | 0.48 ± 0.002 | 61 ± 1 |
| Fat (omental) | 1.7 ± 0.4 | 221 ± 58 |

Mean ± SD (n = 3 replicates)

The serum $^{125}$I radioactivity concentration profile, expressed as % injected dose (ID)/mL (FIG. 13A), was fit to a bi-exponential equation, as described previously (Pardridge et al, (1995), *Pharm Res*, 12:807-816), to yield the pharmacokinetic (PK) parameters in Table 4. The parameters for the [125I]-fusion protein are compared to the PK parameters reported previously (Coloma et al, (2000), *Pharma Res*, 17:266-274) for the [111In]-HIR Ab (Table 4).

The decline in serum radioactivity with time after injection was paralleled by the decline in serum IDUA enzyme activity (FIG. 13A). The serum IDUA enzyme activity in the primate before injection of the fusion protein was 1.5±0.4 units/mL, and was 2120±59, 496±5, 194±20, 67±4, 19±1, 12±2, and 14±1 units/mL, at 1, 2.5, 5, 15, 30, 60, and 120 min after injection, respectively.

The brain delivery of the fusion protein at 2 hours after injection in the primate is expressed as a volume of distribution (VD), which is the ratio of DPM/gram brain divided by the DPM/uL serum (FIG. 13B). The brain VD for the fusion protein exceeds 140 μl/gram in the brain homogenate, and is much larger than the VD for [3H]-mouse IgG2a, which has no receptor binding, and does not cross the BBB (Pardridge et al, supra). The brain VD for the [3H]-mouse IgG2a, 18 µl/gram, equals the arterial blood volume of the brain (Ito et al, 2005), which is indicative of lack of transport across the BBB of an antibody that has no BBB receptor specificity. The brain VD for the [$^{125}$I]-fusion protein is also ~140 µl/gram in the post-vascular supernatant (FIG. 13B), as determined with the capillary depletion method.

TABLE 4

Pharmacokinetic parameters for [$^{125}$I]-HIR Ab-IDUA fusion protein and [$^{111}$In]-HIR Ab

| Parameter | [$^{125}$I]-HIR Ab-IDUA | [$^{111}$In]-HIR Ab |
|---|---|---|
| $A_1$ (% ID/ml) | 1.00 ± 0.22 | 0.15 ± 0.01 |
| $A_2$ (% ID/ml) | 0.077 ± 0.013 | 0.10 ± 0.01 |
| $k_1$ (min$^{-1}$) | 0.65 ± 0.11 | 0.12 ± 0.01 |
| $k_2$ (hr$^{-1}$) | 0.42 ± 0.26 | 0.11 ± 0.06 |
| $t_{1/2}^1$ (min) | 1.1 ± 0.2 | 5.8 ± 0.6 |
| $t_{1/2}^2$ (hr) | 1.7 ± 1.0 | 6.3 ± 0.6 |
| CL (ml/min/kg) | 1.11 ± 0.47 | 0.22 ± 0.08 |
| Vss (ml/kg) | 139 ± 37 | 116 ± 11 |

In table 4 $A_1$, $A_2$, $k_1$, and $k_2$ are the intercepts and slopes of the bi-exponential function describing the decay in plasma concentration with time. The parameters for the HIR Ab-IDUA fusion protein were determined for the Rhesus monkey in this study, and the parameters for HIR Ab were determined previously in the adult Rhesus monkey (Coloma et al, 2000). All data are normalized for differences in body weight. The $t_{1/2}^1$ and $t_{1/2}^2$ are computed from $k_1$ and $k_2$, respectively, and are the half-times of the decay curves for each exponent. Clearance (CL) and steady state volume of distribution (Vss) are computed from $A_1$, $A_2$, $k_1$, and $k_2$ using previously described pharmacokinetic formulations (Pardridge et al, 1995).

The brain VD of the post-vascular supernatant of the [$^{125}$I]-fusion protein is equal to the VD of the brain homogenate (FIG. 13B), which indicated that the fusion protein was transcytosed through the BBB and into brain parenchyma. The brain VD for the vascular pellet was low, 1.1±0.1 µl/g.

Based on these data, we concluded that the HIR Ab-IDUA fusion antibody was taken up at a high rate into the primate protein, as shown in Table 3. This high rate of delivery into the brain was due to the targeting of the insulin receptor on the BBB. The fusion protein underwent transcytosis across the primate BBB in vivo, as demonstrated by the capillary deletion technique (FIG. 13B).

Importantly, brain delivery of the HIR Ab-IDUA fusion antibody was 1.05±0.05% of injected dose per 100 gram brain (Table 3). The size of the Rhesus monkey brain is approximately 100 grams; therefore, about 1% of the injected dose is distributed to the primate brain. Owing to this high rate of delivery of the fusion antibody into the brain, it will be possible to produce normal levels of IDUA enzyme activity in the brain of patients with Hurler's syndrome. The delivery of the fusion protein by brain, expressed as a % of ID/gram, in the human will be reduced, as compared to the primate, in proportion to body weight. Therefore, the expected brain delivery of the fusion protein in the human brain is about 0.1% of the injected dose per 100 gram brain, or about 1% of the ID per 1000 g human brain. A normal level of IDUA enzyme activity for the human brain ranges from 0.5-1.5 units/mg protein (Crow et al, (1983), *J Clin Pathol,* 36:415-430) and there is a total of about 100,000 mg of protein in an average size human brain. Thus, it would be expected that delivery to the brain of between 50,000 units to about 150,000 units of IDUA activity should suffice to rescue a deficit in brain IDUA activity as observed in, e.g., Hurler's syndrome. As recombinant IDUA itself does not cross the BBB, this has not been feasible. In contrast, given the observed delivery of the HIR Ab-IDUA fusion antibody into the brain, and its high IDUA specific activity, we conclude that achieving delivery of a normalizing level of IDUA activity in the brain of patients suffering from an IDUA deficiency (e.g., as in Hurler's syndrome) will be achieved by systemic administration of an HIR Ab-IDUA fusion antibody. Further, due to the broad distribution of the fusion antibody in all organs examined (Table 3), systemic administration of the HIR Ab-IDUA fusion antibody may also normalize IDUA enzyme activity outside the CNS in Hurler's patients.

Example 6. Expression Vectors for Permanent Transfection of Host Cell

Figure 14:
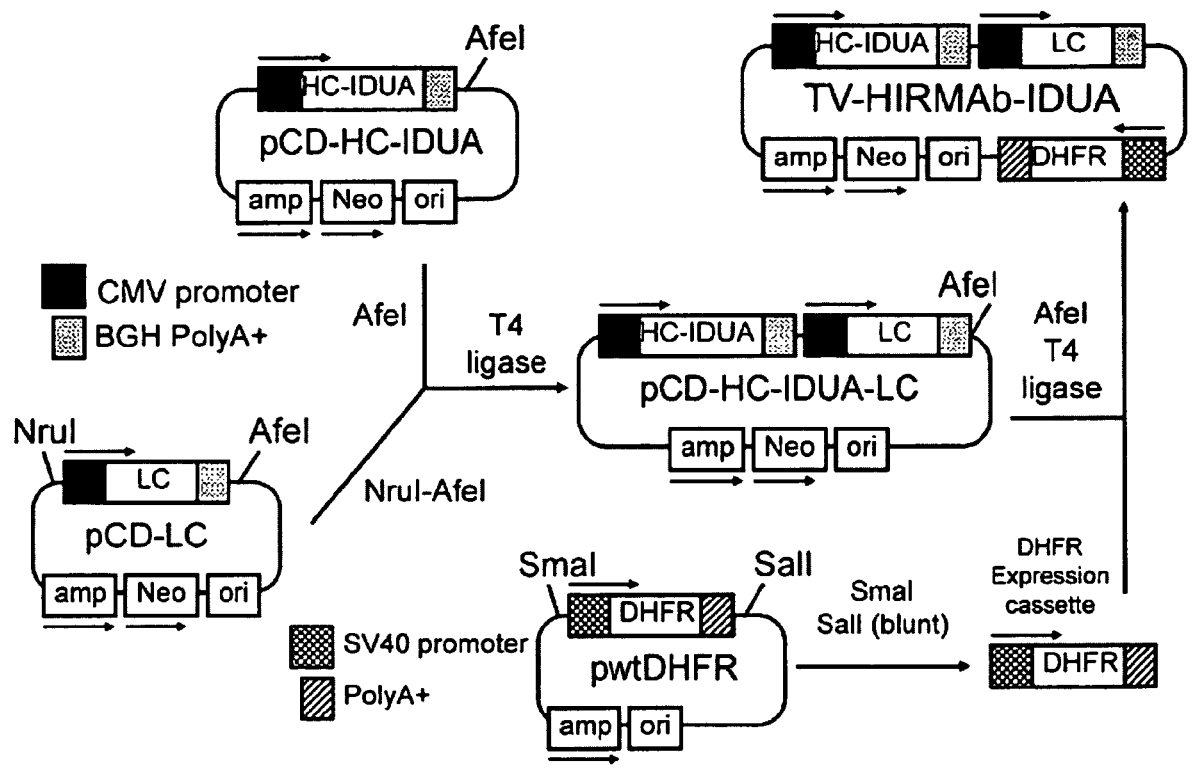
FIG. 14. Genetic engineering of tandem vector (TV-HIRMAb-IDUA) encoding 4 separate and tandem expression cassettes encoding the heavy chain (HC) fusion gene, the light chain (LC) gene, the DHFR gene, and the neo gene.

The genetic engineering of TV-HIRMAb-IDUA was accomplished in several linear steps, comprised of the following:
(1) A "double gene" expression plasmid, designated pCD-HC-IDUA-LC (FIG. 14) was engineered from 2 precursor plasmids, pCD-HC-IDUA, and pCD-LC, following linearization of pCD-HC-IDUA by AfeI, and release of the LC expression cassette with NruI and AfeI, and closure of the new plasmid with T4 ligase, as shown in FIG. 14.
(2) A "triple gene" tandem vector (TV) expression plasmid, designated TV-HIRMAb-IDUA (FIG. 14) was engineered from 2 precursor plasmids, pCD-HC-IDUA-LC and pwtDHFR, where pwtDHFR encodes for the wild type (wt) murine dihydrofolate reductase (DHFR). The DHFR expression cassette was released from pwtDHFR with SmaI and SalI. The end of SalI was filled with T4 DNA polymerase and deoxynucleotide triphosphates. In parallel, the pCD-HC-IDUA-LC was opened with AfeI. The new TV was closed with T4 ligase.

The engineering of the TV was validated by (a) agarose gel electrophoresis, (b) IDUA expression in COS cells, and (c) by bi-directional DNA sequencing. The entire 7,822 nucleotides (nt) of the TV-HIRMAb-IDUA was subjected to bi-directional DNA sequencing using custom oligodeoxynucleotides (ODNs), and the nt sequence is given in SEQ ID NO. 14. The DNA sequence was comprised of 7,822 nt, which included the following domains:
  714 nt cytomegalovirus (CMV) promoter
  9 nt Kozak sequence (GCCGCCACC)
  3,276 nt open reading frame (orf) encoding the fusion gene of the HIRMAb HC and IDUA
  297 nt bovine growth hormone (BGH) polyA (pA) sequence
  23 nt linker
  731 nt CMV promoter
  9 nt Kozak sequence
  705 orf encoding the HIRMAb LC
  291 nt BGH pA
  254 SV40 promoter
  9 nt Kozak sequence
  564 murine DHFR of
  940 hepatitis B virus (HBV) pA The TV-HIRMAb-IDUA also included the expression cassette encoding neo, the neomycin resistance gene, to enable selection with G418 (FIG. 14). It was necessary to include the HC fusion gene, the LC gene, and the DHFR gene on a single piece of DNA, or tandem vector (FIG. 14) to allow for equally high expression of all 3 genes in the transfected host cell.

The TV-HIRMAb-IDUA sequence, from nt 724-3,999 (SEQ ID NO. 14), encoded for a 1,091 amino acid (AA) HC fusion protein, which was comprised of a 19 AA IgG signal peptide, the 442 AA HIRMAb HC, a 3 AA linker, and the 627 AA human IDUA enzyme, and is given in SEQ ID. NO. 15. The predicted molecular weight (MW) of the non-glycosylated HC was 118,795 Daltons (Da) and the predicted isoelectric point (pI) of the fusion HC protein was 8.85. The TV-HIRMAb-IDUA sequence, from nt 5,060-5,764 (SEQ ID NO. 14), encoded for a 234 AA LC protein (SEQ ID NO. 16), which was comprised of a 20 AA IgG signal peptide, and the 214 AA HIRMAb LC. The predicted MW of the LC was 23,398 Da and the predicted pI of the LC protein was 5.45. The TV-HIRMAb-IDUA sequence, from nt 6,319-6,882 (SEQ ID NO. 14), encoded for a DHFR protein (SEQ ID NO. 17) that was comprised of 187 AA.

Example 7. Permanent Transfection of Chinese Hamster Ovary Cells with TV-HIRMAb-IDUA DG44 Chinese hamster ovary (CHO) cells were grown in serum free HyQ SFM4CHO utility medium (HyClone), containing 1×HT supplement (hypoxanthine and thymidine). DG44 CHO cells ($5 \times 10^6$ viable cells) were electroporated with 5 µg PvuI-linearized TV-HIRMAb-IDUA plasmid DNA. The cell-DNA suspension is then incubated for 10 min on ice. Cells are electroporated with BioRad pre-set protocol for CHO cells, i.e. square wave with pulse of 15 msec and 160 volts. After electroporation, cells are incubated for 10 min on ice. The cell suspension is transferred to 50 ml culture medium and plated at 125 µl per well in 4×96-well plates (10,000 cells per well). A total of 10 electroporations and 4,000 wells are performed per study.

Following electroporation (EP), the CHO cells are placed in the incubator at 37 C and 8% CO2. Owing to the presence of the neo gene in the TV, transfected cell lines are initially selected with G418. The TV-HIRMAb-IDUA also contains the gene for DHFR (FIG. 14), so the transfected cells are also selected with 20 nM methotrexate (MTX) and HT deficient medium. Once visible colonies are detected at about 21 days after EP, the conditioned medium is sampled for human IgG by ELISA. Wells with high human IgG signals in the ELISA are transferred from the 96-well plate to a 24-well plate with 1 mL of HyQ SFM4CHO-Utility. The 24-well plates are returned to the incubator at 37 C and 8% CO2. The following week IgG ELISA is performed on the clones in the 24-well plates. This is repeated through the 6-well plates to T75 flasks and finally to 60 mL and 125 mL square plastic bottles on an orbital shaker. At this stage, the final MTX concentration is 80 nM, and the medium IgG concentration, which is a measure of HIRMAb-IDUA fusion protein in the medium is >10 mg/L at a cell density of 106/mL.

Clones selected for dilutional cloning (DC) are removed from the orbital shaker in the incubator and transferred to the sterile hood. The cells are diluted to 500 mL in F-12K medium with 5% dialyzed fetal bovine serum (d-FBS) and Penicillin/Streptomycin, and the final dilution is 8 cells per mL, so that 4,000 wells in 40×96-well plates can be plated at a cell density of 1 cell per well (CPW). Once the cell suspension is prepared, within the sterile hood, a 125 uL aliquot is dispensed into each well of a 96-well plate using an 8-channel pipettor or a precision pipettor system. The plates are returned to the incubator at 37 C and 8% CO2. The cells diluted to 1 cell/well cannot survive without serum. On day 6 or 7, DC plates are removed from the incubator and transferred to the sterile hood where 125 µl of F-12K medium with 5% dialyzed fetal bovine serum (d-FBS) is added to each well. This selection media now contains 5% d-FBS, 30 nM MTX and 0.25 mg/mL Geneticin. On day 21 after the initial 1 CPW plating, aliquots from each of the 4,000 wells are removed for human IgG ELISA, using robotics equipment. DC plates are removed from the incubator and transferred to the sterile hood, where 100 µl of media is removed per well of the 96-well plate and transferred into a new, sterile sample 96-well plate using an 8-channel pipettor or the precision pipettor system.

On day 20 after the initial 1 CPW plating, 40×96-well Immunoassay plates are plated with 100 uL of 1 µg/mL solution of Primary antibody, a mouse anti-human IgG in 0.1M NaHCO₃. Plates are incubated overnight in the 4 C refrigerator. The following day, the ELISA plates are washed with 1×TBST 5 times, and 100 uL of 1 ug/mL solution of secondary antibody and blocking buffer are added. Plates are washed with 1× TBST 5 times. 100 uL of 1 mg/mL of 4-nitrophenyl phosphate di(2-amino-2-ethyl-1,3-propanediol) salt in 0.1M glycine buffer are added to the 96-well immunoassay plates. Plates are read on a microplate reader. The assay produces IgG output data for 4,000 wells/experiment. The highest producing 24-48 wells are selected for further propagation.

The highest producing 24-well plates from the 1 CPW DC are transferred to the sterile hood are gradually subcloned through 6-well dishes, T75 flasks, and 125 mL square plastic bottles on an orbital shaker. During this process the serum is reduced to zero, at the final stage of centrifugation of the cells and resuspension in SFM.

The above procedures are repeated with a second round of dilutional cloning, at 0.5 cells/well (CPW). At this stage, approximately 40% of the wells show any cell growth, and all wells showing growth also secrete human IgG. These results confirm that on average only 1 cell is plated per well with these procedures, and that the CHO cell line originates from a single cell.

Example 8. Manufacturing of CHO-Derived HIRMAb-IDUA Fusion Protein

Figure 15:
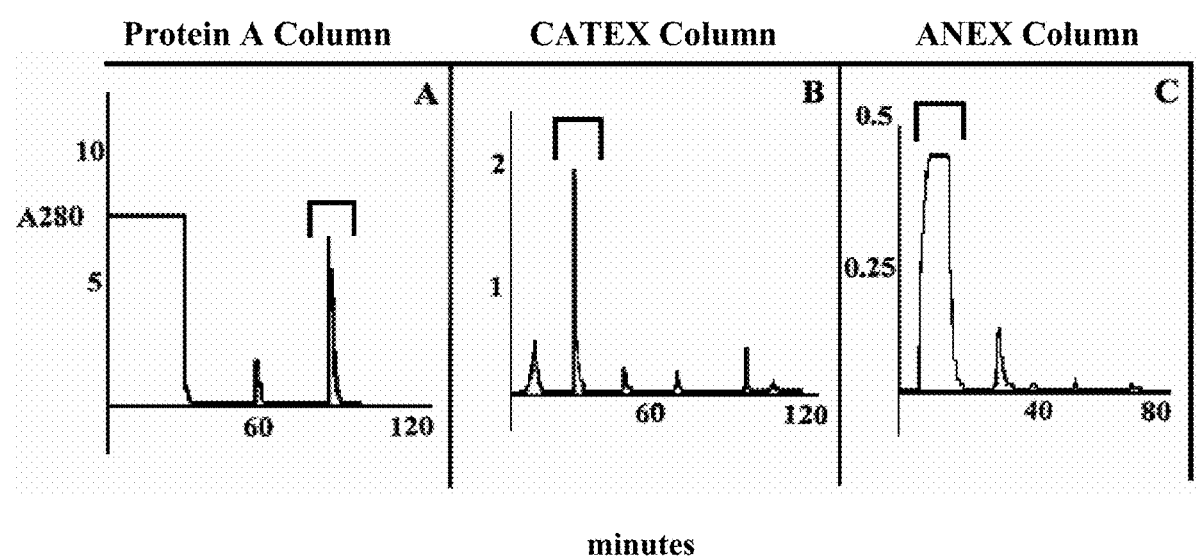
FIG. 15. The 3-column purification of CHO derived HIRMAb-IDUA fusion protein uses protein A affinity chromatography (A), SP Sepharose cation exchange (CATEX) chromatography (B), and Q Sepharose anion exchange (ANEX) chromatography (C). The peak of fusion protein elution for each column is bracketed in the figure.

Following the second round of dilutional cloning, the highest producing cell line secreting the HIRMAb-IDUA fusion protein was propagated in serum free medium to a total volume of 2,000 mL in several 1 L square plastic bottles on an orbital shaker. The HIRMAb-IDUA fusion protein was purified from the CHO cell conditioned medium using the following down-stream processing:

Depth filtration with a 0.2 m² 0.65 µm GF filter in series with an 0.05 m² µm Sartopore-2 µltrafilter Volume reduction to 400 mL using tangential flow filtration (TFF) system Ultra-filtration with a 0.2 mm µltra-filter and application to a column of protein A Sepharose 4 Fast Flow. Following application to the column, the column was eluted with 1 M NaCl, which elutes DNA non-specifically absorbed to the column, and the product is eluted as a single peak with 0.1 M sodium acetate/pH=3.7 (FIG. 15A). The acid eluate was neutralized with 1 M Tris base and concentrated to 5 mL with a Centriprep-30

Cation exchange (CATEX) chromatography in bind-elute mode was performed with a column of SP Sepharose FF equilibrated with 0.02 M MES and 0.05 M NaCl. The conductivity of the sample was reduced to <5 mS/cm prior to application to the column. The column was successively eluted with step gradients of 0.02 M MES/pH=5.5 containing 0.25 M NaCl, 0.35 M NaCl, 0.5 M NaCl, and 1M NaCl. The HIRMAb-IDUA fusion protein eluted in 0.5 M NaCl, as shown in FIG. 15B.

Anion exchange (ANEX) chromatography in flow-through mode was performed with a column of Q Sepharose FF equilibrated with 0.025 M MES/pH=5.5 and 0.05 M NaCl. The conductivity of the sample was reduced to <7 mS/cm. The HIRMAb-IDUA fusion protein eluted in the flow-through as shown in FIG. 15C.

The purity and potency of the CHO derived HIRMAb-IDUA fusion protein was assessed with the following procedures:

(a) SDS-PAGE.

Figure 16:
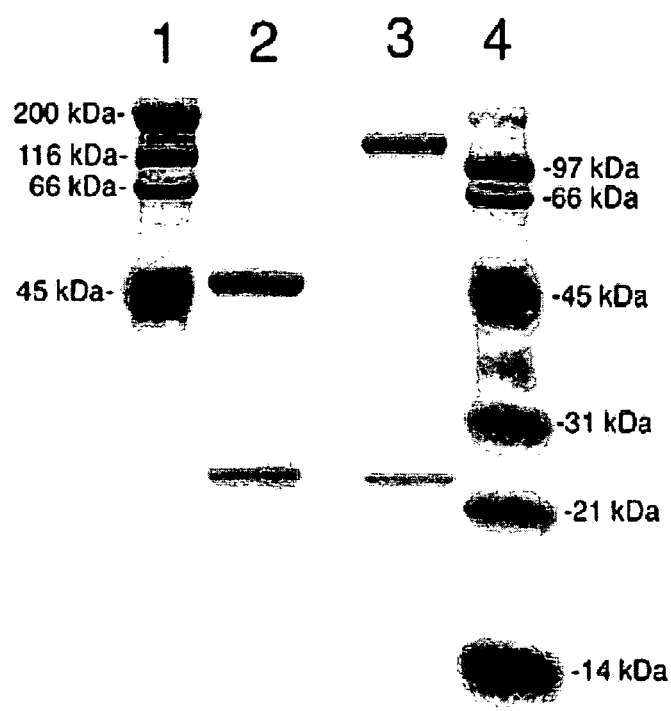
FIG. 16. The HIRMAb-IDUA fusion protein, derived from CHO cells, is purified to homogeneity on reducing SDS-PAGE, as shown in lane 3. Lane 2 is the chimeric HIRMAb without the fused IDUA. The MW of the HC of the HIRMAb-IDUA fusion protein is about 85 kDa larger than the HC of the HIRMAb, owing to the fusion of the IDUA enzyme. Lanes 1 and 4 are MW standards.

The CHO-derived HIRMAb-IDUA fusion protein was purified to homogeneity based on reducing sodium dodecyl sulfate polyacrylamide gel electrophoresis (SDS-PAGE), as demonstrated in FIG. 16 (lane 3). The chimeric HIRMAb is applied to lane 2 of FIG. 16, and HIRMAb-IDUA fusion protein is applied to lane 3 of FIG. 16. The size of the light chain (LC) of both proteins is the same as both proteins are comprised of the same LC. The size of the heavy chain (HC) of HIRMAb-IDUA fusion protein is 130 kDa (lane 3, FIG. 16), whereas the size of the HC of the chimeric HIRMAb is 50 kDa (lane 2, FIG. 16), and the difference in size is due to fusion of the 80 kDa IDUA to the HC of the chimeric HIRMAb.

(b) IDUA and Human IgG Western Blot.

Figure 17:
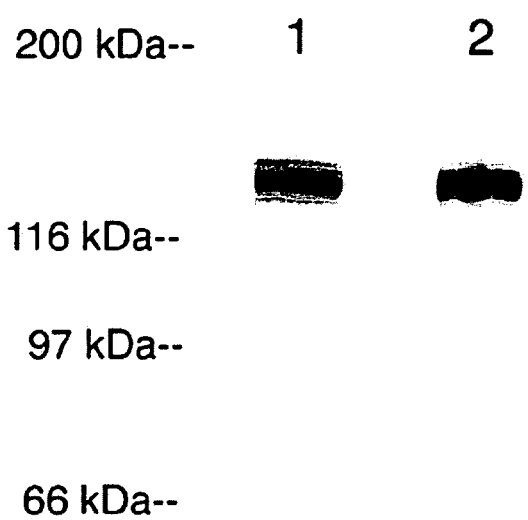
FIG. 17. Western blot of the HIRMAb-IDUA fusion protein, derived from CHO cells, using primary antibodies to either the human IgG heavy chain (lane 1) or to human IDUA (lane 2). Both antibodies react equally to the 130 kDa HIRMAb-IDUA fusion protein heavy chain.

The CHO derived HIRMAb-IDUA fusion protein was electrophoresed on a 7.5% SD S-PAGE gel and blotted to nitrocellulose for Western blotting with primary antibodies to either human IgG (lane 1, FIG. 17), or to human IDUA (lane 2, FIG. 17). Both the anti-human IgG antibody and the anti-human IDUA antibody reacted specifically with the heavy chain of HIRMAb-IDUA fusion protein, which migrated with a molecular weight of 130 kDa in this reducing gel (FIG. 17).

(c) Human Insulin Receptor (HIR) Binding Assay.

Figure 18:
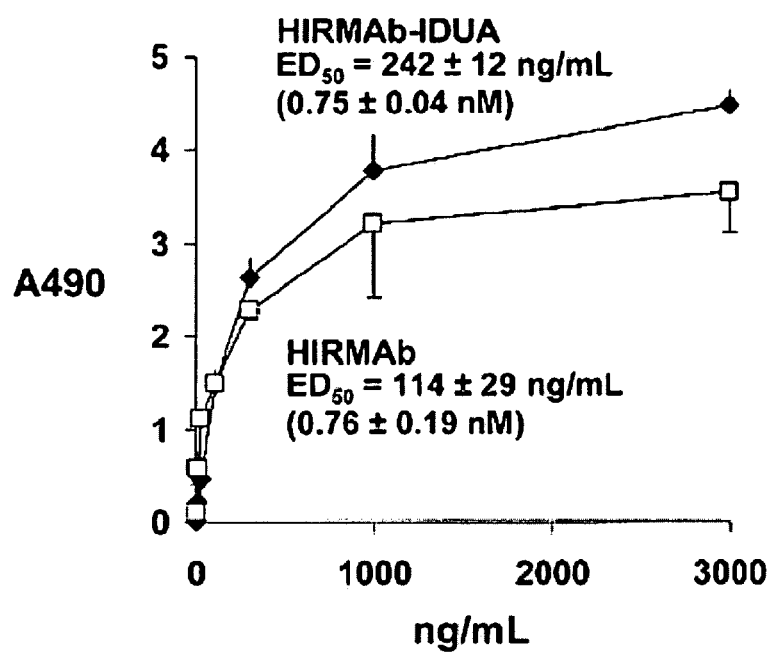
FIG. 18. Binding of either the chimeric HIRMAb or the CHO cell derived HIRMAb-IDUA fusion protein to the HIR extracellular domain (ECD) is saturable. The $ED_{50}$ of HIRMAb-IDUA binding to the HIR ECD is comparable to the $ED_{50}$ of the binding of the chimeric HIRMAb, which indicates the affinity for the HIR is not impaired by fusion of the IDUA to the HIRMAb heavy chain.

The extracellular domain (ECD) of the HIR was purified by lectin affinity chromatography from serum free medium conditioned by CHO cells that were permanently transfected with the HIR ECD. The HIR ECD was plated in ELISA wells to bind the chimeric HIRMAb without IDUA fused, and the CHO-derived HIRMAb-IDUA fusion protein. As shown in FIG. 18, the ED50 of the chimeric HIRMAb or the HIRMAb-IDUA fusion protein binding to the HIR is not significantly different, and is 0.75 nM. These data indicate the affinity of the HIRMAb for the HIR is not affected by the fusion of IDUA to the carboxyl terminus of the IgG. The binding constants shown in FIG. 18 were determined by non-linear regression analysis of the binding isotherms.

(d) IDUA Enzyme Activity of the HIRMAb-IDUA Fusion Protein.

Figure 19:
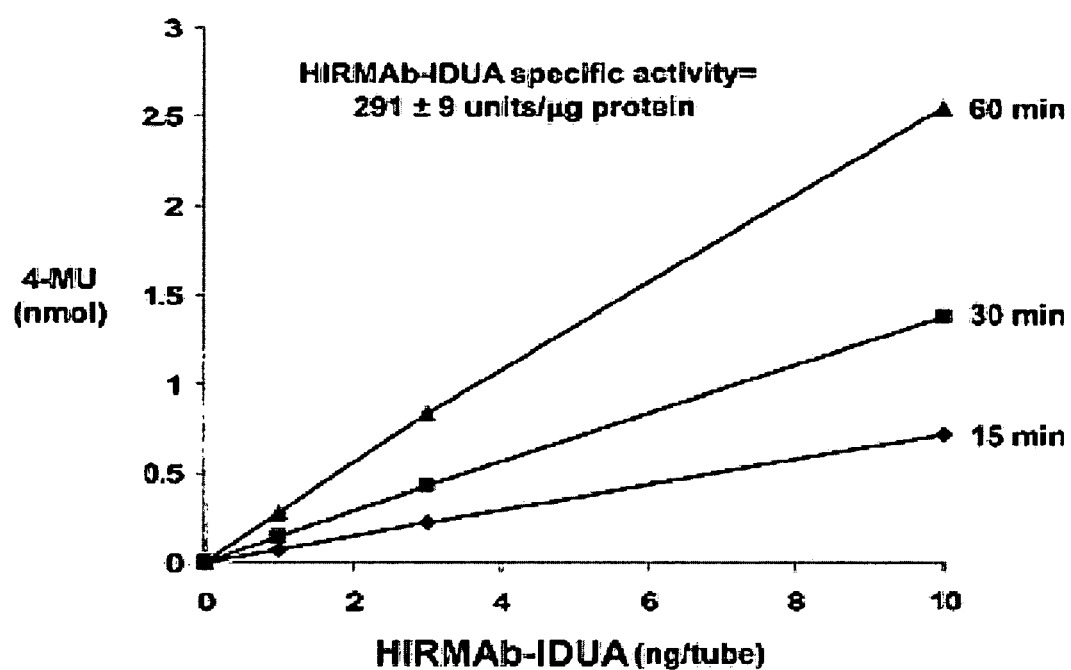
FIG. 19. The IDUA enzyme activity of the CHO derived HIRMAb-IDUA fusion protein is 291±9 units/µg protein, where 1 unit=1 nmol/hr, based on a fluorometric enzymatic assay that uses 4-methylumbelliferyl L-α-iduronide (MUBI) as a substrate, and 4-methylumbelliferone (4-MU) as an assay standard The IDUA enzyme activity is linear with respect to time and mass of HIRMAb-IDUA fusion protein. The IDUA enzyme specific activity of the HIRMAb-IDUA fusion protein is comparable to recombinant IDUA.

The IDUA enzyme activity of the CHO-derived HIRMAb-IDUA fusion protein was determined with a fluorometric assay using 4-methylumbelliferyl α-L-iduronide (MUBI) as the assay substrate. This substrate is hydolyzed to 4-methylumbelliferone (4-MU) by IDUA, and the 4-MU is detected fluorometrically with a filter fluorometer using an emission wavelength of 450 nm and an excitation wavelength of 365 nm. A standard curve was constructed with known amounts of 4-MU. The assay was performed at 37 C at pH=3.5, and was terminated by the addition of 1 mL of 0.1 M glycine (pH=10.3). One unit=1 nmol/hr. IDUA enzyme activity of the HIRMAb-IDUA fusion protein was linear with respect to time and concentration (FIG. 19). The IDUA enzyme specific activity of the CHO derived the HIRMAb-IDUA fusion protein is 291±9 units per µg protein (FIG. 19). The IDUA enzyme specific activity of recombinant IDUA is 240 units per µg protein; therefore, the IDUA enzyme activity of the HIRMAb-IDUA fusion protein is comparable to that of recombinant IDUA.

(e) Size Exclusion High Performance Liquid Chromatography.

Figure 20:
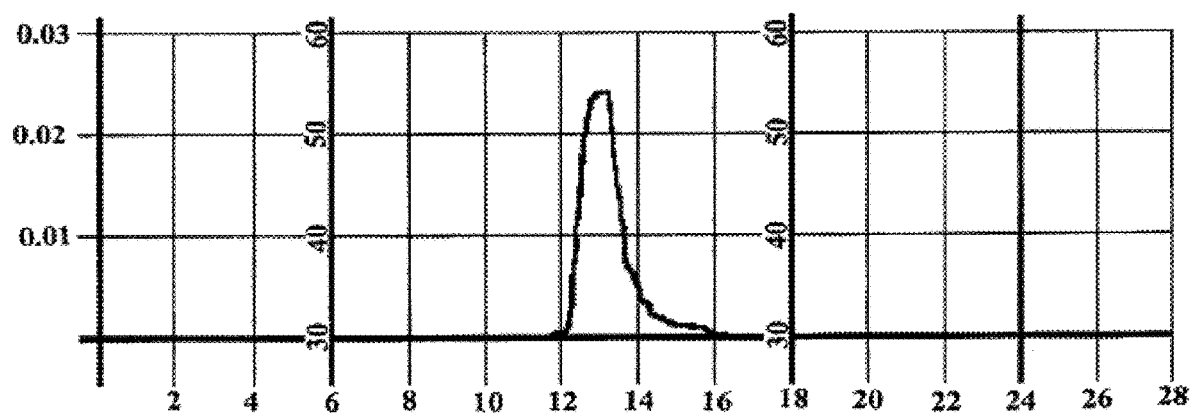
FIG. 20. Size exclusion chromatography (SEC) HPLC using 2 TosoHaas G3000SWXL columns in series. The CHO derived HIRMAb-IDUA fusion protein elutes as a single species without aggregates.

The absence of aggregates in the purified HIRMAb-IDUA fusion protein was demonstrated with size exclusion chromatography (SEC) high performance liquid chromatography (HPLC) using 2 G3000 SWXL columns, 0.78×30 cm, in series, and an HPLC pump at 0.5 mL/min with detection at 280 nm. As shown in FIG. 20, the CHO-derived HIRMAb-IDUA fusion protein elutes as a single peak, removed from the void volume, with no detectable aggregates.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A pharmaceutical composition comprising a pharmaceutically acceptable excipient and a therapeutically effective dose of a fusion antibody having α-L-iduronidase activity, wherein the fusion antibody comprises:
   (a) a fusion protein comprising an amino acid sequence of an immunoglobulin heavy chain and an α-L-iduronidase (IDUA); and
   (b) an immunoglobulin light chain;
   wherein the fusion antibody binds to an endogenous transferrin receptor of a blood brain barrier (BBB) transport system, wherein the IDUA retains at least 30% of its enzymatic activity compared to an unfused IDUA, wherein the therapeutically effective dose comprises at least about $1\times10^6$ units of α-L-iduronidase activity or at least about 140,000 units/Kg of body weight, wherein at least about 0.5% of the therapeutically effective dose is delivered to the brain, wherein the amino acid sequence of the IDUA is covalently linked to the carboxy terminus of the amino acid sequence of the immunoglobulin heavy chain, and wherein an IDUA specific activity of the fusion antibody is at least about 250,000 units/mg.

2. The pharmaceutical composition of claim 1, wherein the fusion protein of (a) further comprises a linker between the amino acid sequence of the IDUA and the carboxy terminus of the amino acid sequence of the immunoglobulin heavy chain.

3. The pharmaceutical composition of claim 1, wherein the immunoglobulin heavy chain is an $IgG_1$.

4. The pharmaceutical composition of claim 1, wherein the immunoglobulin light chain is an immunoglobulin light chain of kappa class.

5. The pharmaceutical composition of claim 1, wherein the pharmaceutical composition is sterile filtered.

6. The pharmaceutical composition of claim 1, wherein the pharmaceutical composition further comprises a salt selected from the group consisting of mineral acid salts and organic acid salts.

7. The isolated polynucleotide of claim 6, wherein the mineral acid salt is selected from the group consisting of hydrochlorides, hydrobromides, phosphates, and sulfates.

8. The isolated polynucleotide of claim 6, wherein the organic acid salt is selected from the group consisting of acetates, propionates, malonates, and benzoates.

9. The pharmaceutical composition of claim 1, wherein the pharmaceutical composition further comprises between 0.01 to 1% polysorbate-80.

10. The pharmaceutical composition of claim 1, wherein the pharmaceutical composition further comprises a carbohydrate additive.

11. The pharmaceutical composition of claim 10, wherein the carbohydrate additive is selected from the group consisting of mannitol, sorbitol, and trehalose.

* * * * *